(12) United States Patent
Oliva et al.

(10) Patent No.: US 9,877,966 B1
(45) Date of Patent: Jan. 30, 2018

(54) COMBINATION THERAPY FOR THE INHIBITION OF METASTASIS AND TUMORIGENESIS

(71) Applicants: Eugene J. Oliva, Emerson, NJ (US); Paul Diamond, New York, NY (US)

(72) Inventors: Eugene J. Oliva, Emerson, NJ (US); Paul Diamond, New York, NY (US)

( * ) Notice: Subject to any disclaimer, the term of this patent is extended or adjusted under 35 U.S.C. 154(b) by 0 days.

(21) Appl. No.: 15/233,934

(22) Filed: Aug. 10, 2016

Related U.S. Application Data

(60) Provisional application No. 62/203,337, filed on Aug. 10, 2015.

(51) Int. Cl.
*A61K 31/519* (2006.01)
*A61K 31/44* (2006.01)
*A61K 31/5377* (2006.01)

(52) U.S. Cl.
CPC ............ *A61K 31/519* (2013.01); *A61K 31/44* (2013.01); *A61K 31/5377* (2013.01)

(58) Field of Classification Search
USPC ....................................... 514/63, 234.2, 274
See application file for complete search history.

(56) References Cited

U.S. PATENT DOCUMENTS

2008/0275071 A1* 11/2008 Fukushima ............ A61K 31/44
514/274
2014/0323438 A1* 10/2014 Frankowski ......... C07D 487/04
514/63

OTHER PUBLICATIONS

Norton; Cancer Treatment and Research; 2013; 158:139-152.*
Wang et al., Abstract 5368: Metarrestin effectively disassembles PNCs and inhibits metastasis, Proceedings: AACR 106th Annual Meeting 2015; Apr. 18-22, 2015.
Frankowski et al., Discovery and Development of Small Molecules That Reduce PNC Prevalence, Probe Reports from the NIH Molecular Libraries Program. Bethesda (MD) 2010.
Kanis et al., Metarrestin: A novel compound active against ovarian cancer, Gynecologic Oncology Oct. 2015 vol. 139, Issue 1, p. 190.

* cited by examiner

*Primary Examiner* — Pancham Bakshi

(57) ABSTRACT

The invention provides therapeutic compositions and methods for the inhibition of metastasis and for treatment of cancers in human and non-human mammals that are directed to the coformulation and/or coadministration of a dehydropyrimidine dehydrogenase inhibitor such as gimeracil and a pyrrolopyrimidine compound.

10 Claims, No Drawings

COMBINATION THERAPY FOR THE INHIBITION OF METASTASIS AND TUMORIGENESIS

CROSS-REFERENCE TO RELATED APPLICATIONS

This application claims the benefit of U.S. provisional application Ser. No. 62/203,337 filed Aug. 10, 2015, which is hereby incorporated by reference in its entirety.

FIELD OF THE INVENTION

The invention relates to field of pharmaceutical prevention and treatment of metastasis.

BACKGROUND OF THE INVENTION

The perinucleolar compartment is a structure whose prevalence in cancer cells has been found to correlate with the metastatic activity and potential of the cells.

Gimeracil (5-chloro-2,4-dihydroxypyridine) is an inhibitor of dihydropyrimidine dehydrogenase (DPYD), which degrades pyrimidine including 5-fluorouracil in the blood. Gimeracil was originally added to an oral fluoropyrimidine derivative S-1 to yield prolonged 5-fluorouracil concentrations in serum and tumor tissues. One process for the production of gimeracil is disclosed in U.S. Pat. No. 7,557,216 which is hereby incorporated by reference in its entirety.

SUMMARY OF THE INVENTION

In one aspect, the invention provides a pharmaceutical composition for the treatment of a cancer and/or inhibition of metastasis in a mammal that includes a DPYD inhibitor such as gimeracil or a pharmaceutically salt thereof and a compound according to formula I, such as trans-4-(7-benzyl-4-imino-5,6-diphenylpyrrolo[2,3-d]pyrimidin-3-yl)cyclohexan-1-ol, or a pharmaceutically acceptable salt thereof that at least partially inhibits the formation of the perinucleolar compartment and/or disrupts the assembly of the perinucleolar compartment and/or inhibits metastasis or migration of cancer cells. The pharmaceutical composition may, for example, include at least one excipient. Administration of the pharmaceutical composition may, for example, be oral or parenteral, such as by injection.

A related aspect of the invention provides a method for treating a cancer and/or inhibiting metastasis in mammal such as a human patient that includes administering the aforementioned pharmaceutical formulation.

A further aspect of the invention provides a method for treating a cancer and/or inhibiting metastasis in mammal such as a human patient that includes coadministering to the mammal in need thereof a DPYD inhibitor such as gimeracil or a pharmaceutically salt thereof and a compound according to formula I, such as trans-4-(7-benzyl-4-imino-5,6-diphenylpyrrolo[2,3-d]pyrimidin-3-yl)cyclohexan-1-ol, or a pharmaceutically acceptable salt thereof that at least partially inhibits the formation of the perinucleolar compartment and/or disrupts the assembly of the perinucleolar compartment and/or inhibits metastasis or migration of cancer cells. Administration of either or both component pharmaceutical compounds (or salts thereof) may, for example, be oral or parenteral, such as by injection.

DESCRIPTION OF THE INVENTION

One embodiment of the invention provides pharmaceutical compositions for the inhibition of metastasis or treatment of a cancer such as a metastatic cancer in a human or non-human mammal in need thereof that include a DPYD inhibitor such as gimeracil or a pharmaceutically acceptable salt thereof and one or more of the pyrrolopyrimidine compounds disclosed in U.S. Pub. No. 2014/0323438 A1 and PCT/US2012/070155 (WO2013/090912) or a pharmaceutically acceptable salt thereof each of said references incorporated herein by reference in its entirety with the disclosure of PCT/US2012/070155 also explicitly recited below.

Another embodiment of the invention provides a method of inhibiting metastasis or treating a cancer such as a metastatic cancer in a human or non-human mammal in need thereof that includes co-administering DPYD inhibitor such as gimeracil or a pharmaceutically acceptable salt thereof and one or more of the pyrrolopyrimidine compounds disclosed in U.S. Pub. No. 2014/0323438 A1 and PCT/US2012/070155 (WO2013/090912) or a pharmaceutically acceptable salt thereof. Said coadministration may include administering a pharmaceutical composition that includes both gimeracil and the one or more pyrrolopyrimidine compounds or coadministering gimeracil and the one or more pyrrolopyrimidine compounds as separate compositions to the subject.

Each of the DPYD inhibitor such as gimeracil or salt thereof and the one or more pyrrolopyrimidine compounds disclosed in U.S. Pub. No. 2014/0323438 A1 and PCT/US2012/070155 and herein or salts thereof may, for example, be provided and/or administered in a dose 0.01 mg/kg to 250 mg/kg (drug weight/subject weight). Gimeracil may, for example, be provided in a daily dose of 1 mg to 20 mg such as 4 mg to 10 mg, such as 4 mg to 5 mg. Gimeracil dosing may, for example, be within the same ranges disclosed herein below for the recited pyrrolopyrimidine compounds. Each of the DPYD inhibitor such as gimeracil or salt thereof and the pyrrolopyrimidine compound or salt thereof may be administered in amounts that are therapeutically effective when the agents are coadministered.

The aforementioned combination compositions and coadministration methods of the invention may, for example, be used in any of the manners and for any of the indications set forth in the following disclosure of PCT/US2012/070155 for the pyrrolopyrimidine compounds thereof except that the DPYD inhibitor such as gimeracil or salt thereof and the one or more pyrrolopyrimidine compounds is used. Thus, wherever it is recited in the following disclosure of PCT/US2012/070155 which forms a part of this specification, the present invention provides corresponding embodiments in which a DPYD inhibitor such as gimeracil or a pharmaceutically salt thereof is also present and/or concomitantly used. The immediately following section of this specification describes the perinucleolar compartment (PNC) and the sets forth compounds of formula I that at least partially inhibit PNC formation and/or at least partially disrupt assembled (already existing) PNCs substantially as disclosed in PCT/US2012/070155, which may be used in embodiments of the instant invention.

In one embodiment, the invention provides a compound of the formula:

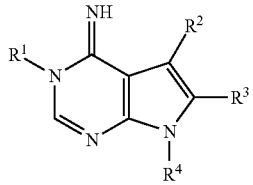

(I)

wherein $R^1$ is selected from alkyl, hydroxyalkyl, thioalkyl, alkoxyalkyl, alkylthioalkyl, cycloalkyl, hydroxycycloalkyl, hydroxycycloalkylalkyl, thiocycloalkyl, alkoxycycloalkyl, alkylthiocycloalkyl, dialkylaminoalkyl, heterocyclyl, heterocyclylalkyl, heteroaryl, arylalkyl, arylalkylpiperidin-4-yl, arylpiperazinylalkyl, and heteroarylalkyl, $R^2$ is aryl or heteroaryl, $R^3$ is selected from H, alkyl, cycloalkyl, aryl, heteroaryl, arylalkyl, and heteroarylalkyl, $R^4$ is selected from alkyl, cycloalkyl, cycloalkylalkyl, aryl, heteroaryl, arylalkyl, and heteroarylalkyl, or a pharmaceutically acceptable salt thereof, wherein $R^1$, $R^2$, $R^3$, and $R^4$, other than H, are optionally substituted on the aryl and/or alkyl portion with one or more substituents selected from halo, alkyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, alkylenedioxy, and alkylcarbonyl, with the proviso that when $R^2$ and $R^3$ are both unsubstituted phenyl and $R^4$ is unsubstituted benzyl, $R^1$ is not 3-hydroxypropyl.

In accordance with an embodiment, $R^2$ is phenyl, optionally substituted with one or more substituents selected from halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl.

In accordance with certain embodiments, $R^2$ is phenyl.

In accordance with any of the above embodiments, $R^3$ is phenyl, optionally substituted with one or more substituents selected from halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl.

In accordance with any of the above embodiments, $R^4$ is benzyl, wherein the phenyl ring is optionally substituted with one or more substituents selected from alkyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, and alkylcarbonyl.

In accordance with any of the above embodiments, $R^4$ is benzyl.

In accordance with any of the above embodiments, $R^1$ is a 5 or 6-membered heterocyclyl group having at least one hetero atom selected from O, N, and S; a hydroxy $C_1$-$C_7$ cycloalkyl group; a hydroxy $C_1$-$C_6$ alkyl group; a N,N-di($C_1$-$C_6$ alkyl)amino $C_1$-$C_6$ alkyl group; a $C_1$-$C_6$ alkoxy $C_1$-$C_6$ alkyl group; a heteroaryl $C_1$-$C_6$ alkyl group; a heterocyclyl $C_1$-$C_6$ alkyl group; phenyl $C_1$-$C_6$ alkyl group wherein the phenyl ring is substituted with one or more $C_1$-$C_6$ alkoxy groups; N-benzyl piperazinyl; N-phenyl piperazinylalkyl; a phenyl $C_1$-$C_6$ alkyl group where the alkyl is substituted with a hydroxy group; or a 5 or 6 membered heteroarylamino $C_1$-$C_6$ alkyl group wherein the heteroaryl group has at least one hetero atom selected from O, N, and S.

In accordance with certain preferred embodiments, $R^1$ is selected from the following:

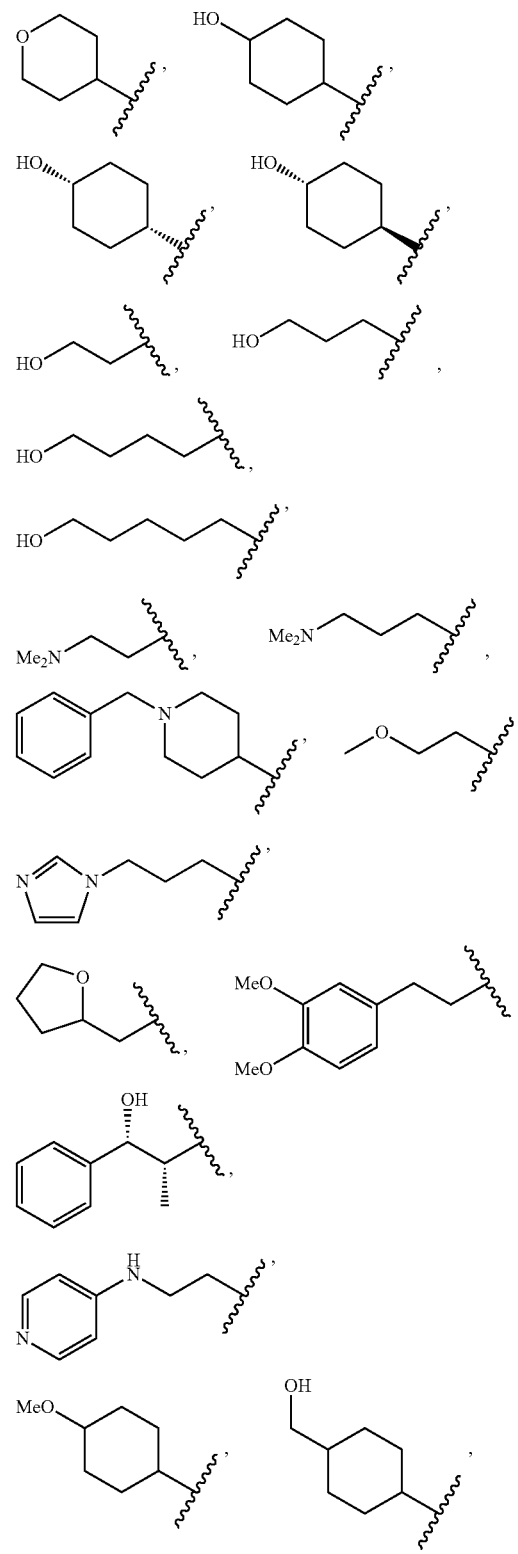

-continued
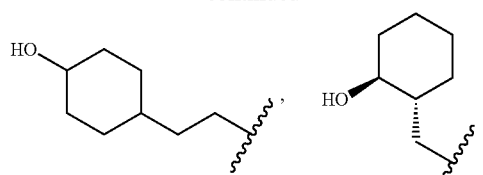
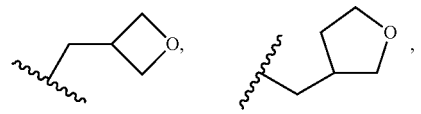
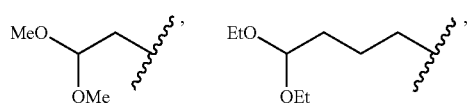
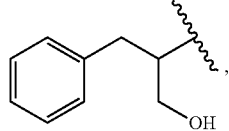
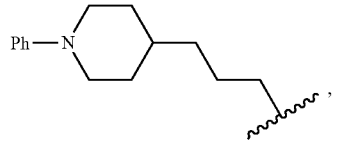
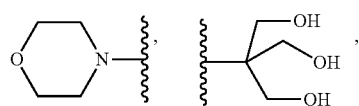
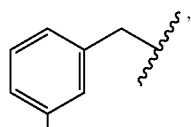
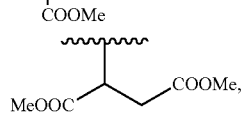
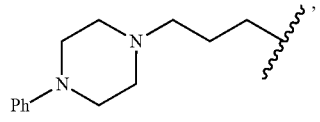
and
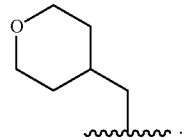
.
In accordance with certain specific embodiments, $R^2$ is phenyl, $R^3$ is phenyl, $R^4$ is benzyl, and $R^1$ is selected from the following:
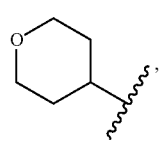 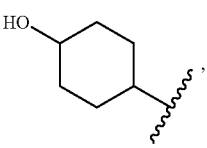
-continued
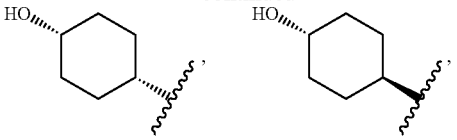
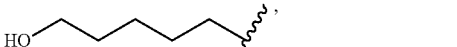
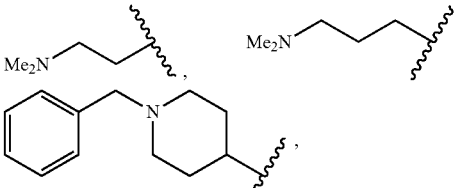
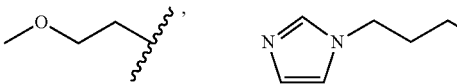
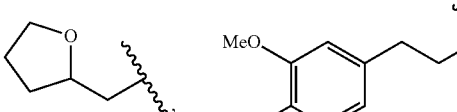
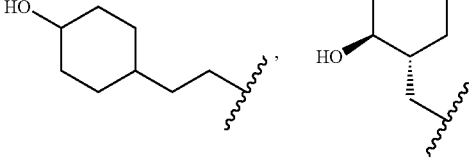
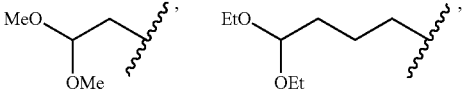

-continued

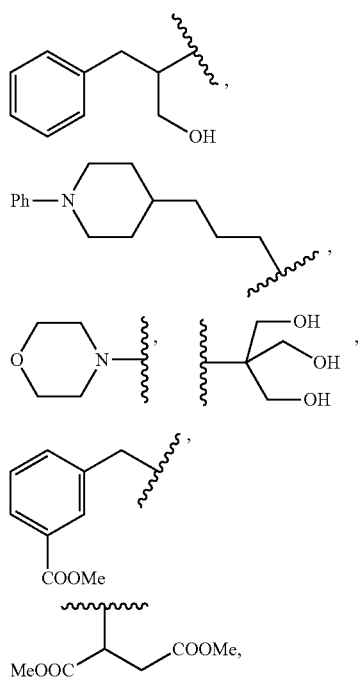

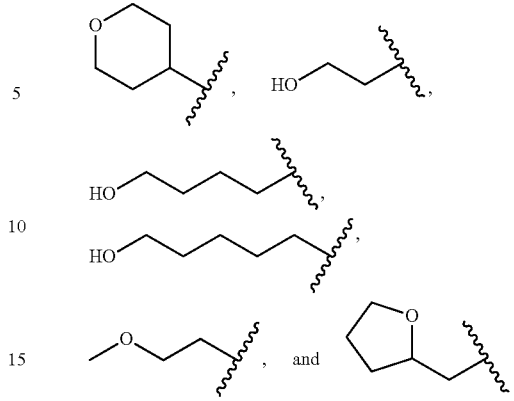

In accordance with any of the above embodiments, $R^4$ is phenylethyl, wherein the phenyl ring is optionally substituted with one or more substituents selected from alkyl, hydroxyalkyl, alkoxy, and alkoxycarbonyl.

In accordance with certain embodiments, $R^4$ is phenylethyl.

In accordance with certain preferred embodiments, $R^1$ is selected from the following:

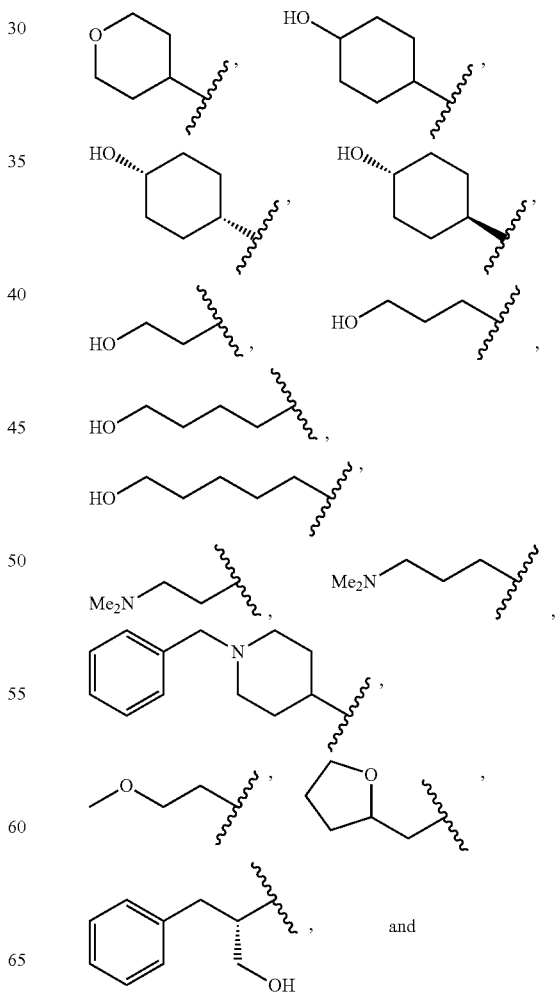

In accordance with certain embodiments, $R^4$ is 4-methoxybenzyl.

In accordance with certain preferred embodiments, $R^1$ is selected from the following:

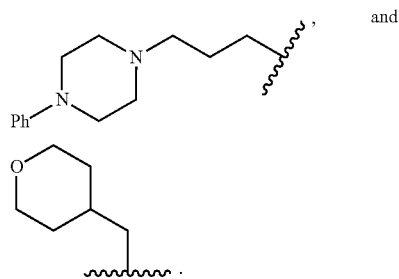

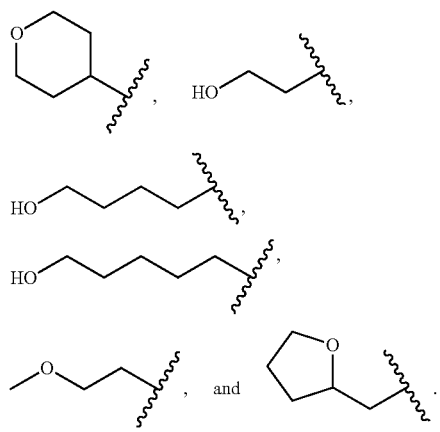

In accordance with certain specific embodiments, $R^2$ is phenyl, $R^3$ is phenyl, $R^4$ is 4-methoxybenzyl, and $R^1$ is selected from the following:

-continued

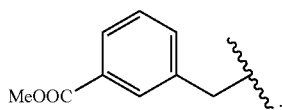

In accordance with certain specific embodiments, $R^2$ is phenyl, $R^3$ is phenyl, $R^4$ is phenylethyl, and $R^1$ is selected from the following:

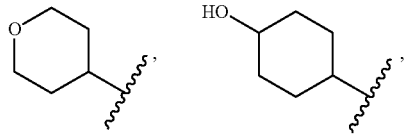

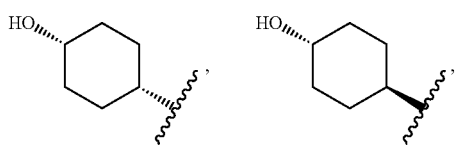

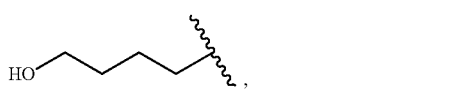

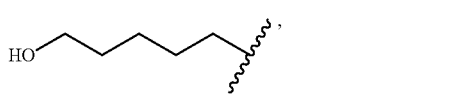

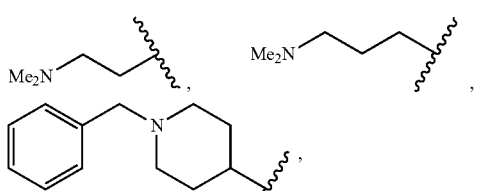

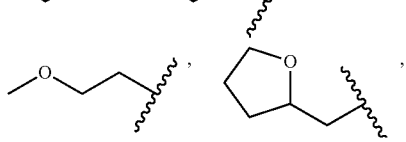

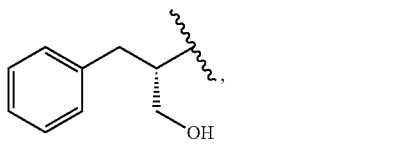

-continued

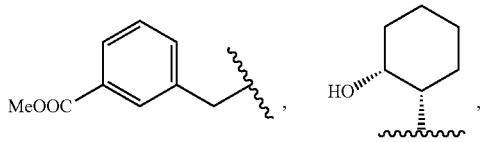

and

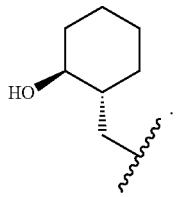

In accordance with certain embodiments, $R^4$ is heteroaryl $C_1$-$C_6$ alkyl.

In accordance with certain embodiments, $R^4$ is

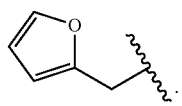

In accordance with certain preferred embodiments, $R^1$ is selected from the following:

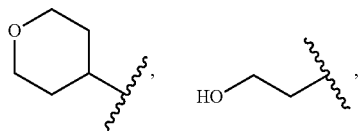

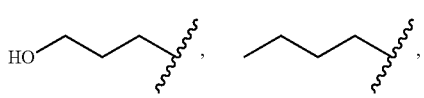

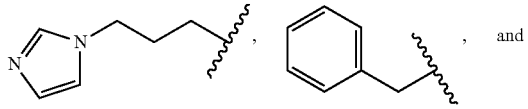, and

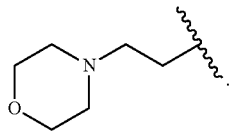

In accordance with certain specific embodiments, $R^2$ is phenyl, $R^3$ is phenyl, $R^4$ is

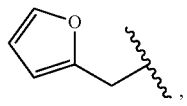

and $R^1$ is selected from the following:

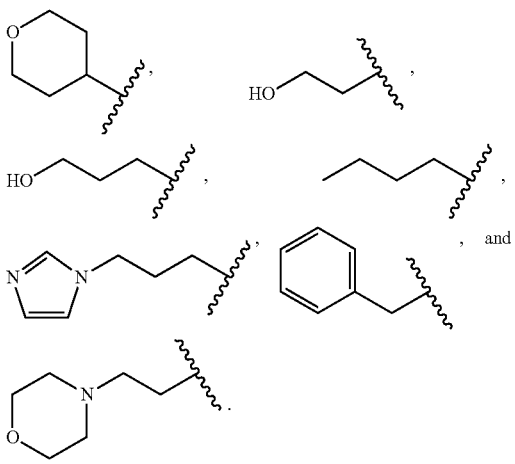

In accordance with certain embodiments, $R^4$ is selected from 4-aminosulfonylbenzyl, 4-trifluoromethoxybenzyl, 4-methoxybenzyl, and cyclopropylmethyl.

In accordance with certain preferred embodiments, $R^1$ is selected from the following:

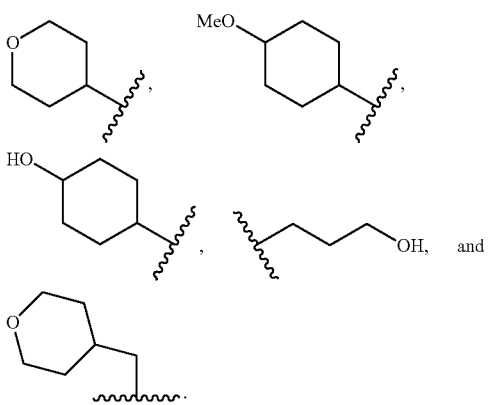

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "alkenyl," as used herein, means a linear alkenyl substituent containing at least one carbon-carbon double bond and from, for example, about 2 to about 6 carbon atoms (branched alkenyls are about 3 to about 6 carbons atoms), preferably from about 2 to about 5 carbon atoms (branched alkenyls are preferably from about 3 to about 5 carbon atoms), more preferably from about 3 to about 4 carbon atoms. Examples of such substituents include vinyl, propenyl, isopropenyl, n-butenyl, sec-butenyl, isobutenyl, tert-butenyl, pentenyl, isopentenyl, hexenyl, and the like.

The term "alkynyl," as used herein, means a linear alkynyl substituent containing at least one carbon-carbon triple bond and from, for example, 2 to about 6 carbon atoms (branched alkynyls are about 3 to about 6 carbons atoms), preferably from 2 to about 5 carbon atoms (branched alky- nyls are preferably from about 3 to about 5 carbon atoms), more preferably from about 3 to about 4 carbon atoms. Examples of such substituents include ethynyl, propynyl, isopropynyl, n-butynyl, sec-butynyl, isobutynyl, tert-butynyl, pentynyl, isopentynyl, hexynyl, and the like.

The term "cycloalkyl," as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups such as methyl groups, ethyl groups, and the like. The term "cycloalkylalkyl," as used herein, refers to an alkyl group linked to a cycloalkyl group and further linked to a molecule via the alkyl group.

The term "heterocyclyl," as used herein, refers to a monocyclic or bicyclic 5- or 6-membered ring system containing one or more heteroatoms selected from the group consisting of O, N, S, and combinations thereof. The heterocyclyl group can be any suitable heterocyclyl group and can be an aliphatic heterocyclyl group, an aromatic heterocyclyl group, or a combination thereof. The heterocyclyl group can be a monocyclic heterocyclyl group or a bicyclic heterocyclyl group. Suitable bicyclic heterocyclyl groups include monocyclic heterocyclyl rings fused to a $C_6$-$C_{10}$ aryl ring. When the heterocyclyl group is a bicyclic heterocyclyl group, both ring systems can be aliphatic or aromatic, or one ring system can be aromatic and the other ring system can be aliphatic as in, for example, dihydrobenzofuran. Non-limiting examples of suitable aromatic heterocyclyl groups include tetrahydrofuranyl, tetrahydropyranyl, tetrahydrothiophenyl, pyrrolidinyl, piperidinyl, and morpholinyl. Non-limiting examples of suitable aromatic heterocyclyl groups include furanyl; thiopheneyl; pyrrolyl; pyrazolyl; imidazolyl; 1,2,3-triazolyl; 1,2,4-triazolyl; isoxazolyl; oxazolyl; isothiazolyl; thiazolyl; 1,3,4-oxadiazol-2-yl; 1,2,4-oxadiazol-2-yl; 5-methyl-1,3,4-oxadiazole; 3-methyl-1,2,4-oxadiazole; pyridinyl; pyrimidinyl; pyrazinyl; triazinyl; benzofuranyl; benzothiopheneyl; indolyl; quinolinyl; isoquinolinyl; benzimidazolyl; benzoxazolinyl; benzothiazolinyl; and quinazolinyl. The heterocyclyl group is optionally substituted with 1, 2, 3, 4, or 5 substituents as recited herein such as with alkyl groups such as methyl groups, ethyl groups, and the like, or with aryl groups such as phenyl groups, naphthyl groups and the like, wherein the aryl groups can be further substituted with, for example halo, dihaloalkyl, trihaloalkyl, nitro, hydroxy, alkoxy, aryloxy, amino, substituted amino, alkylcarbonyl, alkoxycarbonyl, arylcarbonyl, aryloxycarbonyl, thio, alkylthio, arylthio, and the like, wherein the optional substituent can be present at any open position on the heterocyclyl group.

The term "heterocyclylalkyl," as used herein, refers to an alkyl group linked to a heterocyclyl group and further linked to a molecule via the alkyl group.

The term "arylalkyl," as used herein, refers to an alkyl group linked to a $C_6$-$C_{10}$ aryl ring and further linked to a molecule via the alkyl group. The term "alkylaryl," as used herein, refers to a $C_6$-$C_{10}$ aryl ring linked to an alkyl group and further linked to a molecule via the aryl group.

The term "alkylcarbonyl," as used herein, refers to an alkyl group linked to a carbonyl group and further linked to a molecule via the carbonyl group, such as alkyl-C(=O)—.

The term "alkoxycarbonyl," as used herein, refers to an alkoxy group linked to a carbonyl group and further linked to a molecule via the carbonyl group, such as alkyl-O—C(=O)—.

Whenever a range of the number of atoms in a structure is indicated (such as a $C_1$-$C_{12}$, $C_1$-$C_8$, $C_1$-$C_6$, $C_1$-$C_4$, or $C_2$-$C_{12}$, $C_2$-$C_8$, $C_2$-$C_6$, $C_2$-$C_4$ alkyl, alkenyl, alkynyl, etc.), it is specifically contemplated that any sub-range or individual number of carbon atoms falling within the indicated range also can be used. Thus, for instance, the recitation of a range of 1-8 carbon atoms (such as $C_1$-$C_8$), 1-6 carbon atoms (such as $C_1$-$C_6$), 1-4 carbon atoms (such as $C_1$-$C_4$), 1-3 carbon atoms (such as $C_1$-$C_3$), or 2-8 carbon atoms (such as $C_2$-$C_8$) as used with respect to any chemical group (such as alkyl, alkylamino, etc.) referenced herein encompasses and specifically describes 1, 2, 3, 4, 5, 6, 7, 8, 9, 10, 11, or 12 carbon atoms, and combinations thereof, as appropriate, as well as any sub-range thereof (such as 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate). Similarly, the recitation of a range of 6-10 carbon atoms (such as, $C_6$-$C_{10}$) as used with respect to any chemical group (such as, aryl) referenced herein encompasses and specifically describes 6, 7, 8, 9, and/or 10 carbon atoms, as appropriate, as well as any sub-range thereof (such as, 6-10 carbon atoms, 6-9 carbon atoms, 6-8 carbon atoms, 6-7 carbon atoms, 7-10 carbon atoms, 7-9 carbon atoms, 7-8 carbon atoms, 8-10 carbon atoms, and/or 8-9 carbon atoms, etc., as appropriate).

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2 π electrons, according to Hückel's Rule.

The phrase "pharmaceutically acceptable salt" is intended to include non-toxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media such as ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p. 1445, and *Journal of Pharmaceutical Science*, 66, 2-19 (1977).

Suitable bases include inorganic bases such as alkali and alkaline earth metal bases, such as those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (such as a dimethylaminoalkyl group) include hydrochloride and hydrobromide salts. The compounds of the present invention containing an acidic or basic moiety are useful in the form of the free base or acid or in the form of a pharmaceutically acceptable salt thereof.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

In any of the above embodiments, the compound or salt of formula (I) can have at least one asymmetric carbon atom. When the compound or salt has at least one asymmetric carbon atom, the compound or salt can exist in the racemic form, in the form of its pure optical isomers, or in the form of a mixture wherein one isomer is enriched relative to the other. In particular, in accordance with the present invention, when the inventive compounds have a single asymmetric carbon atom, the inventive compounds may exist as racemates, that is as mixtures of equal amounts of optical isomers, that is equal amounts of two enantiomers, or in the form of a single enantiomer. As used herein, "single enantiomer" is intended to include a compound that comprises more than 50% of a single enantiomer (that is enantiomeric excess up to 100% pure enantiomer).

When the compound or salt has more than one chiral center, the compound or salt can therefore exist as a mixture of diasteromers or in the form of a single diastereomer. As used herein, "single diastereomer" is intended to mean a compound that comprises more than 50% of a single diastereomer (that is diastereomeric excess to 100% pure diastereomer).

Synthetic Method

A general synthesis of embodiments of the compounds of the invention is depicted in Scheme 1. The synthesis of the compound 104 commences with reaction of alpha hydroxyketone 100 with a primary amine in the presence of catalytic zinc chloride to give the alpha aminoketone 101, which is not isolated but reacts directly with malononitrile to give aminopyrrole 102. Reaction of aminopyrrole 102 with triethyl orthoformate gives the imidate 103. Reaction of imidate 103 with primary amine $R^1NH_2$ in a solvent such as methanol provides final product 104.

Scheme 1

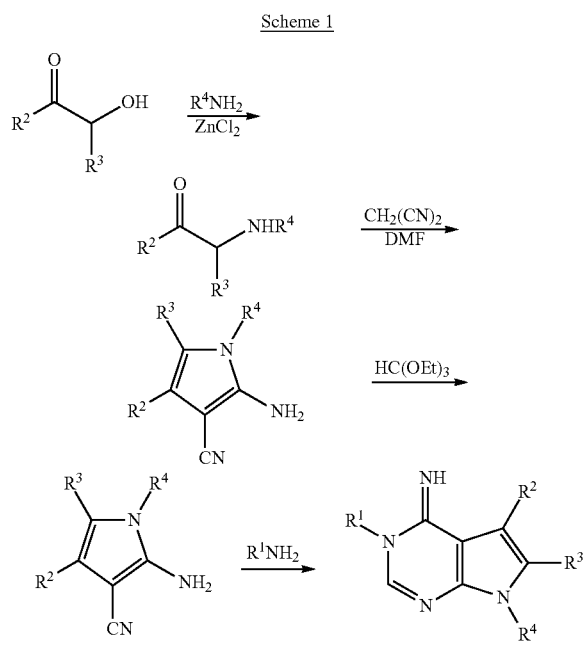

The present invention is further directed to a pharmaceutical composition comprising a pharmaceutically acceptable carrier and at least one compound or salt described herein.

It is preferred that the pharmaceutically acceptable carrier be one that is chemically inert to the active compounds and one that has no detrimental side effects or toxicity under the conditions of use.

The choice of carrier will be determined in part by the particular compound of the present invention chosen, as well as by the particular method used to administer the composition. Accordingly, there is a wide variety of suitable formulations of the pharmaceutical composition of the present invention. The following formulations for oral, aerosol, nasal, pulmonary, parenteral, subcutaneous, intravenous, intramuscular, intraperitoneal, intrathecal, intratumoral, topical, rectal, and vaginal administration are merely exemplary and are in no way limiting.

The pharmaceutical composition can be administered parenterally, such as intravenously, subcutaneously, intradermally, or intramuscularly. Thus, the invention provides compositions for parenteral administration that comprise a solution or suspension of the inventive compound or salt dissolved or suspended in an acceptable carrier suitable for parenteral administration, including aqueous and non-aqueous isotonic sterile injection solutions. Overall, the requirements for effective pharmaceutical carriers for parenteral compositions are well known to those of ordinary skill in the art. See, such as Banker and Chalmers, eds., *Pharmaceutics and Pharmacy Practice*, J. B. Lippincott Company, Philadelphia, pp. 238-250 (1982), and Toissel, *ASHP Handbook on Injectable Drugs*, 4th ed., pp. 622-630 (1986). Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound or salt of the present invention may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-beta-aminopropionates, and 2-alkyl-imidazoline quaternary ammonium salts, and (e) mixtures thereof.

The parenteral formulations can contain preservatives and buffers. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral.

The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

Formulations suitable for oral administration can consist of (a) liquid solutions, such as a therapeutically effective amount of the inventive compound dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compound or salt of the present invention, alone or in combination with other suitable components, can be made into aerosol formulations to be administered via inhalation. The compounds are preferably supplied in finely divided form along with a surfactant and propellant. Typical percentages of active compound are 0.01%-20% by weight, preferably 1%-10%. The surfactant must, of course, be nontoxic, and preferably soluble in the propellant. Representative of such surfactants are the esters or partial esters of fatty acids containing from 6 to 22 carbon atoms, such as caproic, octanoic, laurie, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included as desired, such as lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the compound or salt of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

It will be appreciated by one of ordinary skill in the art that, in addition to the aforedescribed pharmaceutical compositions, the compound or salt of the present invention may be formulated as inclusion complexes, such as cyclodextrin inclusion complexes, or liposomes. Liposomes serve to target the compounds to a particular tissue, such as lymphoid tissue or cancerous hepatic cells. Liposomes can also be used to increase the half-life of the inventive compound. Liposomes useful in the present invention include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired inventive compound or salt thereof, can be directed to the site of a specific tissue type, hepatic cells, for example, where the liposomes then deliver the selected compositions. Liposomes for use in the invention are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., *Ann. Rev. Biophys. Bioeng.*, 9, 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing a compound or salt of the present invention may be administered intravenously, locally, topically, etc. in a dose that varies according to the mode of administration, the agent being delivered, and the stage of disease being treated.

The perinucleolar compartment (PNC) is a subnuclear body dynamic structure, highly enriched in RNA-binding proteins and pol III RNA, which has been associated with malignancy both in vitro and in vivo. In addition, its presence positively correlates with metastatic capacity, making it a potential marker for cancer development and prognosis vivo (Pollock, C. et al., *Cold Spring Harb Perspect Biol.*, 2010; 2(2), 1-10; Slusarczyk, A. et al., *Cold Spring Harb Symp Quant Biol.* 2010, 75, 599-605).

Although the precise function of the PNC remains to be identified, PNC formation is closely associated with the metastatic phenotype. Notably, solid tumor cell lines seem to have a higher PNC population. A striking observation is the difference in PNC population between metastatically transformed cell lines and their parental counterparts. This observation particularly holds for the PC-3M cell line that was created by removing and culturing a metastatic lesion after implantation of the human prostrate tumor PC-3 cell line in nude mice. PNC prevalence (the percentage of cells with at least one PNC) increases in parallel with disease progression (staging and grading) for breast, ovarian, and colorectal cancers and reaches near 100% in distant metastases. A high PNC prevalence in early stage of breast cancer associates with poor patient outcomes (Kamath, R. V. et al., *Cancer Res.,* 2005, 65(1), 246-53). In addition, PNC prevalence directly correlates with the levels of metastatic capacity in mouse metastasis models of human cancer cells.

PNCs are not associated with traits that are common in both cancer and normal cells, such as proliferation, glycolysis, and differentiation states. The selective association with metastasis makes PNC an ideal and simple marker that reflects the complex trait of cellular malignancy. Thus, PNC reduction can be used as a phenotypic change to identify novel compounds that may not directly target the PNC structure itself, but induce desired changes that lead to the inhibition of cellular malignancy.

Previous studies have shown that classical antitumoral agents, such as topoisomearse I and II inhibitors, DNA cross linkers, a subset of nucleoside analogs, and methotrexate, cause reduction of PNC prevalence (Jin, Y. et al, *Chem Biol.,* 2002, 9, 157-62; Norton, J. T. et al., *Anti-Cancer Drugs.* 2008, 19(1), 23-36; Norton, J. T. et al., *J. Biol. Chem.* 2009, 284, 4090-4101). It has also been shown that the reduction of PNC by these agents is not a non-specific cytotoxic effect but a result of inhibition of the molecular target. This is exemplified by DNA alkylators, microtubule disrupting drugs, hydoxyurea and some nucleoside analogs which are cytotoxic agents that do not disrupt the PNC. Mechanistically it has also been suggested that those drugs which induce PNC reduction may be causing it via DNA damage. To that end, the DNA might serve as a locus for the nucleation of the PNC and this notion is also supported by the fact that the PNC is a heritable trait. However all the agents that are known to reduce PNC have known mechanisms of inducing cytotoxicity, making it difficult to separate an anti-metastatic effect from cell death.

The invention further provides a method for treating cancer. The method comprises administering an effective amount of the compound of the invention to an animal afflicted therewith. Preferably, the animal is a mammal. More preferably, the mammal is a human.

The term "mammal" includes, but is not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human. Furthermore, the subject can be the unborn offspring of any of the forgoing hosts, especially mammals (such as, humans), in which case any screening of the subject or cells of the subject, or administration of compounds to the subject or cells of the subject, can be performed in utero.

In accordance with an embodiment, the invention provides a method of treating or preventing cancer comprising administering to a patient in need thereof a therapeutically effective amount of a compound represented by Formula I, or a pharmaceutically acceptable salt thereof. The cancer can be any suitable cancer responsive to reduction of PNC prevalence, for example, cancers in which PNCs are prevalent.

In accordance with another embodiment, the invention provides a method of treating cancer. The cancer can be any suitable cancer. Preferably, the cancer is a metastatic cancer. For example, the cancer may be adrenocortical carcinoma, AIDS-related lymphoma, AIDS-related malignancies, anal cancer, cerebellar astrocytoma, extrahepatic bile duct cancer, bladder cancer, osteosarcoma/malignant fibrous histiocytoma, brain stem glioma, ependymoma, visual pathway and hypothalamic gliomas, breast cancer, bronchial adenomas/carcinoids, carcinoid tumors, gastrointestinal carcinoid tumors, carcinoma, adrenocortical, islet cell carcinoma, primary central nervous system lymphoma, cerebellar astrocytoma, cervical cancer, chronic lymphocytic leukemia, chronic myelogenous leukemia, clear cell sarcoma of tendon sheaths, colon cancer, colorectal cancer, cutaneous t-cell lymphoma, endometrial cancer, ependymoma, esophageal cancer, Ewing's sarcoma/family of tumors, extracranial germ cell tumors, extragonadal germ cell tumors, extrahepatic bile duct cancer, eye cancers, including intraocular melanoma, and retinoblastoma, gallbladder cancer, gastrointestinal carcinoid tumor, ovarian germ cell tumor, gestational trophoblastic tumor, hairy cell leukemia, head and neck cancer, Hodgkin's disease, hypopharyngeal cancer, hypothalamic and visual pathway glioma, intraocular melanoma, Kaposi's sarcoma, laryngeal cancer, acute lymphoblastic leukemia, acute myeloid leukemia, liver cancer, non-small cell lung cancer, small cell lung cancer, non-Hodgkin's lymphoma, Waldenstrom's macroglobulinemia, malignant mesothelioma, malignant thymoma, medulloblastoma, melanoma, intraocular melanoma, merkel cell carcinoma, metastatic squamous neck cancer with occult primary, multiple endocrine neoplasia syndrome, multiple myeloma/plasma cell neoplasm, mycosis fungoides, myelodysplastic syndrome, chronic myelogenous leukemia, myeloid leukemia, multiple myeloma, myeloproliferative disorders, nasal cavity and paranasal sinus cancer, nasopharyngeal cancer, neuroblastoma, oral cancer, oral cavity and lip cancer, oropharyngeal cancer, osteosarcoma/malignant fibrous histiocytoma of bone, ovarian cancer, ovarian low malignant potential tumor, pancreatic cancer, paranasal sinus and nasal cavity cancer, parathyroid cancer, penile cancer, pheochromocytoma, pituitary tumor, pleuropulmonary blastoma, prostate cancer, rectal cancer, renal cell (kidney) cancer, transitional cell cancer (such as renal pelvis and ureter), retinoblastoma, rhabdomyosarcoma, salivary gland cancer, malignant fibrous histiocytoma of bone, soft tissue sarcoma, sezary syndrome, skin cancer, small intestine cancer, stomach (gastric) cancer, supratentorial primitive neuroectodermal and pineal tumors, cutaneous T-cell lymphoma, testicular cancer, malignant thymoma, thyroid cancer, gestational trophoblastic tumor, urethral cancer, uterine sarcoma, vaginal cancer, vulvar cancer, and Wilms' tumor.

In any of the embodiments of the invention, the cancer can be any cancer in any organ, for example, a cancer is selected from the group consisting of brain carcinoma, glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof.

In an embodiment, the metastatic cancer is selected from the group consisting of breast cancer, ovarian cancer, colorectal cancer, brain cancer, and prostate cancer.

In accordance with other embodiments, the invention provides a method of potentiating or enhancing anticancer activity of an anticancer agent, the method comprising coadministering to a patient in need thereof an effective amount of an anticancer agent and a compound or salt of the invention. The anticancer agent can be chosen from reversible DNA binders, DNA alkylators, and DNA strand breakers.

Examples of suitable reversible DNA binders include topetecan hydrochloride, irinotecan (CPT11—Camptosar), rubitecan, exatecan, nalidixic acid, TAS-103, etoposide, acridines (such as arnsacrine, aminocrine), actinomycins (such as actinomycin D), anthracyclines (such as doxorubicin, daunorubicin), benzophenainse, XR 11576/MLN 576, benzopyridoindoles, Mitoxantrone, AQ4, Etopside, Teniposide, (epipodophyllotoxins), and bisintercalating agents such as triostin A and echinomycin.

Examples of suitable DNA alkylators include sulfur mustard, the nitrogen mustards (such as mechlorethamine), chlorambucil, melphalan, ethyleneimines (such as triethylenemelamine, carboquone, diaziquone), methyl methanesulfonate, busulfan, CC-1065, duocarmycins (such as duocarmycin A, duocarmycin SA), metabolically activated alkylating agents such as nitrosoureas (such as carmustine, lomustine, (2-chloroethyl)nitrosoureas), triazne antitumor drugs such as triazenoimidazole (such as dacarbazine), mitomycin C, leinamycin, and the like.

Examples of suitable DNA strand breakers include doxorubicin and daunorubicin (which are also reversible DNA binders), other anthracyclines, bleomycins, tirapazamine, enediyne antitumor antibiotics such as neocarzinostatin, esperamicins, calicheamicins, dynemicin A, hedarcidin, C-1027, N1999A2, esperamicins, zinostatin, and the like.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. Treatment of cancer can be evidenced, for example, by a reduction in tumor size, a reduction in tumor burden, a reduction in clinical symptoms resulting from the cancer, increase in longevity, increase in tumor free survival time, and the like. Treating in embodiments, can include inhibiting the development or progression of a cancer or metastatic cancer.

By the term "coadminister" is meant that each of the at least two compounds be administered during a time frame wherein the respective periods of biological activity overlap. Thus, the term includes sequential as well as coextensive administration of two or more drug compounds. The compounds can be administered simultaneously, separately (chronologically staggered), cyclically, or sequentially and in any order, such as before or after.

One skilled in the art will appreciate that suitable methods of utilizing a compound and administering it to a human for the treatment or prevention of disease states, in particular, cancer, which would be useful in the method of the present invention, are available. Although more than one route can be used to administer a particular compound, a particular route can provide a more immediate and more effective reaction than another route. Accordingly, the described methods are merely exemplary and are in no way limiting.

The dose administered to a mammal, particularly, a human, in accordance with the present invention should be sufficient to effect the desired response. Such responses include reversal or prevention of the adverse effects of the disease for which treatment is desired or to elicit the desired benefit. One skilled in the art will recognize that dosage will depend upon a variety of factors, including the age, condition, and body weight of the human, as well as the source, particular type of the disease, and extent of the disease in the human. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states may require prolonged treatment involving multiple administrations.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 to about 300 mg of one or more of the compounds described above per kg body weight of the animal or mammal.

The therapeutically effective amount of the compound or compounds administered can vary depending upon the desired effects and the factors noted above. Typically, dosages will be between 0.01 mg/kg and 250 mg/kg of the subject's body weight, and more typically between about 0.05 mg/kg and 100 mg/kg, such as from about 0.2 to about 80 mg/kg, from about 5 to about 40 mg/kg or from about 10 to about 30 mg/kg of the subject's body weight. Thus, unit dosage forms can be formulated based upon the suitable ranges recited above and the subject's body weight. The term "unit dosage form" as used herein refers to a physically discrete unit of therapeutic agent appropriate for the subject to be treated.

Alternatively, dosages are calculated based on body surface area and from about 1 mg/m$^2$ to about 200 mg/m$^2$, such as from about 5 mg/m$^2$ to about 100 mg/m$^2$ will be administered to the subject per day. In particular embodiments, administration of the therapeutically effective amount of the compound or compounds involves administering to the subject from about 5 mg/m$^2$ to about 50 mg/m$^2$, such as from about 10 mg/m$^2$ to about 40 mg/m$^2$ per day. It is currently believed that a single dosage of the compound or compounds is suitable, however a therapeutically effective dosage can be supplied over an extended period of time or in multiple doses per day. Thus, unit dosage forms also can be calculated using a subject's body surface area based on the suitable ranges recited above and the desired dosing schedule.

In accordance with other embodiments, the invention provides a method of potentiating or enhancing anticancer activity of radiation treatment, the method comprising coadministering to a patient in need thereof an effective amount of a radiation treatment and a compound or salt of the invention. The radiation treatment can be any suitable radiation treatment used in the treatment of cancers.

The invention further provides a use of a compound or salt of the invention in the manufacture of a medicament for treating or preventing cancer. The medicament typically is a pharmaceutical composition as described herein.

The following examples further illustrate the invention but, of course, should not be construed as in any way limiting its scope.

EXAMPLES

General Chemistry. Reagents and solvents used were commercial anhydrous grade and used without further purification. Column chromatography was carried out over silica gel (100-200 mesh). $^1$H NMR spectra were recorded with a Bruker 400 MHz spectrometer from solutions in CDCl$_3$ and DMSO-d6. Chemical shifts in $^1$H NMR spectra are reported in parts per million (ppm, δ) downfield from the internal standard Me$_4$Si (TMS, δ=0 ppm). Chemical shifts in $^{13}$C NMR spectra are reported in parts per million (ppm, δ) calibrated from residual CHCl$_3$ (δ=77.0 ppm) signal and are reported using an API pulse sequence displaying methyl and methine (CH$_3$ and CH) signals as down and quaternary and methylene (C and CH$_2$) signals as up. Molecular weight confirmation was performed using an Agilent 6224 Time-Of-Flight Mass Spectrometer (TOF, Agilent Technologies, Santa Clara, Calif.). A 3 minute gradient from 5 to 100% Acetonitrile in water (0.03% formic acid) was used with a 5.1 minute run time at a flow rate of 0.4 mL/min. A Waters Atlantis T3 C18 column (1.8 micron, 2.1×50 mm) was used at a temperature of 25° C. Confirmation of molecular formula was confirmed using electrospray ionization in the positive mode with the Agilent Masshunter software (version B.02).

Example 1

This Example illustrates a procedure for the synthesis of 2-Amino-1-benzyl-4,5-diphenyl-1H-pyrrole-3-carbonitrile A, an intermediate in the synthesis of a compound in accordance with an embodiment of the invention.

A modified Voigt reaction/Knoevenagel condensation sequence was carried out using the procedure described in Roth, H. J. et al., *Arch. Pharmaz.* 1975, 308, 179-185. Benzoin (2.19 g, 10.3 mmol), benzylamine (1.66 g, 15.5 mmol, 1.5 equiv.), and zinc chloride (0.10 g, 0.73 mmol, 0.07 equiv.) were heated at reflux for 3 hours and the mixture was removed from the oil bath. To the still warm mixture was added malononitrile (1.35 g, 20.64 mmol, 2.0 equiv.) in DMF (3 mL). The reaction mixture was allowed to cool to room temperature and stirred for 16 hrs, affording the crude pyrrole as a dark brown solid. The solid was partitioned between water and CH$_2$Cl$_2$ and the aqueous extracted with additional CH$_2$Cl$_2$ (2×50 mL). The combined organics were dried with Na$_2$SO$_4$ and the solvent removed in vacuo to afford the previously reported pyrrole product A as a light brown solid (1.67 g, 4.78 mmol, 46% yield), which was used without further purification. R=0.22 (20% EtOAc in hexanes); $^1$H NMR δ 4.91 (s, 2H), 7.06-7.37 (complex, 15H); $^{13}$C NMR δ d (CH, CH$_3$) 125.8 (×2), 126.3, 127.9, 128.1, 128.2 (×2), 128.6 (×2), 128.7 (×2), 129.2 (×2), 131.0; u (C, CH$_2$) 46.9, 117.5, 120.9, 125.6, 130.8, 133.1, 136.0, 146.0, 162.5; IR 3329, 3228, 3031, 2195, 1663, 1556 cm$^{-1}$; HRMS calcd for C$_{24}$H$_{20}$N$_3$ [M+H$^+$] 350.1657, found 350.1648.

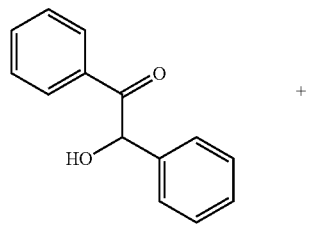

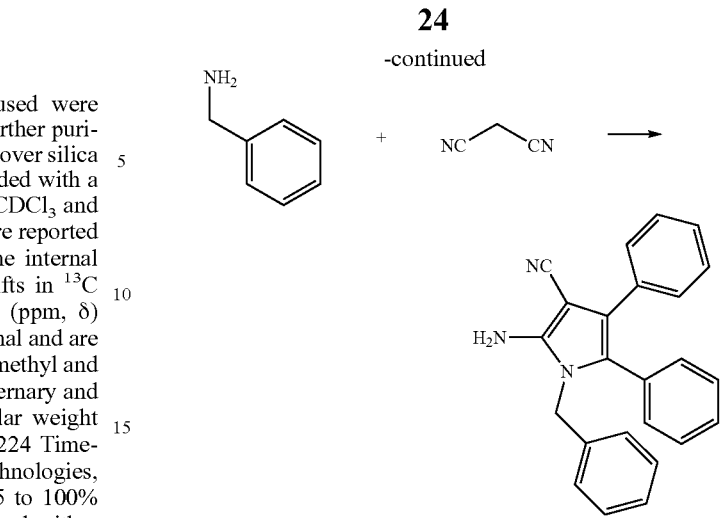

Example 2

This Example illustrates a procedure for the synthesis of (E)-Ethyl N-(1-benzyl-3-cyano-4,5-diphenyl-1H-pyrrol-2-yl)formimidate B, an intermediate in the synthesis of a compound in accordance with an embodiment of the invention.

2-Amino-1-benzyl-4,5-diphenyl-1H-pyrrole-3-carbonitrile A (1.07 g, 3.06 mmol) and triethylorthoformate (4.54 g, 30.6 mmol, 10 equiv.) were heated at 75° C. for 14 hrs and the excess triethylorthoformate was removed in vacuo. The residue was dissolved in a minimum of CH$_2$Cl$_2$, adsorbed onto celite, and chromatographed on silica to afford the formimidate product B as a tan solid (0.80 g, 1.97 mmol, 64% yield). R$_f$=0.47 (20%/EtOAc in hexanes); mp=154-156° C.; $^1$H NMR δ 1.30 (t, J=7.2 Hz, 3H), 4.27 (dq, J=0.8, 8.2 Hz, 2H), 5.05 (s, 2H), 6.86 (dd, J=2.0, 8.0 Hz, 2H), 7.06 (dd, J=1.6, 8.0 Hz, 2H), 7.14-7.29 (complex, 11H), 8.51 (s, 1H); $^{13}$C NMR δ d (CH, CH$_3$) 13.9, 126.4 (×2), 126.5, 127.2, 128.1 (×2), 128.2, 128.4 (×4), 129.0 (×2), 131.2 (×2), 158.3; u (C, CH$_2$) 46.9, 63.2, 117.9, 123.1, 128.5, 130.8, 132.8, 137.6, 143.9; IR 2208, 1627, 1605 cm$^{-1}$; HRMS calcd for C$_{27}$H$_{24}$N$_3$O [M+H$^+$] 406.1919, found 406.1915.

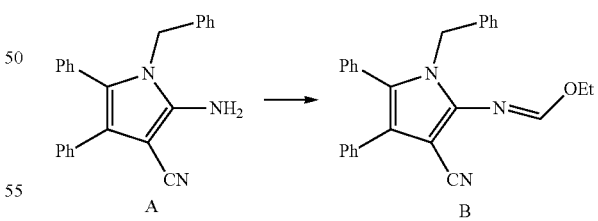

Example 3

This Example illustrates a synthesis of a compound in accordance with an embodiment of the invention, trans-4-(7-Benzyl-4-imino-5,6-diphenyl-4,7-dihydro-3H-pyrrolo[2,3-d]pyrimidin-3-yl)cyclohexanol 2.

A solution of the formimidate B (40 mg, 0.099 mmol) and trans-4-aminocyclohexanol hydrochloride (23 mg, 0.15 mmol, 1.5 equiv) in MeOH (1.5 mL) were heated in a reaction vial at 60° C. for 17 hrs then cooled to room temperature. Evaporation of the solvent and purification of the residue by mass-directed preparative reverse-phase HPLC afforded the pyrolopyrimidine product 2 as a tan solid (16 mg, 0.034 mmol, 34% yield). $R_f$=0.39 (1:1 acetone: $CH_2Cl_2$ with 1% $Et_3N$); mp=171-185° C.; $^1H$ NMR δ 1.66 (m, 4H), 2.13 (d, J=8.8 Hz, 4H), 3.70 (m, 1H), 5.14 (m, 1H), 5.28 (s, 2H), 6.45 (br s, 1H), 6.95 (m, 2H), 7.04 (d, J=6.8 Hz, 2H), 7.18-7.26 (complex, 11H), 7.80 (s, 1H); $^{13}C$ NMR δ d (CH, $CH_3$) 52.0, 69.7, 126.7 (×2), 126.9, 127.3, 128.0, 128.1 (×2), 128.3 (×2), 128.4 (×2), 130.5 (×2), 131.0 (×2), 142.3; u (C, $CH_2$) 30.6, 34.7, 46.0, 102.9, 118.1, 130.4, 133.2, 133.6, 137.7, 142.5, 155.1; IR 1625, 1604 $cm^{-1}$; HRMS calcd for $C_{31}H_{31}N_4O$ [M+H$^+$] 475.2498, found 475.2492.

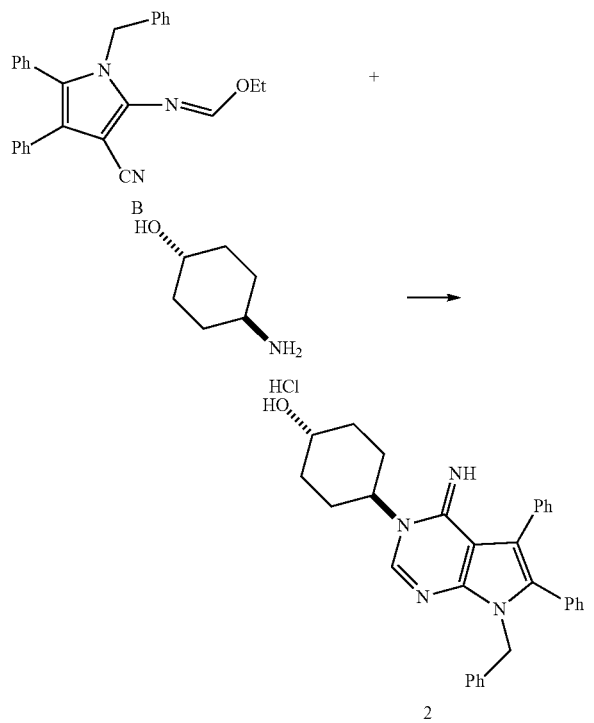

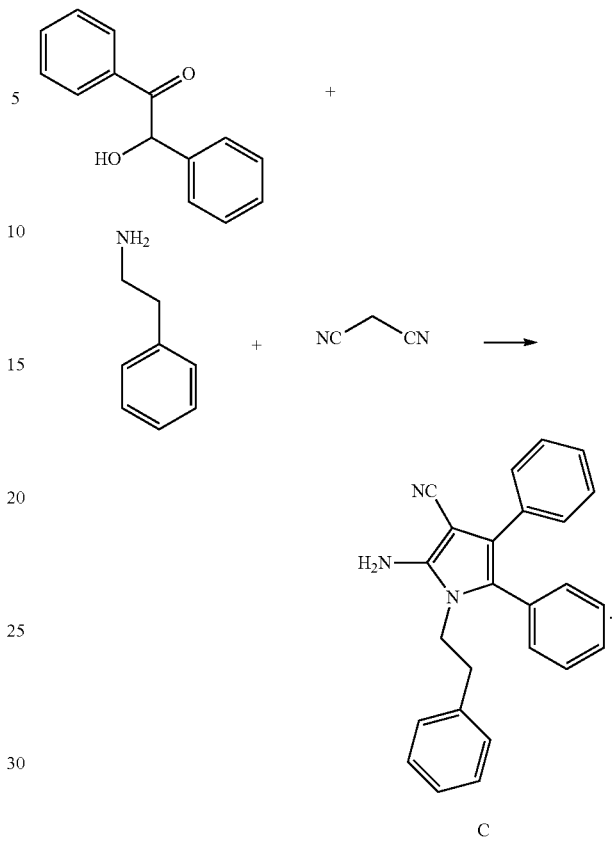

Example 4

This Example illustrates a procedure for the synthesis of 2-amino-1-phenethyl-4,5-diphenyl-1H-pyrrole-3-carbonitrile C, an intermediate in the synthesis of a compound in accordance with an embodiment of the invention.

Benzoin (4.35 g, 20.5 mmol), phenethylamine (3.73 g, 30.7 mmol), and zinc chloride (0.10 g, 0.73 mmol, 0.07 equiv.) were heated at reflux for 3 hours and the mixture was removed from the oil bath. To the still warm mixture malononitrile (2.71 g, 41.0 mmol, 2.0 equiv.) in DMF (3 mL) was added. The reaction mixture was allowed to cool to room temperature and stirred for 16 hrs, affording the crude pyrrole as a dark brown solid. The solid was partitioned between water and $CH_2Cl_2$ and the aqueous extracted with additional $CH_2Cl_2$ (2×50 mL.). The combined organics were dried with $Na_2SO_4$ and the solvent removed in vacuo to afford pyrrole product C (3.50 g, 9.63 mmol, 47% yield) as a light brown solid. $R_f$=0.13 (20% EtOAc in hexanes); mp=144-149° C.; IR 3330, 2199, 1634, 1601, 1502 $cm^{-1}$; HRMS calcd for $C_{25}H_{23}N_3$[M+H$^+$] 364.1814, found 364.1827.

Example 5

This example demonstrates a high content assay for PNC detection.

The quantitative output for this assay is the reduction of PNC prevalence. The PNC can be detected in living cells by the expression of a green fluorescent protein (GFP) tagged to the PNC localized protein, PTB. A PC3M cell line was used that stably expresses GFP-PTB to mark PNCs. This method eliminates the need for immunofluorescent staining. Previous studies demonstrate that the fusion proteins behave similarly to their endogenous counterparts: transient and stable over-expression of the fusion protein did not have detectable adverse effects on cell morphology or cell growth. After treatment, cells are fixed and the nuclei are counterstained with Hoechst 33342 dye; the cells are then ready for analysis.

The IN Cell Analyzer 1000 automated fluorescent imaging system (GE Healthcare, Piscataway, N.J.) was used for automated image acquisition. Images were acquired with a 20× objective using a 475/20 nm excitation filter, a 535/50 nm HQ emission filter, a QS05LP dichroic filter, and an exposure time of 100 to 150 ms (adjusted to obtain a dynamic range of ~200 to 1750), with no camera binning. The instrument acquired images of each well in a 1536-well plate with a laser-based autofocus system. To score PNC prevalence in a high-content throughput, the Multi-Target Analysis (MTA) algorithm (GE Healthcare, Investigator v3.5) to identify individual cells and granules (PNCs) within these cells was used. The nucleus was segmented via a region growing method (50 μm$^2$ minimum area) with light shading and noise removal to allow "touching" nuclei to be separated. Granules in the nucleus (PNCs) were segmented using a multiscale top hat method, which measures granules of 1 to 2 μm in size and used a smart masking method to identify the boundaries of each segmented granule. The algorithm was optimized and validated using positive and negative controls (50 μM camptothecin and DMSO, respectively). In particular, the MTA algorithm allows for the identification of multiple subcellular compartments and organelles (or granules) within those compartments. In this instance, the algorithm's capability to identify objects within the same color channel that only differ in size or fluorescent intensity was utilized. Also, the algorithm allows for building complex hierarchical classification systems, using output measures within the algorithm to filter and define subpopulations. For this particular assay, PNC-positive cells were scored when 1 to 3 PNC granules were detected per nucleus. Cells that contained 0 granules were scored as PNC negative, and cells with >3 granules were assumed to be false positives (very few cells have more than 3 PNCs in one focus plane), and were also scored as PNC negative. The assay was conducted using the sequence set forth in Table 1.

TABLE 1

| Sequence | Value | Parameter | Description |
| --- | --- | --- | --- |
| 1 | Cells | 5 μL | 750-1000 cells/well |
| 2 | Time | 4 hrs | Incubate at 37° C. and 5% $CO_2$ |
| 3 | Reagent | 23 nL | 0.5 nM to 58 μM final concentrations (in titration) |
| 4 | Time | 16 hrs | Incubate at 37° C. and 5% $CO_2$ |
| 5 | Reagent | 4 μL | Fixation step with 6% EM grade paraformaldehyde and 0.1% Triton X-100 |
| 6 | Time | 20 min | RT incubation |
| 7 | Wash | 5 μL | Liquid was aspirated and 5 μL of PBS was added |
| 8 | Wash | 5 μL | Liquid was aspirated and 5 μL of PBS was added |
| 9 | Reagent | 5 μL | Staining with PBS containing 1 μg/mL Hoechst 33342 |
| 10 | Detector | Fluorescence | IN Cell 1000, 20 × objective |

Example 6

This example demonstrates an adenosine triphosphate (ATP) quantitation assay.

This follow-up assay was conducted to measure the effect of compounds on cell health by measuring ATP levels (ATPLite™). ATPLite™ is an ATP monitoring system based on firefly (*Photinus pyralis*) luciferase. The level of ATP in a metabolically active cell is a general marker for its viability. ATP levels are often reduced during necrosis or apoptosis. In this assay, the luciferase enzyme catalyzes the conversion of the added substrate D-luciferin to oxyluciferin and light with ATP. Thus, the emitted light is proportional to the ATP concentration. For this assay, the highly metastatic PC3M reporter cell line stably expressing the PTB-GFP was provided by Professor Sui Huang of Northwestern University. The media and cell culture reagents were purchased from Invitrogen (Carlsbad, Calif.), ATPLite™ came from PerkinElmer. The assay was conducted using the sequence set forth in Table 2.

TABLE 2

| Sequence | Value | Parameter | Description |
| --- | --- | --- | --- |
| 1 | Cells | 5 μL | 2000 cells/well |
| 2 | Time | 4 hrs | Incubate at 37° C. and 5% $CO_2$ |
| 3 | Reagent | 23 nL | 0.5 nM to 58 μM final concentrations (in titration) |
| 4 | Time | 24 hrs | Incubate at 37° C. and 5% $CO_2$ |
| 5 | Reagent | 3 μL | ATPLite |
| 6 | Time | 20 min | RT incubation |
| 7 | Centrifuge | 1 min | 1500 RPM |
| 8 | Detector | Luminescence | ViewLux |

Example 7

This example demonstrates a tumor cell migration assay.

High-content tumor cell migration assays in 3-dimensional extracellular matrices are powerful tools for modeling and understanding the biology of this critical step in the process of metastasis. However, most of the available methods are not amenable to the throughput required by studies of comparative pharmacology or small scale screening. For this reason, compounds were tested in BellBrook Labs™ automated high-content tumor cell invasion assays. A standard screening-sized plate with an array of embedded microchannels was designed and constructed from common thermoplastics.

PC3M cells were tested for invasion through 3D fibrillar collagen in the Iuvo Single Microchannel Plate, in the presence of varying levels of test compounds. Channels were prefilled with 820 nL of 3-dimensional type I collagen at 1 mg/mL, through the input port. Following gelation, 2,000 PC3M cells were seeded into the output port using growth media (RPMI+10% FBS with antibiotics) in a volume of 5 μL. Cells were incubated in a 37° C. incubator inside a humidified container to control evaporation (Bioassay dish, Corning). Media, including test compounds, was changed daily for 5 days. At the end of the assay, cells were fixed and stained with Hoechst 33342, then imaged with 4× objective under epifluorescence. Under these conditions, cells across the 140 μm height range of the microchannel can be reliably identified. Test compounds were serially diluted by a factor of 3 to produce 10 concentrations ranging from 50 or 100 μM to 2.5 nM. All assays were conducted in the presence of 0.1% DMSO. Four replicates were performed for all test concentrations. Each plate had 4 dose response curves, as well as 16 channels with no compound and 16 channels with 50 μM blebbistatin (positive control). Analysis was done by automatically cropping each image at the right edge of the channel and counting cells via the 'count nuclei' function on Metamorph (Molecular Devices). Non-linear regression analysis was performed with GraphPad Prism. The results are set forth in Table 3.

TABLE 3

| Compound | PNC $AC_{50}$ (μM) | Invasion cell # $IC_{50}$ (μM) | Proliferation output port $IC_{50}$ (μM) | Comments |
| --- | --- | --- | --- | --- |
| 2 | 0.40 | 3.16 | 3.98 | embodiment |
| Control | inactive | 79.43 | 19.95 | Negative control |
| 1 | 0.09 | 3.16 | 5.01 | embodiment |

Example 8

This example demonstrates the effect of an embodiment of the invention on colony formation of PC3M cells.

Compound 2 was tested for its ability to affect anchorage independent growth in a soft agar assay, a stringent method to detect malignant transformation of cells in vitro. Compound 2 demonstrated a dose dependent reduction in the number of colonies after 14 days at very low concentrations (3.8, 18.6 nM), with no impact on cell viability. Thus, the compound exhibits potent inhibition of anchorage independent growth in PC3M cells.

Example 9

This example demonstrates biological activities of embodiments of the invention. The high content assay for PNC detection as described in Example 5 was used to provide the PNC $AC_{50}$ results. The ATP quantitation assay as described in Example 6 was used to provide the ATP $AC_{50}$ results. The results are set forth in Table 4.

TABLE 4

| Compound | Structure | PNC $IC_{50}$ (μM) | ATP $IC_{50}$ (μM) |
|---|---|---|---|
| 56 | 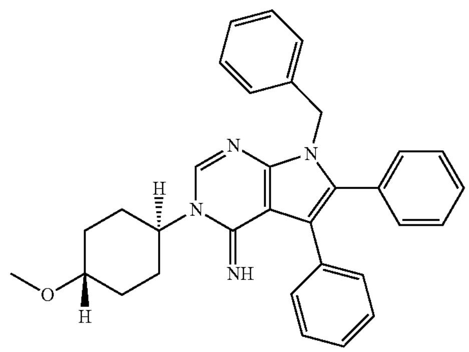 [SMILES: CO[C@H]1CC[C@H](n2cnc3c(c(-c4ccccc4)c(-c4ccccc4)n3Cc3ccccc3)c2=N)CC1] | 0.009 | 19.182 |
| 2 | 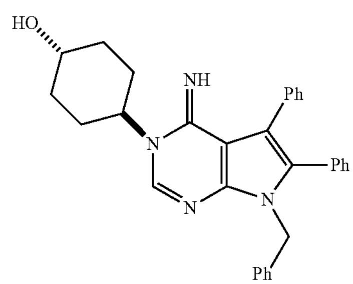 | 0.024 | 19.182 |
| 1 | 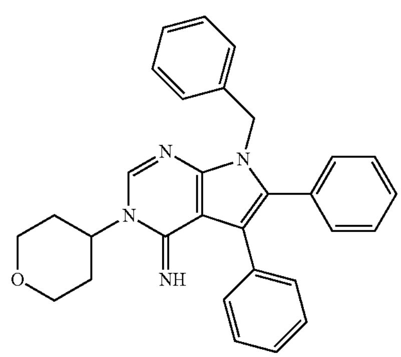 [SMILES: N=c1c2c(-c3ccccc3)c(-c3ccccc3)n(Cc3ccccc3)c2ncn1C1CCOCC1] | 0.030 | 152.369 |

TABLE 4-continued

| Compound | Structure | PNC IC$_{50}$ (μM) | ATP IC$_{50}$ (μM) |
|---|---|---|---|
| 3 | 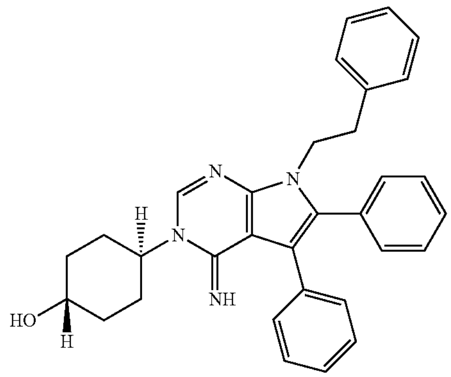 [SMILES: N=c1c2c(-c3ccccc3)c(-c3ccccc3)n(CCc3ccccc3)c2ncn1[C@H]1CC[C@H](O)CC1] | 0.047 | 9.614 |
| 57 | 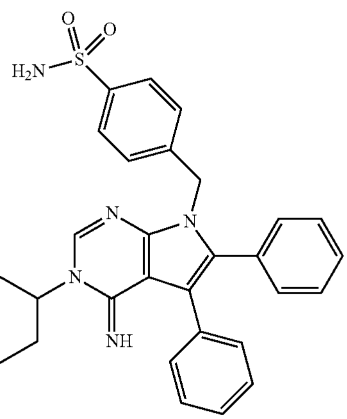 | 0.059 | 96.138 |
| 4 | 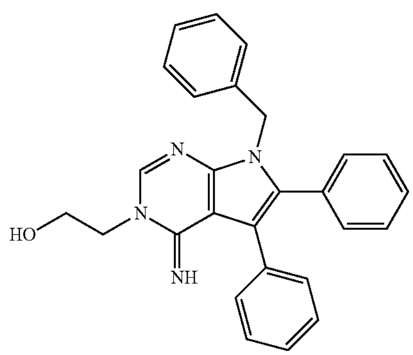 [SMILES: N=c1c2c(-c3ccccc3)c(-c3ccccc3)n(Cc3ccccc3)c2ncn1CCO] | 0.118 | 76.365 |
| 61 | 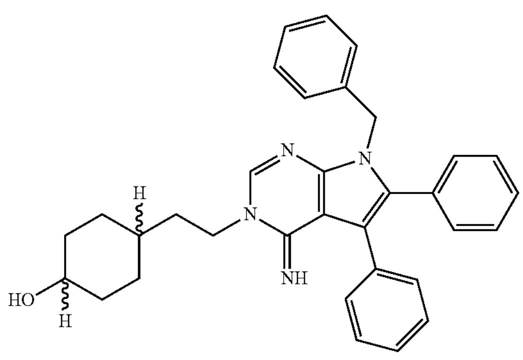 [SMILES: N=c1c2c(-c3ccccc3)c(-c3ccccc3)n(Cc3ccccc3)c2ncn1CCC1CCC(O)CC1] | 0.118 | 24.149 |

TABLE 4-continued
| Compound | Structure | PNC IC$_{50}$ (μM) | ATP IC$_{50}$ (μM) |
|---|---|---|---|
| 59 | 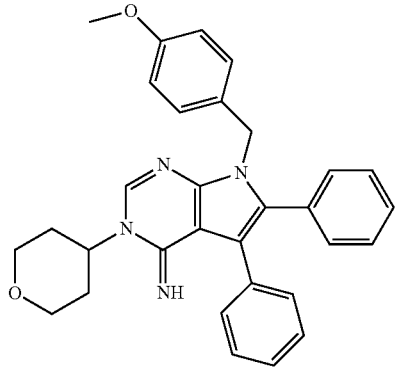 | 0.118 | 24.149 |
| 60 | 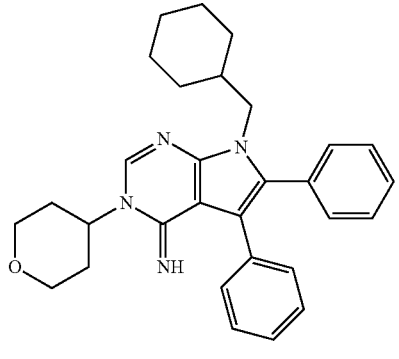 [SMILES: N=c1c2c(-c3ccccc3)c(-c3ccccc3)n(CC3CCCCC3)c2ncn1C1CCOCC1] | 0.118 | 24.149 |
| 58 | 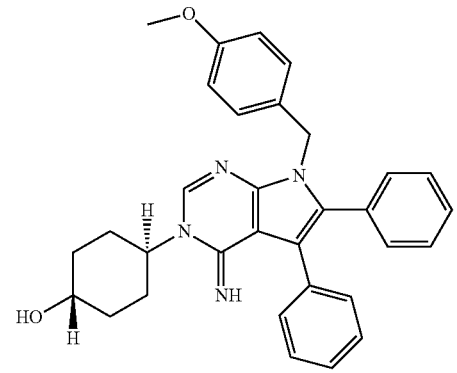 [SMILES: COc1ccc(Cn2c(-c3ccccc3)c(-c3ccccc3)c3c(=N)n([C@H]4CC[C@H](O)CC4)cnc32)cc1] | 0.118 | 24.149 |
| 9 | 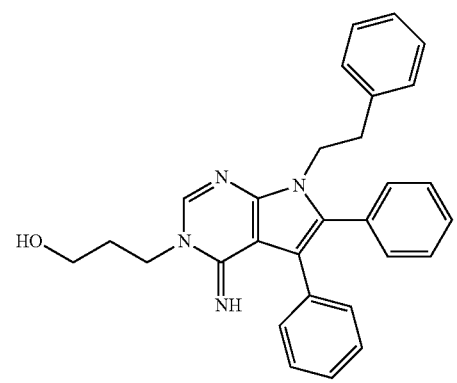 [SMILES: N=c1c2c(-c3ccccc3)c(-c3ccccc3)n(CCc3ccccc3)c2ncn1CCCO] | 0.148 | 19.182 |

TABLE 4-continued

| Compound | Structure | PNC IC$_{50}$ (μM) | ATP IC$_{50}$ (μM) |
|---|---|---|---|
| 63 | 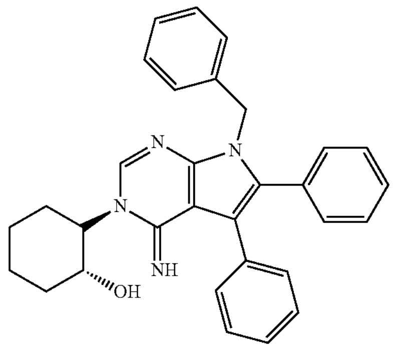 | 0.148 | 19.182 |
| 62 | 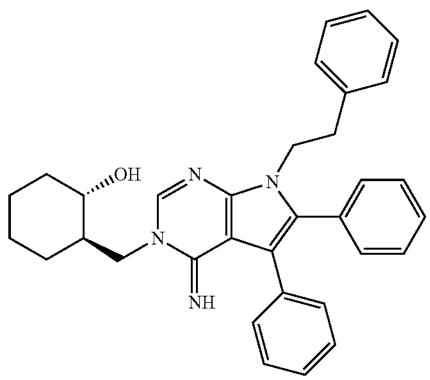 [SMILES: N=c1c2c(-c3ccccc3)c(-c3ccccc3)n(CCc3ccccc3)c2ncn1C[C@H]1CCCC[C@@H]1O] | 0.148 | 24.149 |
| 8 | 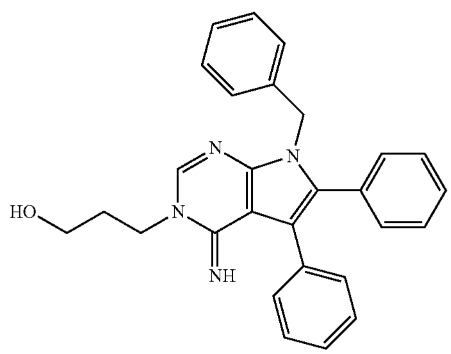 [SMILES: N=c1c2c(-c3ccccc3)c(-c3ccccc3)n(Cc3ccccc3)c2ncn1CCCO] | 0.148 | 24.149 |
| 5 | 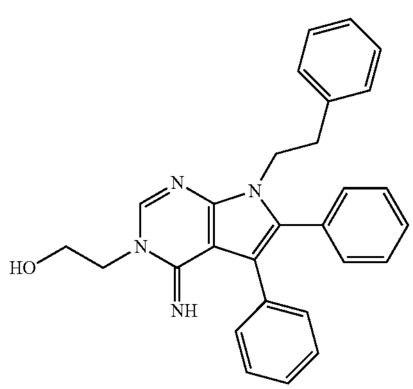 [SMILES: N=c1c2c(-c3ccccc3)c(-c3ccccc3)n(CCc3ccccc3)c2ncn1CCO] | 0.187 | 19.182 |

TABLE 4-continued

| Compound | Structure | PNC IC$_{50}$ (μM) | ATP IC$_{50}$ (μM) |
|---|---|---|---|
| 64 | 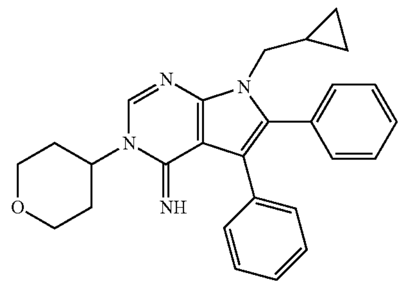 [SMILES: N=c1c2c(-c3ccccc3)c(-c3ccccc3)n(CC3CC3)c2ncn1C1CCOCC1] | 0.187 | 38.273 |
| 13 | 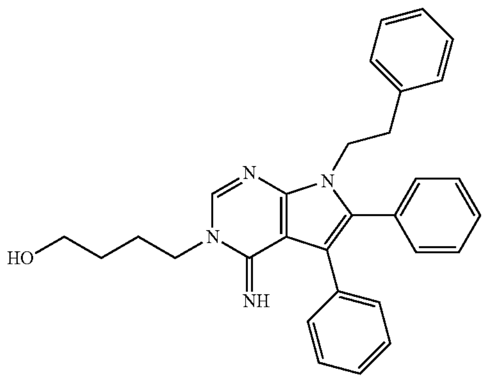 [SMILES: N=c1c2c(-c3ccccc3)c(-c3ccccc3)n(CCc3ccccc3)c2ncn1CCCCO] | 0.235 | 15.237 |
| 65 | 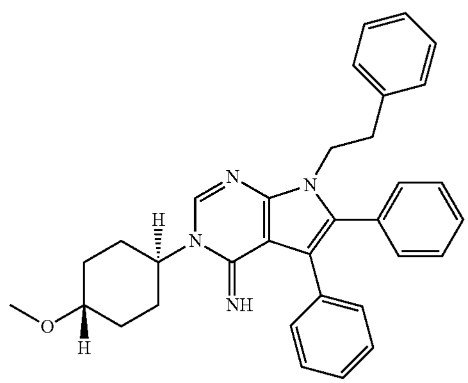 [SMILES: CO[C@H]1CC[C@H](n2cnc3c(c(-c4ccccc4)c(-c4ccccc4)n3CCc3ccccc3)c2=N)CC1] | 0.235 | 19.182 |
| 67 | 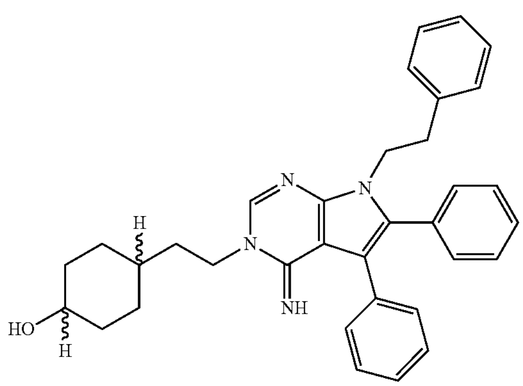 [SMILES: N=c1c2c(-c3ccccc3)c(-c3ccccc3)n(CCc3ccccc3)c2ncn1CCC1CCC(O)CC1] | 0.296 | 24.149 |

TABLE 4-continued

| Compound | Structure | PNC IC$_{50}$ (μM) | ATP IC$_{50}$ (μM) |
|---|---|---|---|
| 66 | 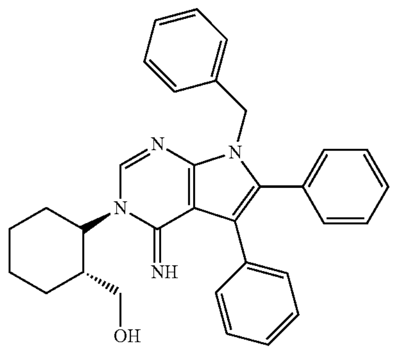 | 0.296 | 76.365 |
| 68 | 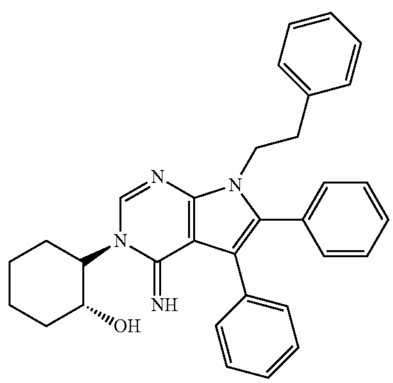 | 0.296 | 38.273 |
| 15 | 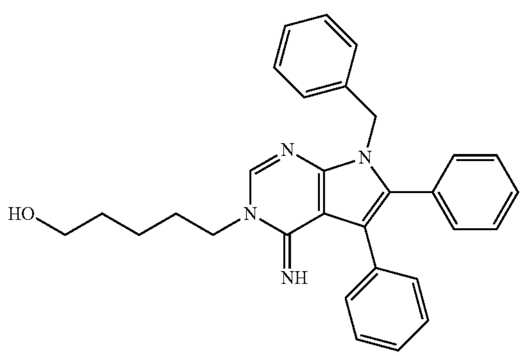 [SMILES: N=c1c2c(-c3ccccc3)c(-c3ccccc3)n(Cc3ccccc3)c2ncn1CCCCCO] | 0.372 | 24.149 |
| 71 | 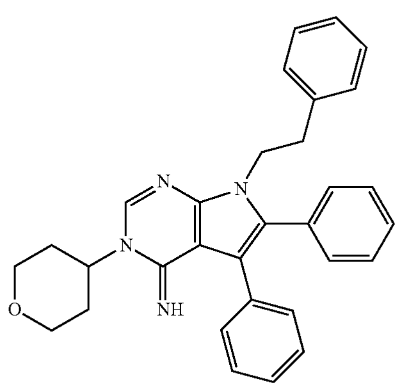 [SMILES: N=c1c2c(-c3ccccc3)c(-c3ccccc3)n(CCc3ccccc3)c2ncn1C1CCOCC1] | 0.372 | 121.031 |

TABLE 4-continued

| Compound | Structure | PNC IC$_{50}$ (μM) | ATP IC$_{50}$ (μM) |
|---|---|---|---|
| 70 | 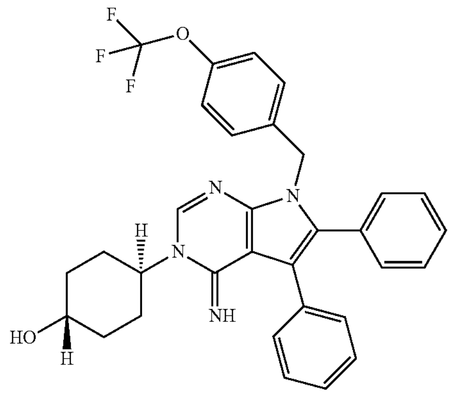 [SMILES: N=c1c2c(-c3ccccc3)c(-c3ccccc3)n(Cc3ccc(OC(F)(F)F)cc3)c2ncn1[C@H]1CC[C@H](O)CC1] | 0.372 | 24.149 |
| 69 | 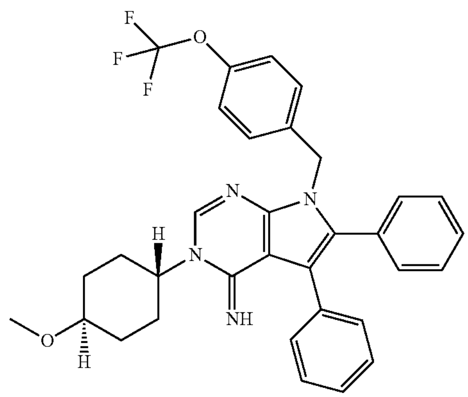 [SMILES: CO[C@H]1CC[C@H](n2cnc3c(c(-c4ccccc4)c(-c4ccccc4)n3Cc3ccc(OC(F)(F)F)cc3)c2=N)CC1] | 0.372 | 19.182 |
| 72 | 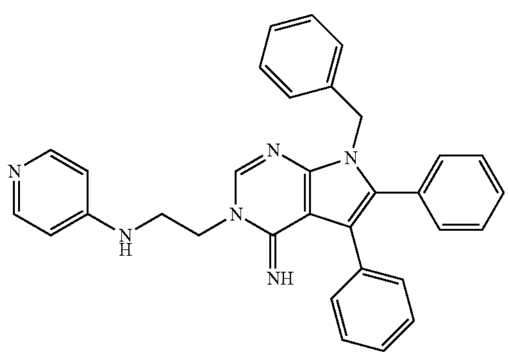 [SMILES: N=c1c2c(-c3ccccc3)c(-c3ccccc3)n(Cc3ccccc3)c2ncn1CCNc1ccncc1] | 0.469 | 24.149 |
| 20 | 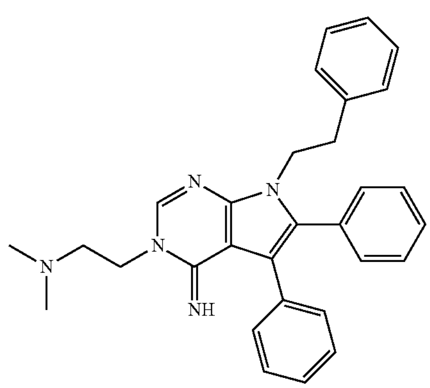 [SMILES: CN(C)CCn1cnc2c(c(-c3ccccc3)c(-c3ccccc3)n2CCc2ccccc2)c1=N] | 0.469 | 96.138 |

TABLE 4-continued
| Compound | Structure | PNC IC$_{50}$ (μM) | ATP IC$_{50}$ (μM) |
|---|---|---|---|
| 16 | 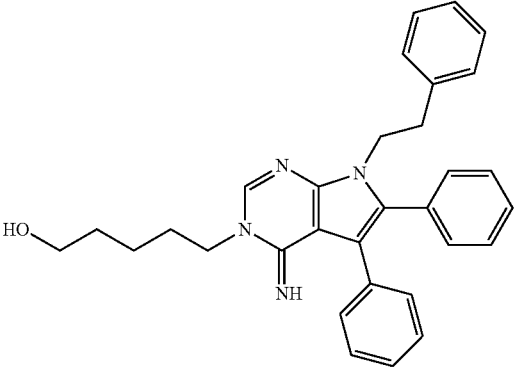 [SMILES: N=c1c2c(-c3ccccc3)c(-c3ccccc3)n(CCc3ccccc3)c2ncn1CCCCCO] | 0.590 | 38.273 |
| 73 | 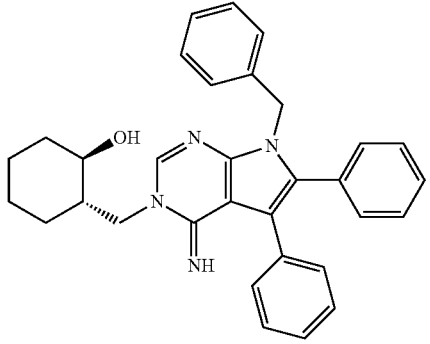 [SMILES: N=c1c2c(-c3ccccc3)c(-c3ccccc3)n(Cc3ccccc3)c2ncn1C[C@@H]1CCCC[C@H]1O] | 0.590 | 24.149 |
| 7 | 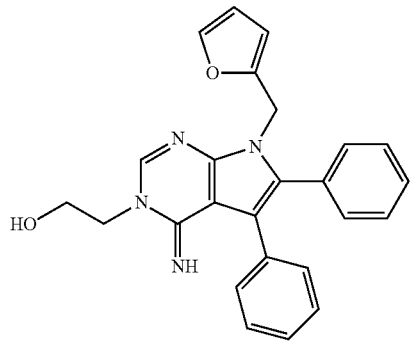 [SMILES: N=c1c2c(-c3ccccc3)c(-c3ccccc3)n(Cc3ccco3)c2ncn1CCO] | 0.628 | 20.434 |
| 74 | 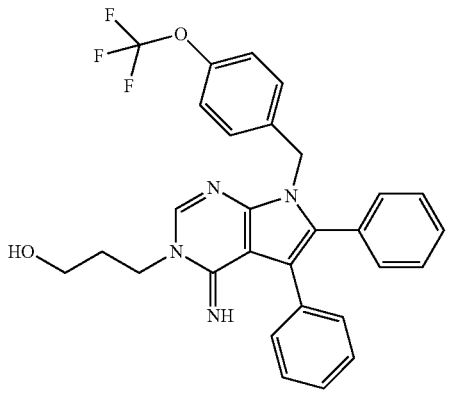 [SMILES: N=c1c2c(-c3ccccc3)c(-c3ccccc3)n(Cc3ccc(OC(F)(F)F)cc3)c2ncn1CCCO] | 0.743 | 24.149 |

TABLE 4-continued

| Compound | Structure | PNC IC$_{50}$ (μM) | ATP IC$_{50}$ (μM) |
|---|---|---|---|
| 19 | 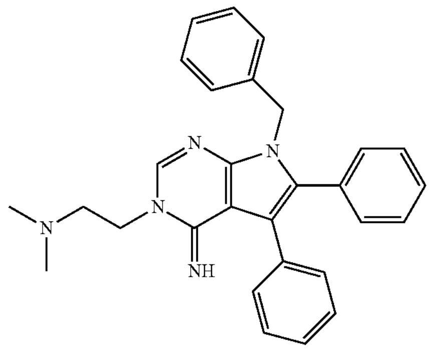 [SMILES: CN(C)CCn1cnc2c(c(-c3ccccc3)c(-c3ccccc3)n2Cc2ccccc2)c1=N] | 0.935 | 24.149 |
| 38 | 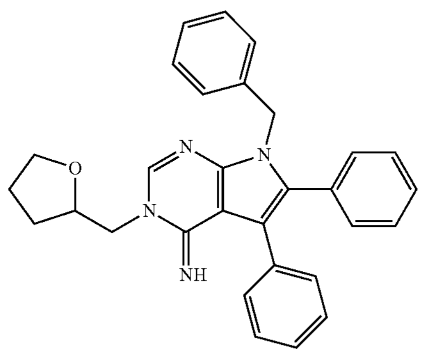 [SMILES: N=c1c2c(-c3ccccc3)c(-c3ccccc3)n(Cc3ccccc3)c2ncn1CC1CCCO1] | 0.935 | 96.138 |
| 76 | 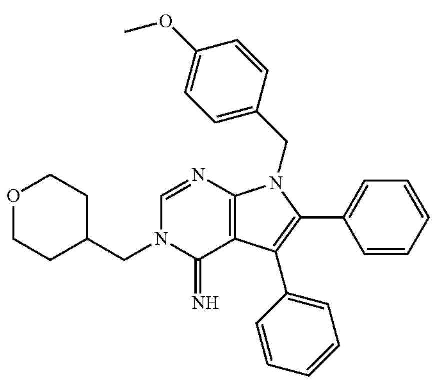 [SMILES: COc1ccc(Cn2c(-c3ccccc3)c(-c3ccccc3)c3c(=N)n(CC4CCOCC4)cnc32)cc1] | 0.935 | 48.183 |
| 75 | 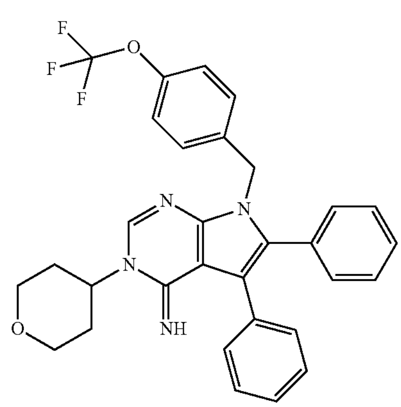 [SMILES: N=c1c2c(-c3ccccc3)c(-c3ccccc3)n(Cc3ccc(OC(F)(F)F)cc3)c2ncn1C1CCOCC1] | 0.935 | 24.149 |

TABLE 4-continued

| Compound | Structure | PNC IC$_{50}$ (μM) | ATP IC$_{50}$ (μM) |
|---|---|---|---|
| 14 | 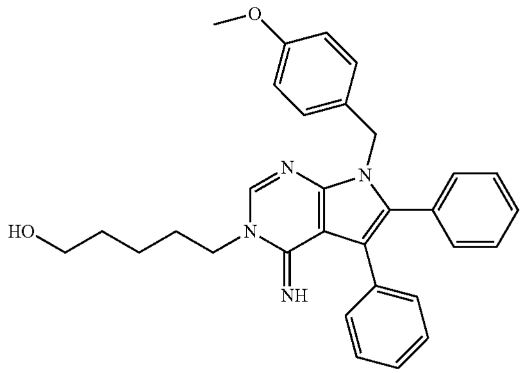 [SMILES: COc1ccc(Cn2c(-c3ccccc3)c(-c3ccccc3)c3c(=N)n(CCCCCO)cnc32)cc1] | 1.177 | 24.149 |
| 27 | 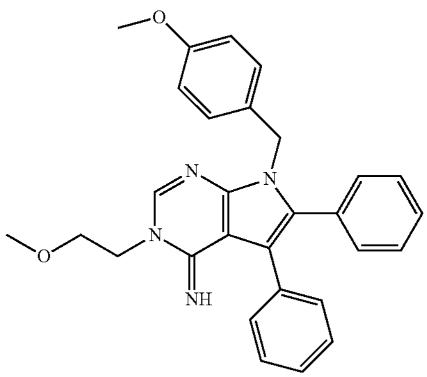 [SMILES: COCCn1cnc2c(c(-c3ccccc3)c(-c3ccccc3)n2Cc2ccc(OC)cc2)c1=N] | 1.177 | 24.149 |
| 17 | 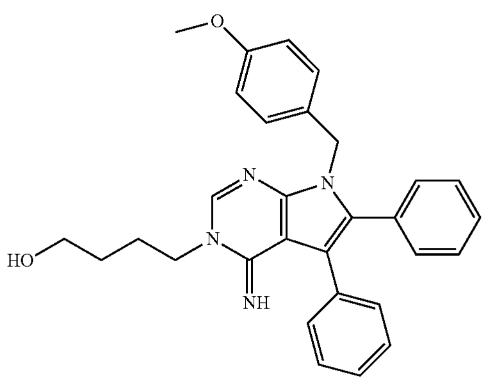 [SMILES: COc1ccc(Cn2c(-c3ccccc3)c(-c3ccccc3)c3c(=N)n(CCCCO)cnc32)cc1] | 1.177 | 30.402 |
| 77 | 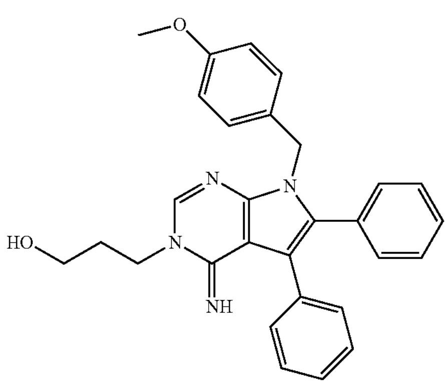 [SMILES: COc1ccc(Cn2c(-c3ccccc3)c(-c3ccccc3)c3c(=N)n(CCCO)cnc32)cc1] | 1.177 | 96.138 |

TABLE 4-continued

| Compound | Structure | PNC IC$_{50}$ (μM) | ATP IC$_{50}$ (μM) |
|---|---|---|---|
| 8 | 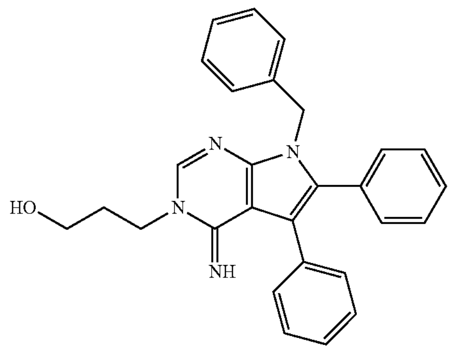 [SMILES: N=c1c2c(-c3ccccc3)c(-c3ccccc3)n(Cc3ccccc3)c2ncn1CCCO] | 1.254 | 20.434 |
| 37 | 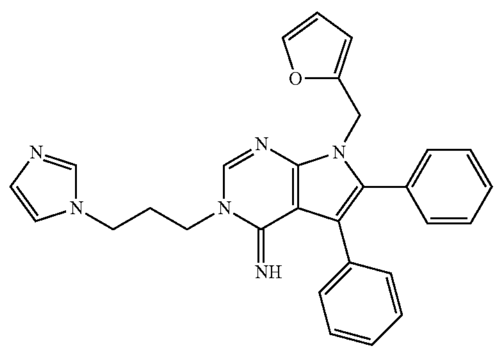 [SMILES: N=c1c2c(-c3ccccc3)c(-c3ccccc3)n(Cc3ccco3)c2ncn1CCCn1ccnc1] | 1.254 | 25.725 |
| 34 | 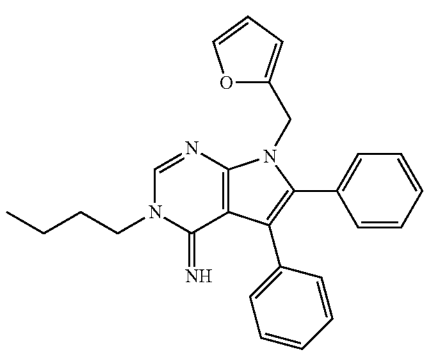 [SMILES: CCCCn1cnc2c(c(-c3ccccc3)c(-c3ccccc3)n2Cc2ccco2)c1=N] | 1.254 | 20.434 |
| 6 | 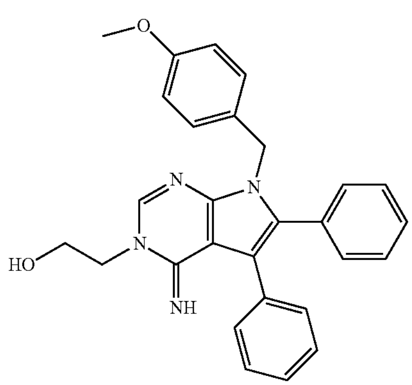 [SMILES: COc1ccc(Cn2c(-c3ccccc3)c(-c3ccccc3)c3c(=N)n(CCO)cnc32)cc1] | 1.482 | 48.183 |

TABLE 4-continued

| Compound | Structure | PNC IC$_{50}$ (μM) | ATP IC$_{50}$ (μM) |
|---|---|---|---|
| 78 | 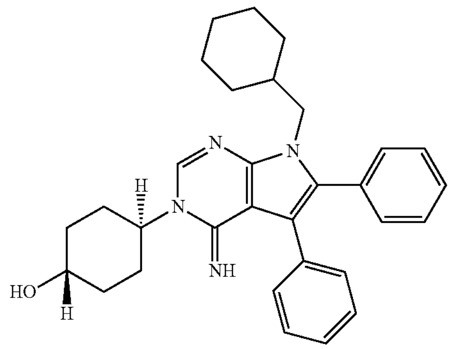 [SMILES: N=c1c2c(-c3ccccc3)c(-c3ccccc3)n(CC3CCCCC3)c2ncn1[C@H]1CC[C@H](O)CC1] | 1.482 | 30.402 |
| 25 | 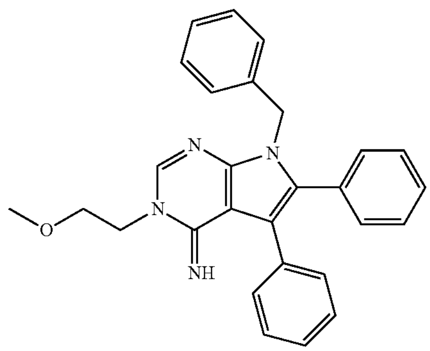 [SMILES: COCCn1cnc2c(c(-c3ccccc3)c(-c3ccccc3)n2Cc2ccccc2)c1=N] | 1.866 | 60.659 |
| 24 | 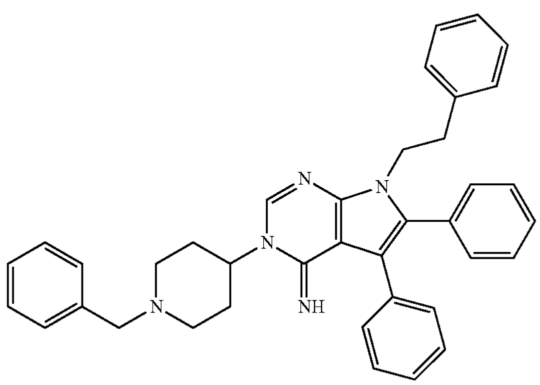 [SMILES: N=c1c2c(-c3ccccc3)c(-c3ccccc3)n(CCc3ccccc3)c2ncn1C1CCN(Cc2ccccc2)CC1] | 1.866 | 24.149 |
| 81 | 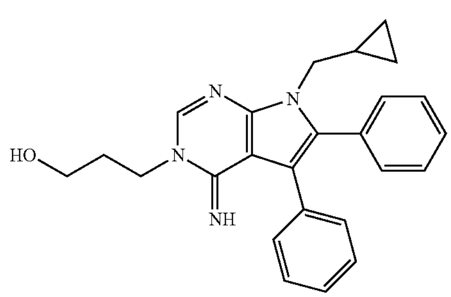 [SMILES: N=c1c2c(-c3ccccc3)c(-c3ccccc3)n(CC3CC3)c2ncn1CCCO] | 1.866 | 76.365 |

TABLE 4-continued

| Compound | Structure | PNC IC$_{50}$ (μM) | ATP IC$_{50}$ (μM) |
|---|---|---|---|
| 80 | 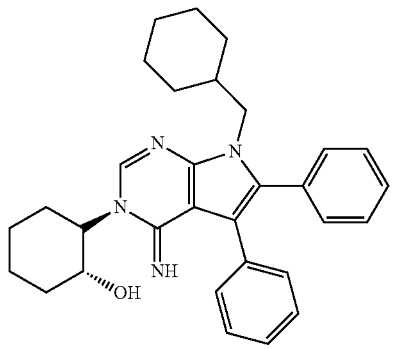 | 1.866 | 21.523 |
| 79 | 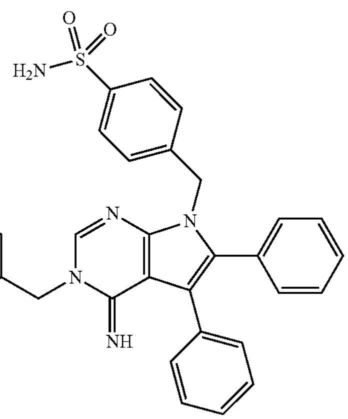 | 1.866 | 382.734 |
| 36 | 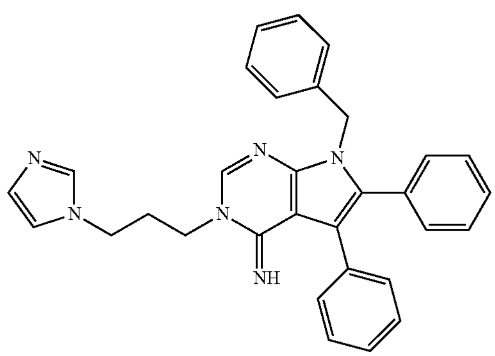 [SMILES: N=c1c2c(-c3ccccc3)c(-c3ccccc3)n(Cc3ccccc3)c2ncn1CCCn1ccnc1] | 1.987 | 25.725 |
| 82 | 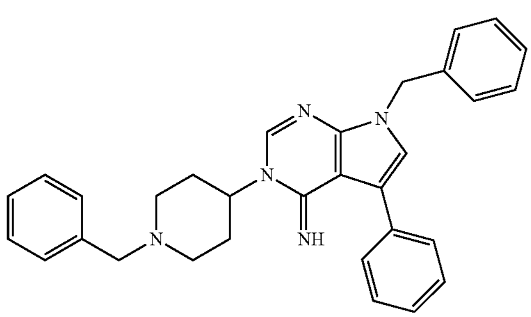 [SMILES: N=c1c2c(-c3ccccc3)cn(Cc3ccccc3)c2ncn1C1CCN(Cc2ccccc2)CC1] | 2.349 | 30.402 |

TABLE 4-continued

| Compound | Structure | PNC IC$_{50}$ (μM) | ATP IC$_{50}$ (μM) |
| --- | --- | --- | --- |
| 31 | 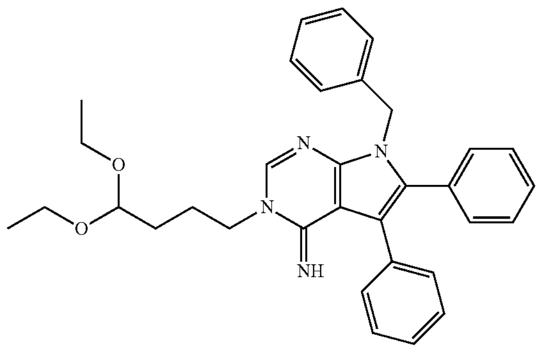 [SMILES: CCOC(CCCn1cnc2c(c(-c3ccccc3)c(-c3ccccc3)n2Cc2ccccc2)c1=N)OCC] | 2.957 | 24.149 |
| 83 | 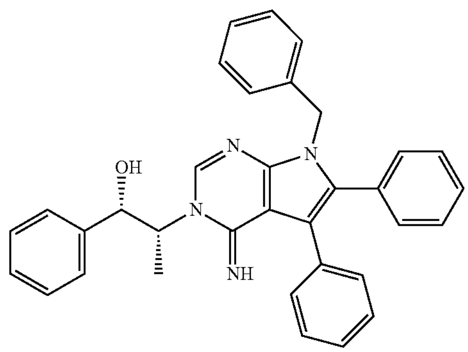 [SMILES: C[C@H]([C@@H](O)c1ccccc1)n1cnc2c(c(-c3ccccc3)c(-c3ccccc3)n2Cc2ccccc2)c1=N] | 2.957 | 24.149 |
| 33 | 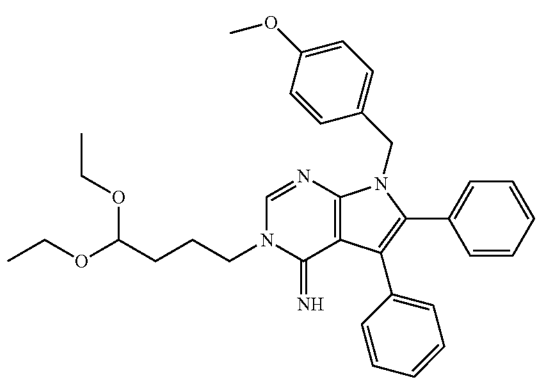 [SMILES: CCOC(CCCn1cnc2c(c(-c3ccccc3)c(-c3ccccc3)n2Cc2ccc(OC)cc2)c1=N)OCC] | 2.957 | 48.183 |
| 85 | 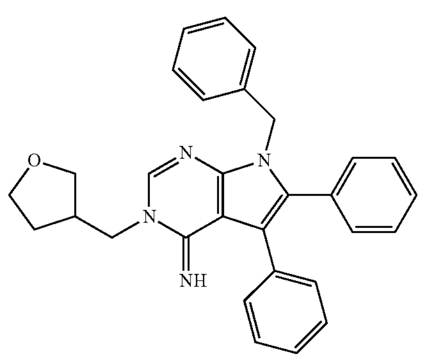 [SMILES: N=c1c2c(-c3ccccc3)c(-c3ccccc3)n(Cc3ccccc3)c2ncn1CC1CCOC1] | 2.957 | 24.149 |

TABLE 4-continued

| Compound | Structure | PNC IC$_{50}$ (μM) | ATP IC$_{50}$ (μM) |
|---|---|---|---|
| 84 | 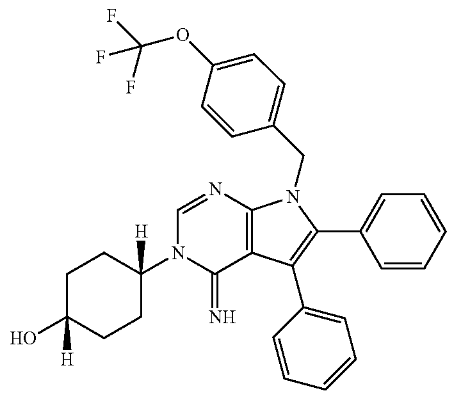 [SMILES: N=c1c2c(-c3ccccc3)c(-c3ccccc3)n(Cc3ccc(OC(F)(F)F)cc3)c2ncn1[C@H]1CC[C@@H](O)CC1] | 2.957 | 24.149 |
| 26 | 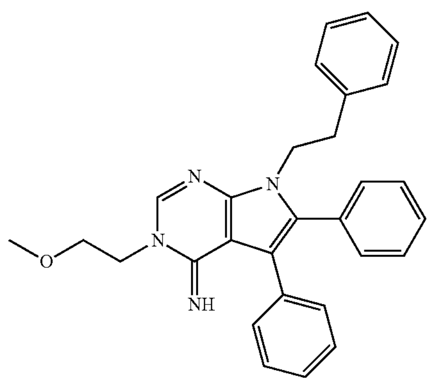 [SMILES: COCCn1cnc2c(c(-c3ccccc3)c(-c3ccccc3)n2CCc2ccccc2)c1=N] | 3.722 | 60.659 |
| 86 | 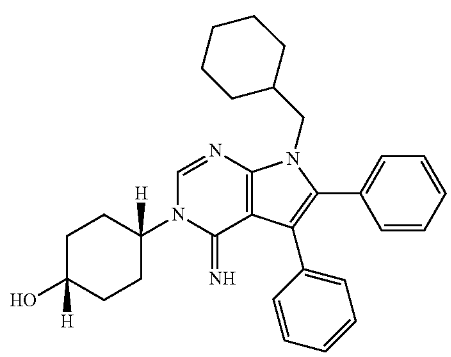 [SMILES: N=c1c2c(-c3ccccc3)c(-c3ccccc3)n(CC3CCCCC3)c2ncn1[C@H]1CC[C@@H](O)CC1] | 3.722 | 24.149 |
| 11 | 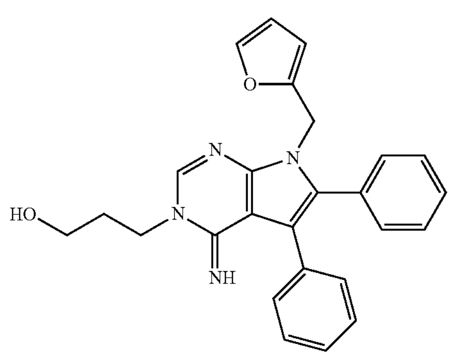 [SMILES: N=c1c2c(-c3ccccc3)c(-c3ccccc3)n(Cc3ccco3)c2ncn1CCCO] | 3.965 | 64.618 |

TABLE 4-continued

| Compound | Structure | PNC IC$_{50}$ (μM) | ATP IC$_{50}$ (μM) |
|---|---|---|---|
| 23 | 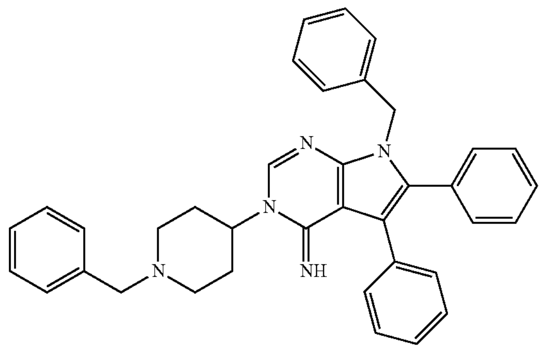 [SMILES: N=c1c2c(-c3ccccc3)c(-c3ccccc3)n(Cc3ccccc3)c2ncn1C1CCN(Cc2ccccc2)CC1] | 4.686 | 121.031 |
| 39 | 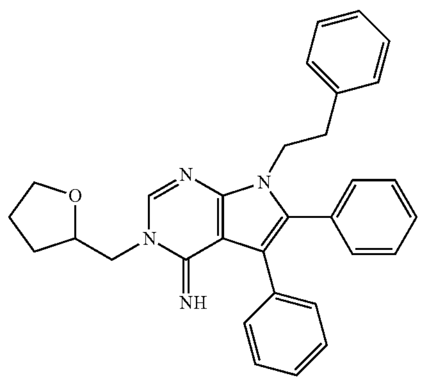 [SMILES: N=c1c2c(-c3ccccc3)c(-c3ccccc3)n(CCc3ccccc3)c2ncn1CC1CCCO1] | 4.686 | 48.183 |
| 48 | 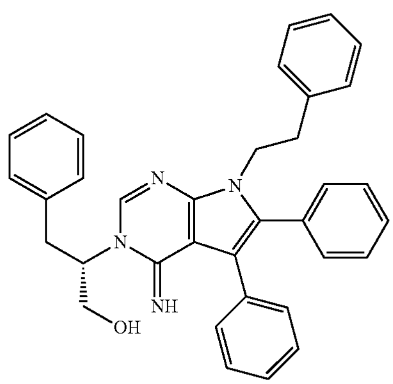 [SMILES: N=c1c2c(-c3ccccc3)c(-c3ccccc3)n(CCc3ccccc3)c2ncn1[C@H](CO)Cc1ccccc1] | 4.686 | 30.402 |
| 88 | 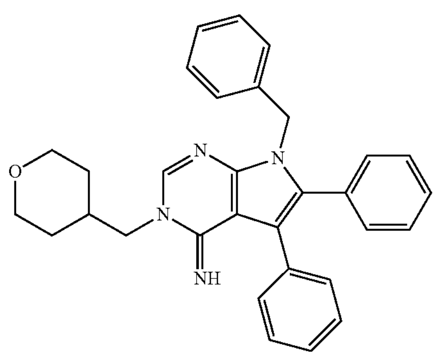 [SMILES: N=c1c2c(-c3ccccc3)c(-c3ccccc3)n(Cc3ccccc3)c2ncn1CC1CCOCC1] | 4.686 | 30.402 |

TABLE 4-continued

| Compound | Structure | PNC IC$_{50}$ (μM) | ATP IC$_{50}$ (μM) |
|---|---|---|---|
| 87 | 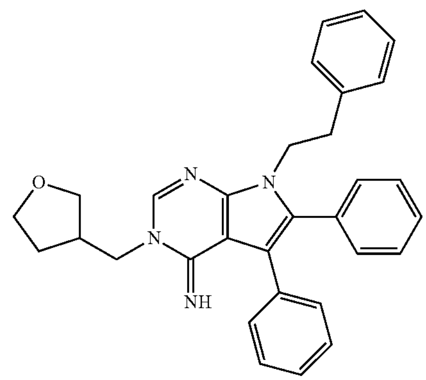 [SMILES: N=c1c2c(-c3ccccc3)c(-c3ccccc3)n(CCc3ccccc3)c2ncn1CC1CCOC1] | 4.686 | 60.659 |
| | | 5.899 | 38.273 |
| 30 | 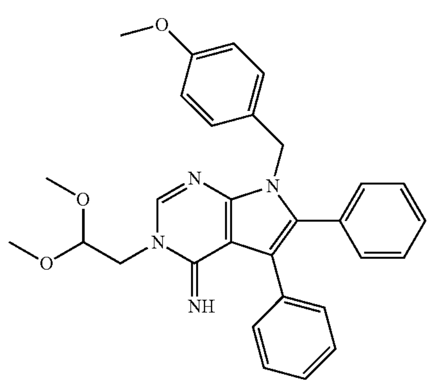 [SMILES: COc1ccc(Cn2c(-c3ccccc3)c(-c3ccccc3)c3c(=N)n(CC(OC)OC)cnc32)cc1] | 5.899 | 24.149 |
| 40 | 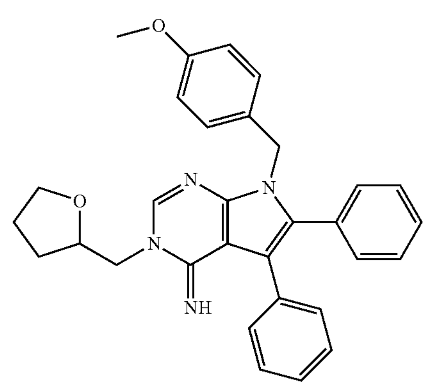 [SMILES: COc1ccc(Cn2c(-c3ccccc3)c(-c3ccccc3)c3c(=N)n(CC4CCCO4)cnc32)cc1] | 5.899 | 38.273 |

TABLE 4-continued
| Compound | Structure | PNC IC$_{50}$ (μM) | ATP IC$_{50}$ (μM) |
|---|---|---|---|
| 90 | 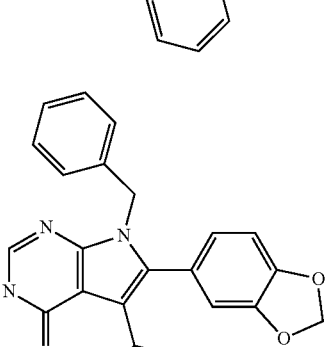 | 5.899 | 76.365 |
| 89 | 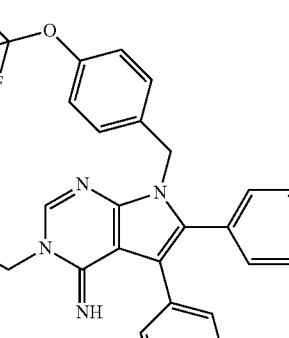 | 5.899 | 24.149 |
| 91 | 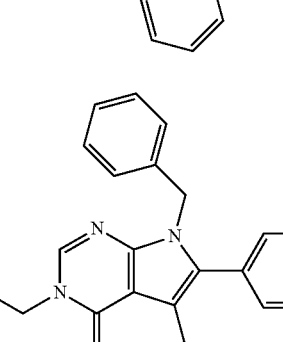 | 5.899 | 30.402 |
| 21 | 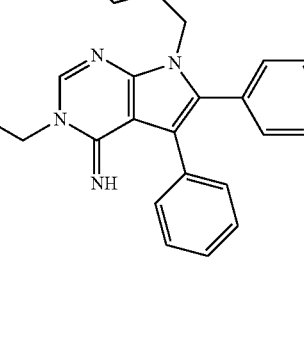 | 7.427 | 24.149 |

TABLE 4-continued
| Compound | Structure | PNC IC$_{50}$ (μM) | ATP IC$_{50}$ (μM) |
|---|---|---|---|
| 22 | 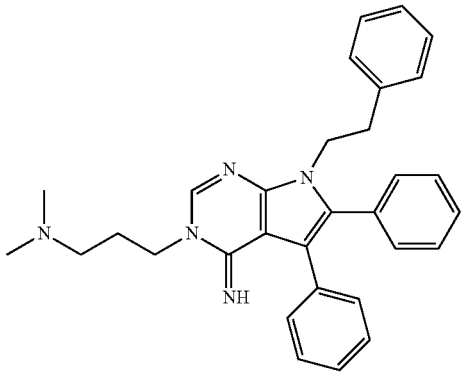 [SMILES: CN(C)CCCn1cnc2c(c(-c3ccccc3)c(-c3ccccc3)n2CCc2ccccc2)c1=N] | 7.427 | 24.149 |
| 97 | 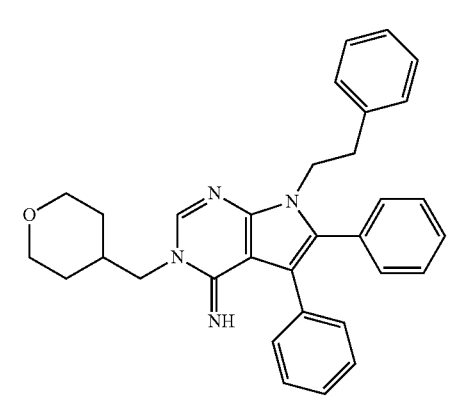 [SMILES: N=c1c2c(-c3ccccc3)c(-c3ccccc3)n(CCc3ccccc3)c2ncn1CC1CCOCC1] | 7.427 | 96.138 |
| 93 | 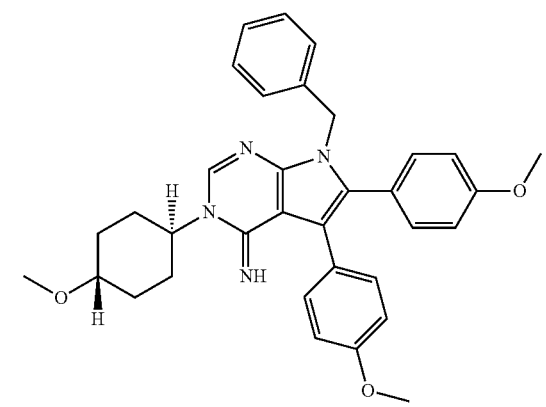 | 7.427 | 60.659 |
| 45 | 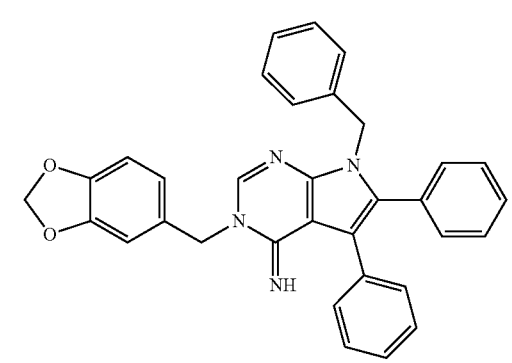 [SMILES: N=c1c2c(-c3ccccc3)c(-c3ccccc3)n(Cc3ccccc3)c2ncn1Cc1ccc2c(c1)OCO2] | 9.350 | 24.149 |

TABLE 4-continued

| Compound | Structure | PNC IC$_{50}$ (μM) | ATP IC$_{50}$ (μM) |
|---|---|---|---|
| 94 | 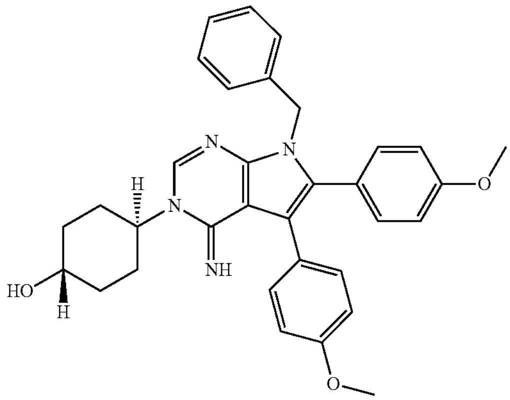 [SMILES: COc1ccc(-c2c(-c3ccc(OC)cc3)n(Cc3ccccc3)c3ncn([C@H]4CC[C@H](O)CC4)c(=N)c23)cc1] | 9.350 | 24.149 |
| 43 | 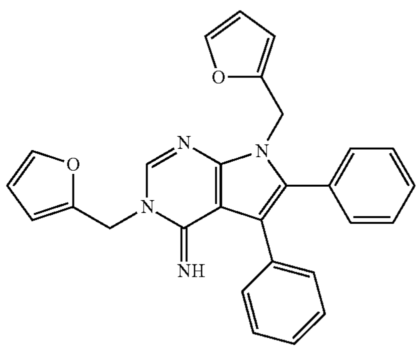 [SMILES: N=c1c2c(-c3ccccc3)c(-c3ccccc3)n(Cc3ccco3)c2ncn1Cc1ccco1] | 9.960 | 20.434 |
| 96 | 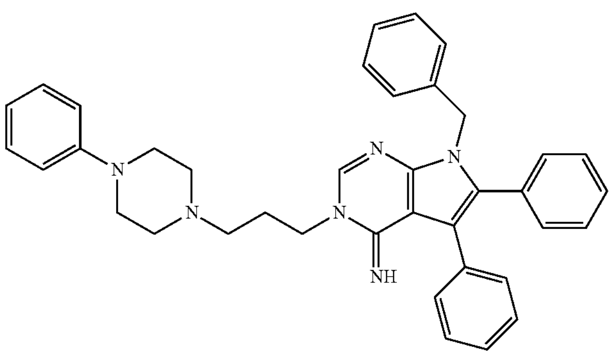 [SMILES: N=c1c2c(-c3ccccc3)c(-c3ccccc3)n(Cc3ccccc3)c2ncn1CCCN1CCN(c2ccccc2)CC1] | 11.770 | 30.402 |
| 95 | 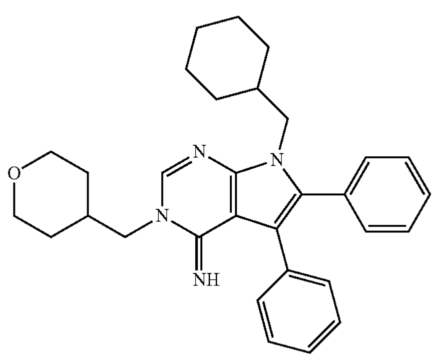 [SMILES: N=c1c2c(-c3ccccc3)c(-c3ccccc3)n(CC3CCCCC3)c2ncn1CC1CCOCC1] | 11.770 | 24.149 |

TABLE 4-continued
| Compound | Structure | PNC IC$_{50}$ (μM) | ATP IC$_{50}$ (μM) |
|---|---|---|---|
| 99 | 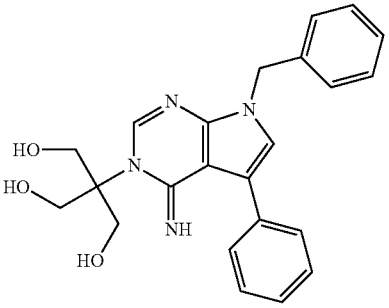 [SMILES: N=c1c2c(-c3ccccc3)cn(Cc3ccccc3)c2ncn1C(CO)(CO)CO] | 14.818 | inactive |
| 46 | 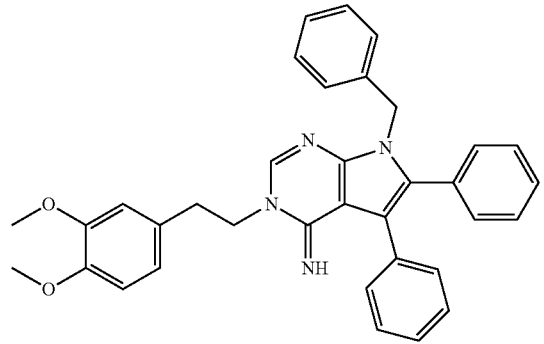 [SMILES: COc1ccc(CCn2cnc3c(c(-c4ccccc4)c(-c4ccccc4)n3Cc3ccccc3)c2=N)cc1OC] | 14.818 | 24.149 |
| 98 | 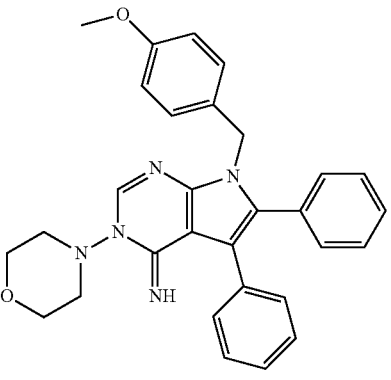 [SMILES: COc1ccc(Cn2c(-c3ccccc3)c(-c3ccccc3)c3c(=N)n(N4CCOCC4)cnc32)cc1] | 14.818 | 121.031 |
| 101 | 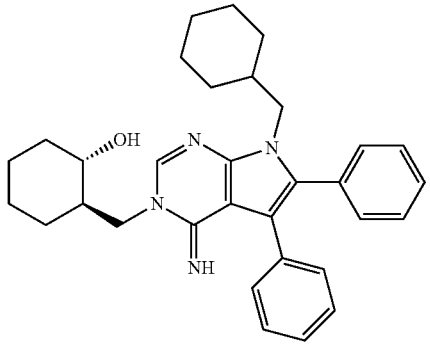 [SMILES: N=c1c2c(-c3ccccc3)c(-c3ccccc3)n(CC3CCCCC3)c2ncn1C[C@H]1CCCC[C@@H]1O] | 14.818 | 24.149 |

TABLE 4-continued

| Compound | Structure | PNC IC$_{50}$ (μM) | ATP IC$_{50}$ (μM) |
|---|---|---|---|
| 97 | 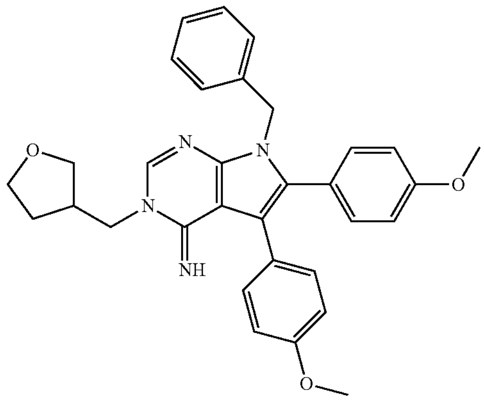 [SMILES: COc1ccc(-c2c(-c3ccc(OC)cc3)n(Cc3ccccc3)c3ncn(CC4CCOC4)c(=N)c23)cc1] | 14.818 | 48.183 |
| 100 | 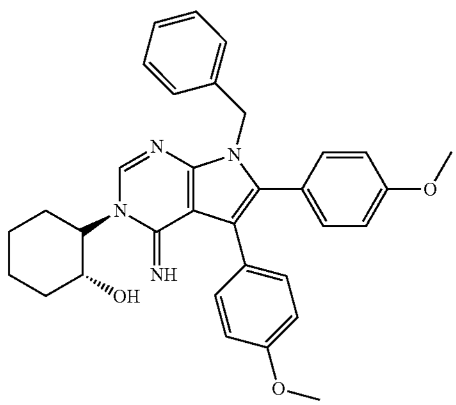 | 14.818 | 48.183 |
| 102 | 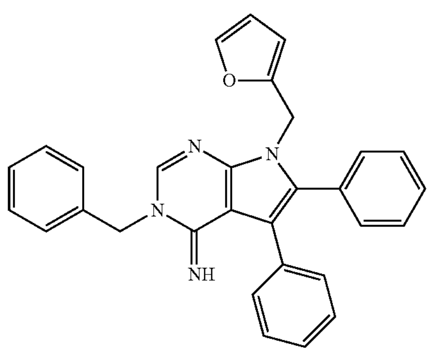 [SMILES: N=c1c2c(-c3ccccc3)c(-c3ccccc3)n(Cc3ccco3)c2ncn1Cc1ccccc1] | 15.785 | 25.725 |
| 141 | 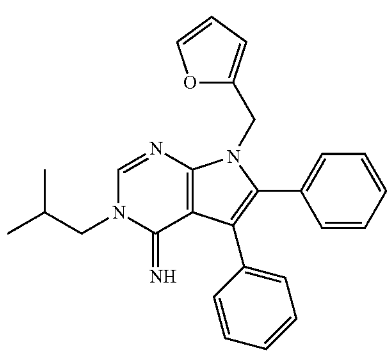 [SMILES: CC(C)Cn1cnc2c(c(-c3ccccc3)c(-c3ccccc3)n2Cc2ccco2)c1=N] | 15.785 | 20.434 |

TABLE 4-continued

| Compound | Structure | PNC IC$_{50}$ (µM) | ATP IC$_{50}$ (µM) |
|---|---|---|---|
| 32 | 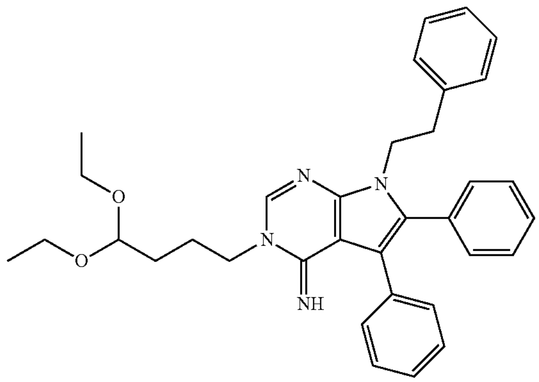 [SMILES: CCOC(CCCn1cnc2c(c(-c3ccccc3)c(-c3ccccc3)n2CCc2ccccc2)c1=N)OCC] | 18.655 | 24.149 |
| 103 | 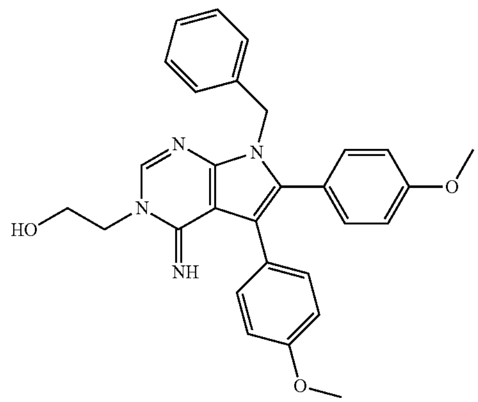 [SMILES: COc1ccc(-c2c(-c3ccc(OC)cc3)n(Cc3ccccc3)c3ncn(CCO)c(=N)c23)cc1] | 18.655 | 24.149 |
| 29 | 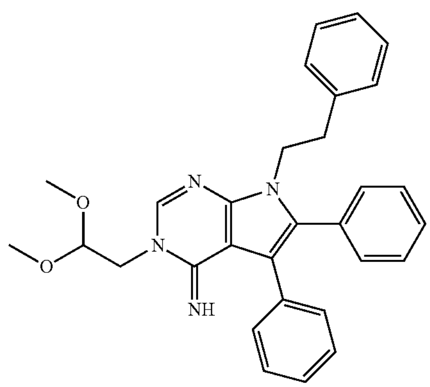 [SMILES: COC(Cn1cnc2c(c(-c3ccccc3)c(-c3ccccc3)n2CCc2ccccc2)c1=N)OC] | 23.485 | 27.096 |
| 104 | 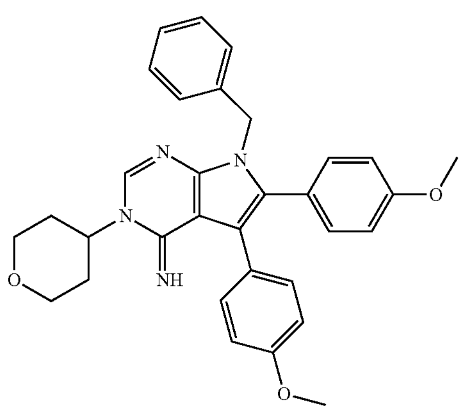 [SMILES: COc1ccc(-c2c(-c3ccc(OC)cc3)n(Cc3ccccc3)c3ncn(C4CCOCC4)c(=N)c23)cc1] | 23.485 | 30.402 |

TABLE 4-continued
| Compound | Structure | PNC IC$_{50}$ (μM) | ATP IC$_{50}$ (μM) |
|---|---|---|---|
| 106 | 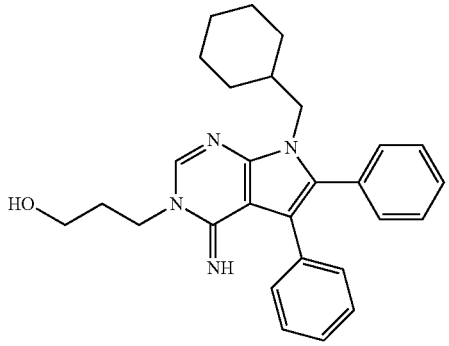 [SMILES: N=c1c2c(-c3ccccc3)c(-c3ccccc3)n(CC3CCCCC3)c2ncn1CCCO] | 23.485 | 30.402 |
| 105 | 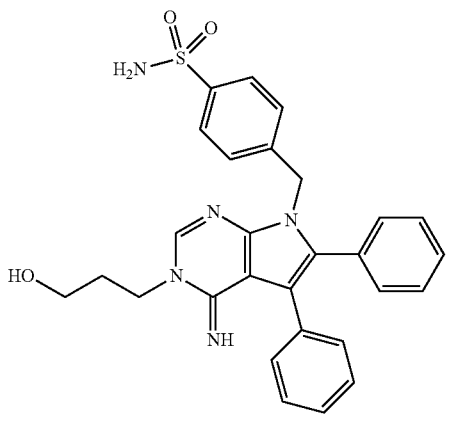 [SMILES: N=c1c2c(-c3ccccc3)c(-c3ccccc3)n(Cc3ccc(S(N)(=O)=O)cc3)c2ncn1CCCO] | 23.485 | 304.016 |
| 107 | 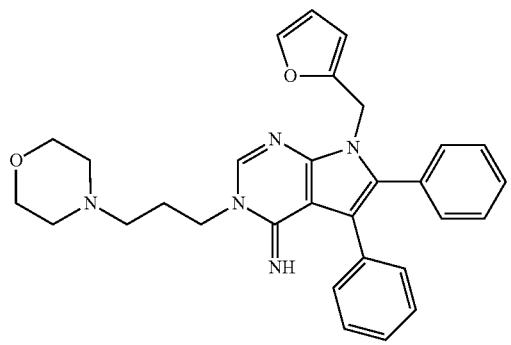 [SMILES: N=c1c2c(-c3ccccc3)c(-c3ccccc3)n(Cc3ccco3)c2ncn1CCCN1CCOCC1] | 25.018 | 32.386 |
| 108 | 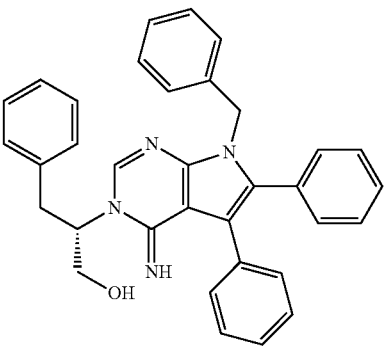 [SMILES: N=c1c2c(-c3ccccc3)c(-c3ccccc3)n(Cc3ccccc3)c2ncn1[C@H](CO)Cc1ccccc1] | 29.566 | 38.273 |

TABLE 4-continued

| Compound | Structure | PNC IC$_{50}$ (μM) | ATP IC$_{50}$ (μM) |
|---|---|---|---|
| 53 | 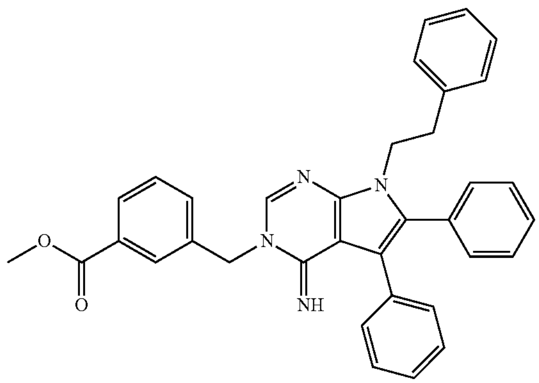 [SMILES: COC(=O)c1cccc(Cn2cnc3c(c(-c4ccccc4)c(-c4ccccc4)n3CCc3ccccc3)c2=N)c1] | 29.566 | 24.149 |
| 37 | 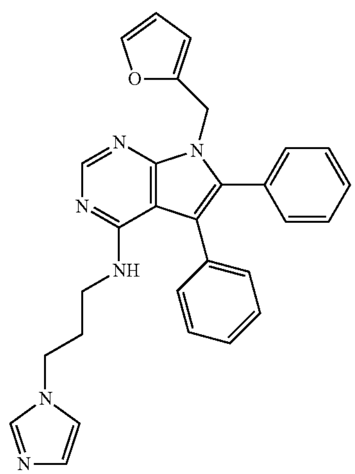 [SMILES: c1ccc(-c2c(-c3ccccc3)n(Cc3ccco3)c3ncnc(NCCCn4ccnc4)c23)cc1] | 39.650 | 81.349 |
| 110 | 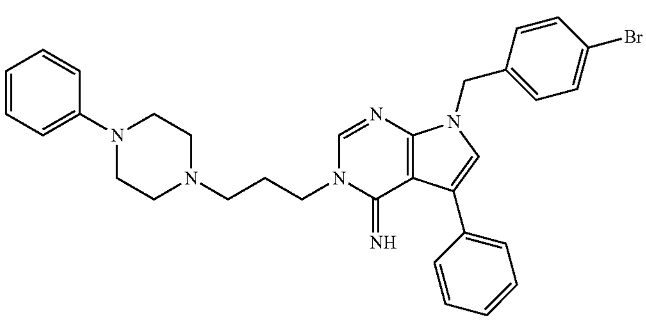 [SMILES: N=c1c2c(-c3ccccc3)cn(Cc3ccc(Br)cc3)c2ncn1CCCN1CCN(c2ccccc2)CC1] | 46.859 | 30.402 |
| 109 | 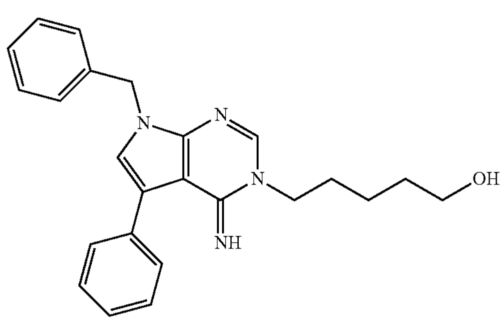 [SMILES: N=c1c2c(-c3ccccc3)cn(Cc3ccccc3)c2ncn1CCCCCO] | 46.859 | 96.138 |

TABLE 4-continued
| Compound | Structure | PNC IC$_{50}$ (μM) | ATP IC$_{50}$ (μM) |
|---|---|---|---|
| 111 | 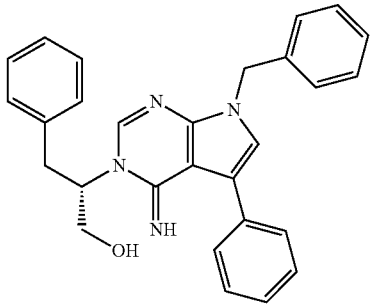 [SMILES: N=c1c2c(-c3ccccc3)cn(Cc3ccccc3)c2ncn1[C@H](CO)Cc1ccccc1] | 93.496 | 121.031 |
| 137 | 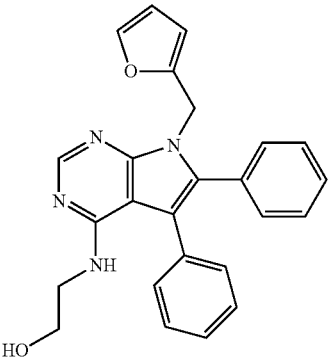 [SMILES: OCCNc1ncnc2c1c(-c1ccccc1)c(-c1ccccc1)n2Cc1ccco1] | inactive | inactive |
| 50 | 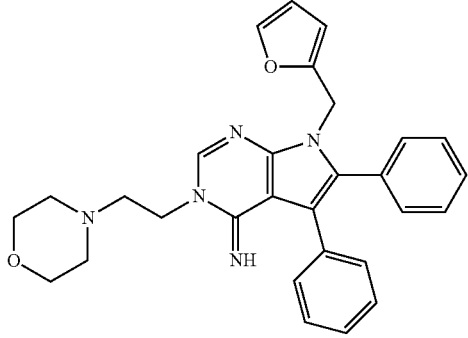 [SMILES: N=c1c2c(-c3ccccc3)c(-c3ccccc3)n(Cc3ccco3)c2ncn1CCN1CCOCC1] | inactive | 32.386 |
| 116 | 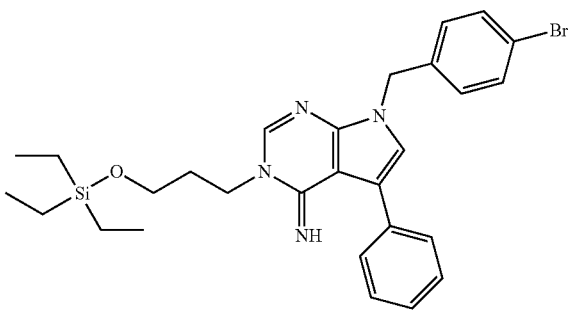 [SMILES: CC[Si](CC)(CC)OCCCn1cnc2c(c(-c3ccccc3)cn2Cc2ccc(Br)cc2)c1=N] | inactive | inactive |

TABLE 4-continued

| Compound | Structure | PNC IC$_{50}$ (μM) | ATP IC$_{50}$ (μM) |
|---|---|---|---|
| 10 | 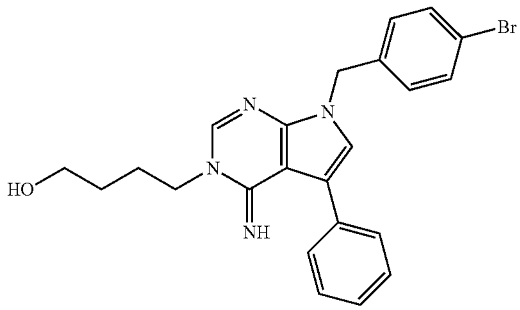 [SMILES: N=c1c2c(-c3ccccc3)cn(Cc3ccc(Br)cc3)c2ncn1CCCCO] | inactive | 96.138 |
| 114 | 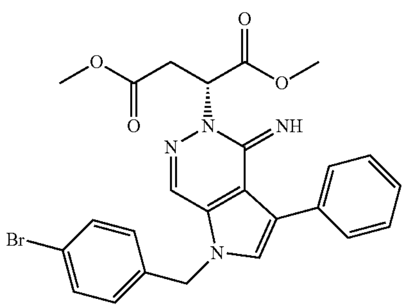 [SMILES: COC(=O)C[C@H](C(=O)OC)n1ncc2c(c(-c3ccccc3)cn2Cc2ccc(Br)cc2)c1=N] | inactive | inactive |
| 140 | 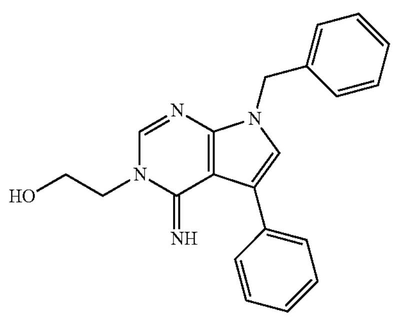 [SMILES: N=c1c2c(-c3ccccc3)cn(Cc3ccccc3)c2ncn1CCO] | inactive | inactive |
| 118 | 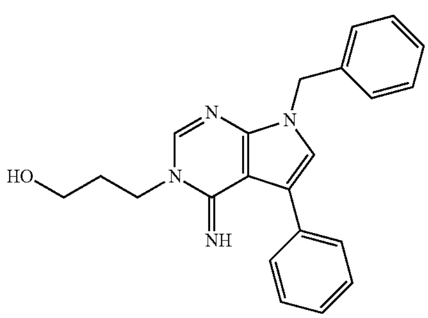 [SMILES: N=c1c2c(-c3ccccc3)cn(Cc3ccccc3)c2ncn1CCCO] | inactive | 121.031 |
| 125 | 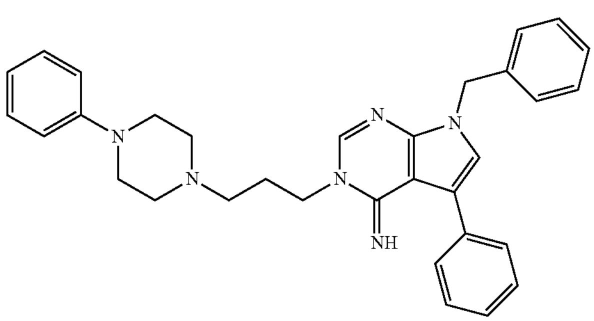 [SMILES: N=c1c2c(-c3ccccc3)cn(Cc3ccccc3)c2ncn1CCCN1CCN(c2ccccc2)CC1] | inactive | 30.402 |

TABLE 4-continued
| Compound | Structure | PNC IC$_{50}$ (μM) | ATP IC$_{50}$ (μM) |
|---|---|---|---|
| 10 | 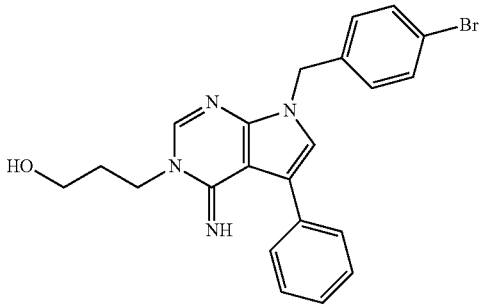 [SMILES: N=c1c2c(-c3ccccc3)cn(Cc3ccc(Br)cc3)c2ncn1CCCO] | inactive | 48.183 |
| 120 | 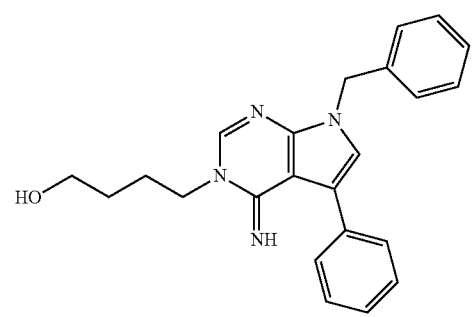 [SMILES: N=c1c2c(-c3ccccc3)cn(Cc3ccccc3)c2ncn1CCCCO] | inactive | 241.489 |
| 139 | 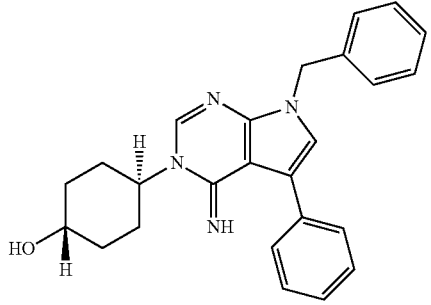 [SMILES: N=c1c2c(-c3ccccc3)cn(Cc3ccccc3)c2ncn1[C@H]1CC[C@H](O)CC1] | inactive | inactive |
| 128 | 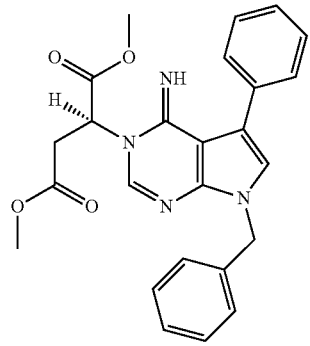 [SMILES: COC(=O)C[C@@H](C(=O)OC)n1cnc2c(c(-c3ccccc3)cn2Cc2ccccc2)c1=N] | inactive | inactive |

TABLE 4-continued

| Compound | Structure | PNC IC$_{50}$ (μM) | ATP IC$_{50}$ (μM) |
| --- | --- | --- | --- |
| 130 | 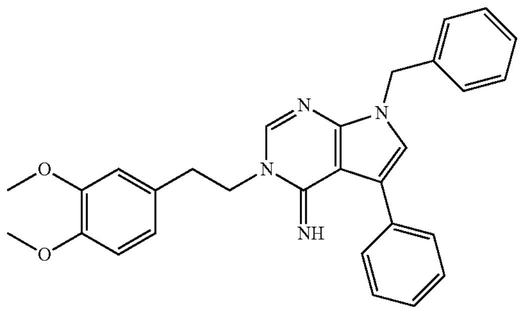 [SMILES: COc1ccc(CCn2cnc3c(c(-c4ccccc4)cn3Cc3ccccc3)c2=N)cc1OC] | inactive | 24.149 |
| 136 | 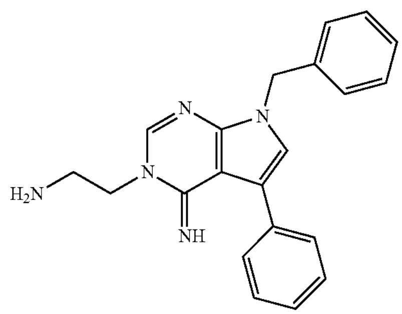 [SMILES: N=c1c2c(-c3ccccc3)cn(Cc3ccccc3)c2ncn1CCN] | inactive | inactive |
| 131 | 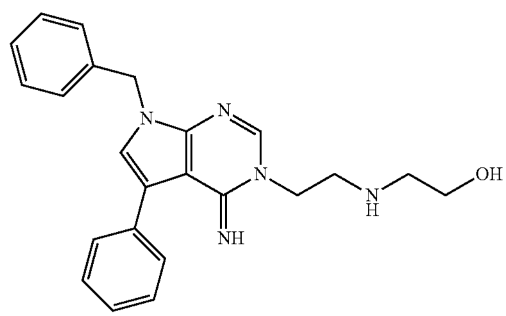 [SMILES: N=c1c2c(-c3ccccc3)cn(Cc3ccccc3)c2ncn1CCNCCO] | inactive | 121.031 |
| 119 | 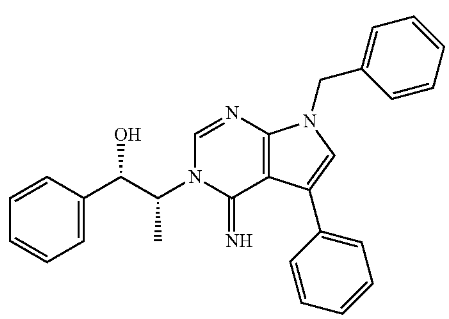 [SMILES: C[C@H]([C@@H](O)c1ccccc1)n1cnc2c(c(-c3ccccc3)cn2Cc2ccccc2)c1=N] | inactive | 121.031 |
| 117 | 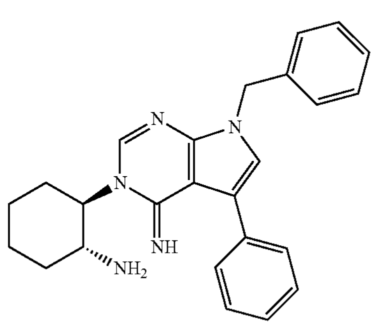 [SMILES: N=c1c2c(-c3ccccc3)cn(Cc3ccccc3)c2ncn1[C@@H]1CCCC[C@H]1N] | inactive | 96.138 |

TABLE 4-continued

| Compound | Structure | PNC IC$_{50}$ (μM) | ATP IC$_{50}$ (μM) |
|---|---|---|---|
| 122 | 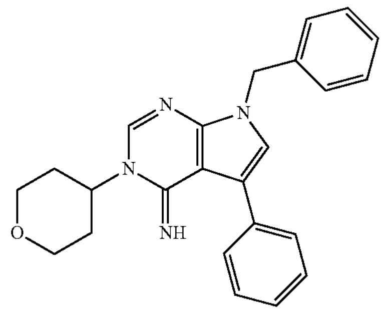 [SMILES: N=c1c2c(-c3ccccc3)cn(Cc3ccccc3)c2ncn1C1CCOCC1] | inactive | inactive |
| 115 | 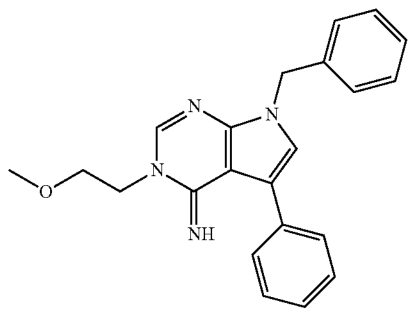 [SMILES: COCCn1cnc2c(c(-c3ccccc3)cn2Cc2ccccc2)c1=N] | inactive | 121.031 |
| 127 | 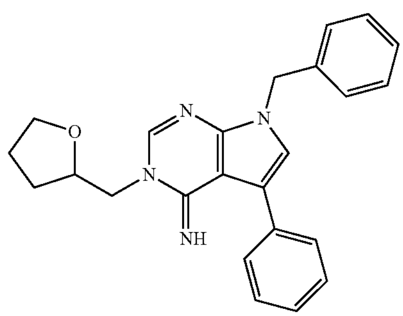 [SMILES: N=c1c2c(-c3ccccc3)cn(Cc3ccccc3)c2ncn1CC1CCCO1] | inactive | 96.138 |
| 124 | 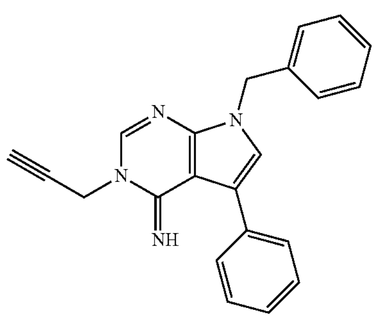 [SMILES: C#CCn1cnc2c(c(-c3ccccc3)cn2Cc2ccccc2)c1=N] | inactive | inactive |
| 138 | 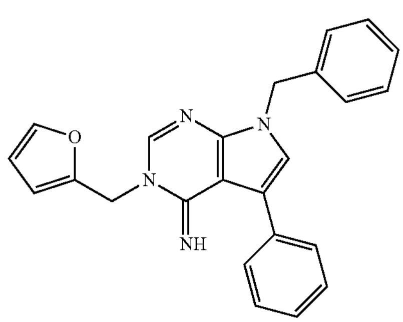 [SMILES: N=c1c2c(-c3ccccc3)cn(Cc3ccccc3)c2ncn1Cc1ccco1] | inactive | 60.659 |

TABLE 4-continued

| Compound | Structure | PNC IC$_{50}$ (µM) | ATP IC$_{50}$ (µM) |
|---|---|---|---|
| 121 | 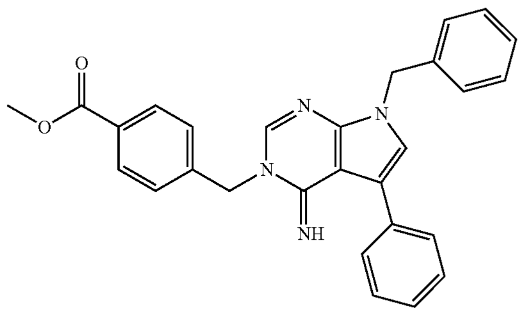 [SMILES: COC(=O)c1ccc(Cn2cnc3c(c(-c4ccccc4)cn3Cc3ccccc3)c2=N)cc1] | inactive | 121.031 |
| 12 | 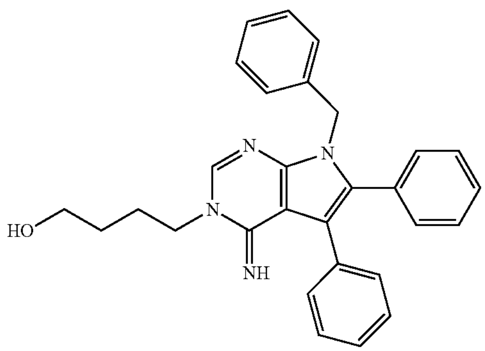 [SMILES: N=c1c2c(-c3ccccc3)c(-c3ccccc3)n(Cc3ccccc3)c2ncn1CCCCO] | inactive | 24.149 |
| 18 | 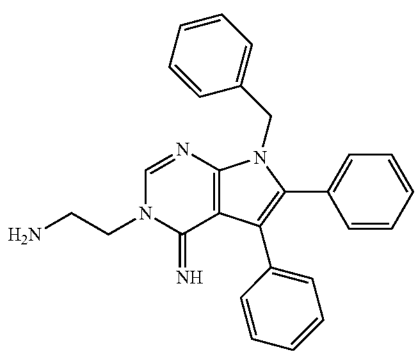 [SMILES: N=c1c2c(-c3ccccc3)c(-c3ccccc3)n(Cc3ccccc3)c2ncn1CCN] | inactive | 76.365 |
| 112 | 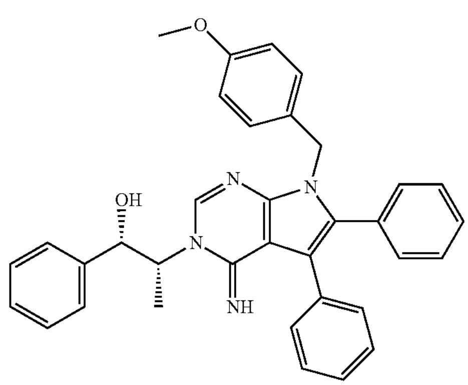 [SMILES: COc1ccc(Cn2c(-c3ccccc3)c(-c3ccccc3)c3c(=N)n([C@H](C)[C@@H](O)c4ccccc4)cnc32)cc1] | inactive | 60.659 |

TABLE 4-continued

| Compound | Structure | PNC IC$_{50}$ (μM) | ATP IC$_{50}$ (μM) |
|---|---|---|---|
| 132 | 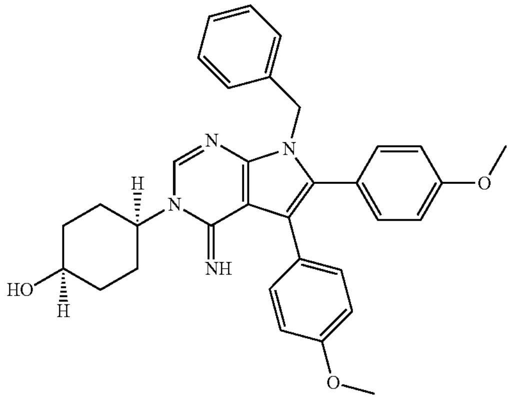 [SMILES: COc1ccc(-c2c(-c3ccc(OC)cc3)n(Cc3ccccc3)c3ncn([C@H]4CC[C@@H](O)CC4)c(=N)c23)cc1] | inactive | inactive |
| 126 | 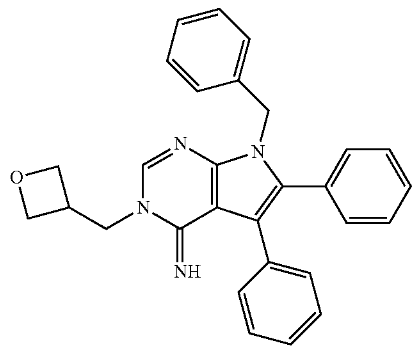 [SMILES: N=c1c2c(-c3ccccc3)c(-c3ccccc3)n(Cc3ccccc3)c2ncn1CC1COC1] | inactive | 96.138 |
| 129 | 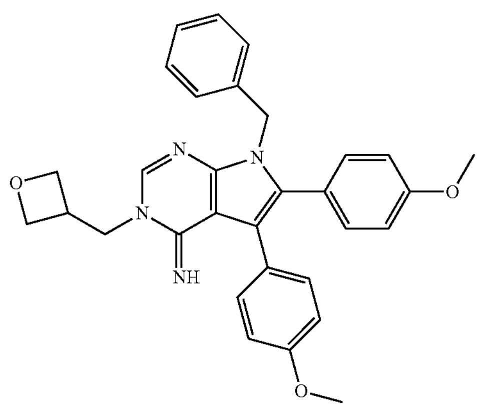 [SMILES: COc1ccc(-c2c(-c3ccc(OC)cc3)n(Cc3ccccc3)c3ncn(CC4COC4)c(=N)c23)cc1] | inactive | inactive |
| 135 | 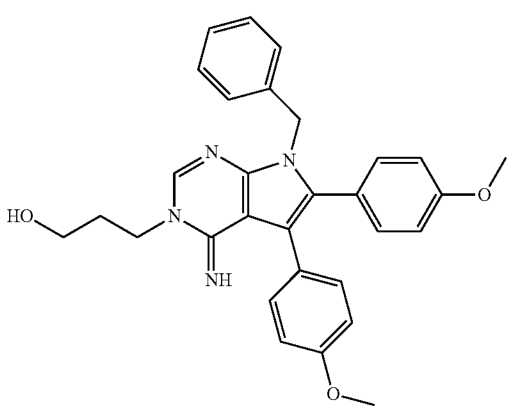 [SMILES: COc1ccc(-c2c(-c3ccc(OC)cc3)n(Cc3ccccc3)c3ncn(CCCO)c(=N)c23)cc1] | inactive | 30.402 |

TABLE 4-continued

| Compound | Structure | PNC IC$_{50}$ (μM) | ATP IC$_{50}$ (μM) |
|---|---|---|---|
| 134 | 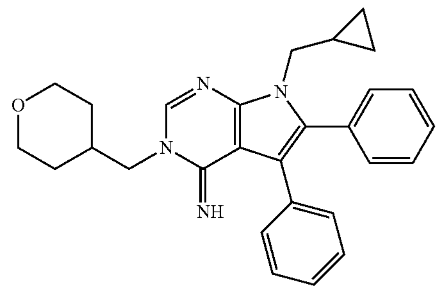 [SMILES: N=c1c2c(-c3ccccc3)c(-c3ccccc3)n(CC3CC3)c2ncn1CC1CCOCC1] | inactive | 60.659 |
| 123 | 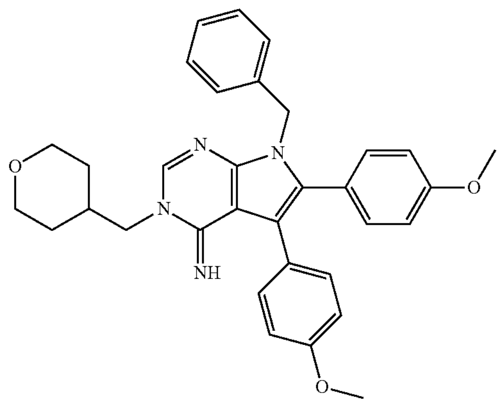 [SMILES: COc1ccc(-c2c(-c3ccc(OC)cc3)n(Cc3ccccc3)c3ncn(CC4CCOCC4)c(=N)c23)cc1] | inactive | 24.149 |
| 113 | 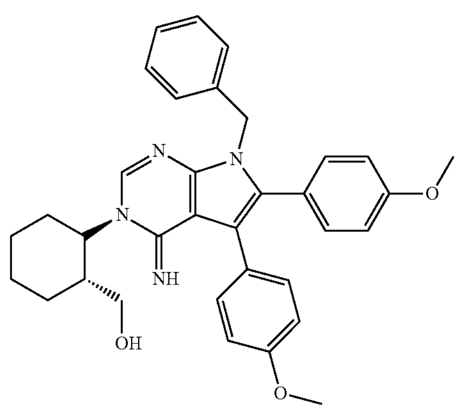 | inactive | 30.402 |
| 35 | 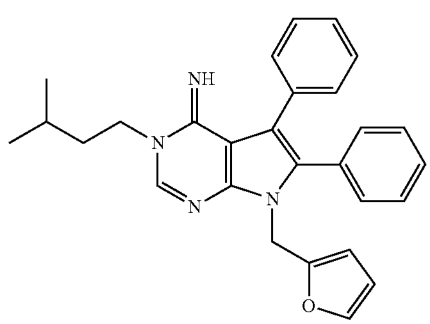 [SMILES: CC(C)CCn1cnc2c(c(-c3ccccc3)c(-c3ccccc3)n2Cc2ccco2)c1=N] | Inactive | 19.87 |

TABLE 4-continued

| Compound | Structure | PNC IC$_{50}$ (µM) | ATP IC$_{50}$ (µM) |
|---|---|---|---|
| 44 | 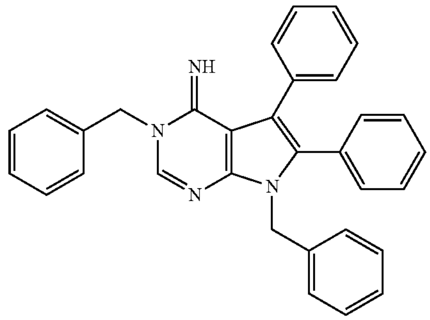 [SMILES: N=c1c2c(-c3ccccc3)c(-c3ccccc3)n(Cc3ccccc3)c2ncn1Cc1ccccc1] | 15.79 | 19.87 |

Thus provided are compounds of formula I, which compounds or pharmaceutically acceptable salts thereof for example, as known in the art, may be used in the various combination and coadministration embodiments of the invention. Suitable pharmaceutically acceptable salts include but are not limited to acid addition salts of: glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), undecylenic acid, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, and glycerophosphoric acid.

In view of the preceding and without limitation, the invention provides the following embodiments.

Embodiment 1

A pharmaceutical composition, including:
(i.) a therapeutically effective amount of a dihydropyrimidine dehydrogenase (DPYD) inhibitor, such as 5-chloro-2,4-dihydroxypyridine (gimeracil), or a pharmaceutically acceptable salt thereof; and
(ii.) a therapeutically effective amount of a compound of formula (I):

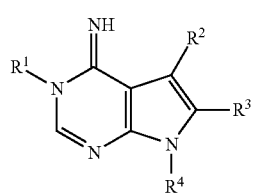

(I)

or a pharmaceutically acceptable salt thereof;

wherein $R^1$ is selected from the group consisting of alkyl, hydroxyalkyl, thioalkyl, alkoxyalkyl, alkylthioalkyl, cycloalkyl, hydroxycycloalkyl, hydroxycycloalkylalkyl, thiocycloalkyl, alkoxycycloalkyl, alkylthiocycloalkyl, dialkylaminoalkyl, heterocyclyl, heterocyclylalkyl, heteroaryl, arylalkyl, arylalkylpiperidin-4-yl, arylpiperazinylalkyl, and heteroarylalkyl, $R^2$ is aryl or heteroaryl, $R^3$ is selected from the group consisting of H, alkyl, cycloalkyl, aryl, heteroaryl, arylalkyl, and heteroarylalkyl, $R^4$ is selected from the group consisting of alkyl, cycloalkyl, cycloalkylalkyl, aryl, heteroaryl, arylalkyl, and heteroarylalkyl, wherein $R^1$, $R^2$, $R^3$, and $R^4$, other than H, are optionally substituted on the aryl and/or alkyl portion with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, alkylenedioxy, and alkylcarbonyl, with the proviso that when $R^2$ and $R^3$ are both unsubstituted phenyl and $R^4$ is unsubstituted benzyl, $R^1$ is not 3-hydroxypropyl.

Embodiment 2

The composition, wherein $R^2$ is phenyl, optionally substituted with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl.

Embodiment 3

The composition of embodiment 2, wherein $R^2$ is phenyl.

Embodiment 4

The composition of any one of embodiments 1-3, wherein $R^3$ is phenyl, optionally substituted with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl.

Embodiment 5

The composition of embodiment 4, wherein $R^3$ is phenyl.

Embodiment 6

The composition of any one of embodiments 1-5, wherein $R^4$ is benzyl, wherein the phenyl ring is optionally substituted with one or more substituents selected from the group consisting of alkyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, and alkylcarbonyl.

Embodiment 7

The composition of embodiment 6, wherein $R^4$ is benzyl.

Embodiment 8

The composition of any one of embodiments 1-7, wherein $R^1$ is a 5 or 6-membered heterocyclyl group having at least one hetero atom selected from the group consisting of O, N, and S; a hydroxy $C_1$-$C_7$ cycloalkyl group; a hydroxy Q-C6 alkyl group; a N,N-di(C]-$C_6$ alkyl)amino $C_1$-$C_6$ alkyl group; a $C_1$-$C_6$ alkoxy $C_1$-$C_6$ alkyl group; a heteroaryl $C_1$-$C_6$ alkyl group; a heterocyclyl $C_1$-$C_6$ alkyl group; phenyl $C_1$-$C_6$ alkyl group where the phenyl ring is substituted with one or more $C_1$-$C_6$ alkoxy groups; N-benzyl piperazinyl; N-phenyl piperazinylalkyl; a phenyl $C_1$-$C_6$ alkyl group where the alkyl is substituted with a hydroxy group; or a 5 or 6 membered heteroaryl amino $C_1$-$C_6$ alkyl group wherein the heteroaryl group has at least one hetero atom selected from the group consisting of O, N, and S.

Embodiment 9

The composition of any one of embodiments 1-8, wherein $R^1$ is selected from the group consisting of:

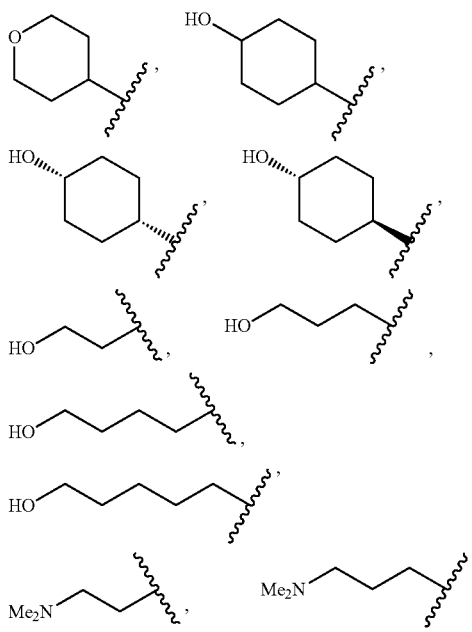

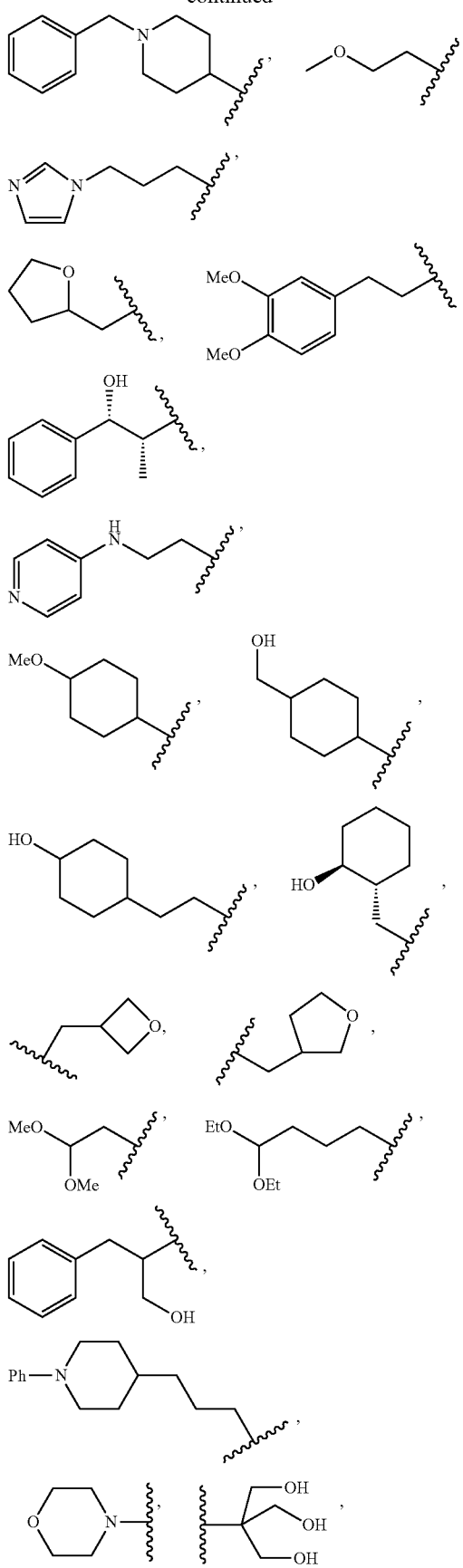

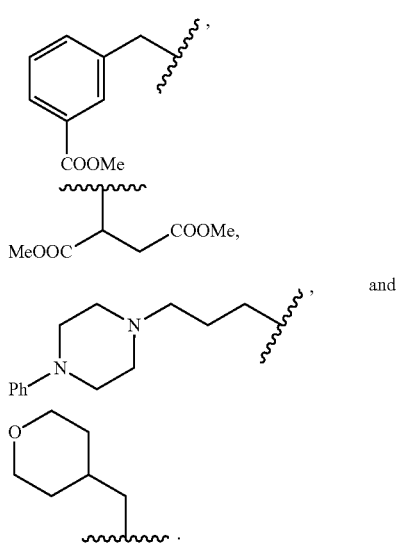
10. The composition of any one of embodiments 1-9, wherein $R^2$ is phenyl, $R^3$ is phenyl, $R^4$ is benzyl, and $R^1$ is selected from the group consisting of:
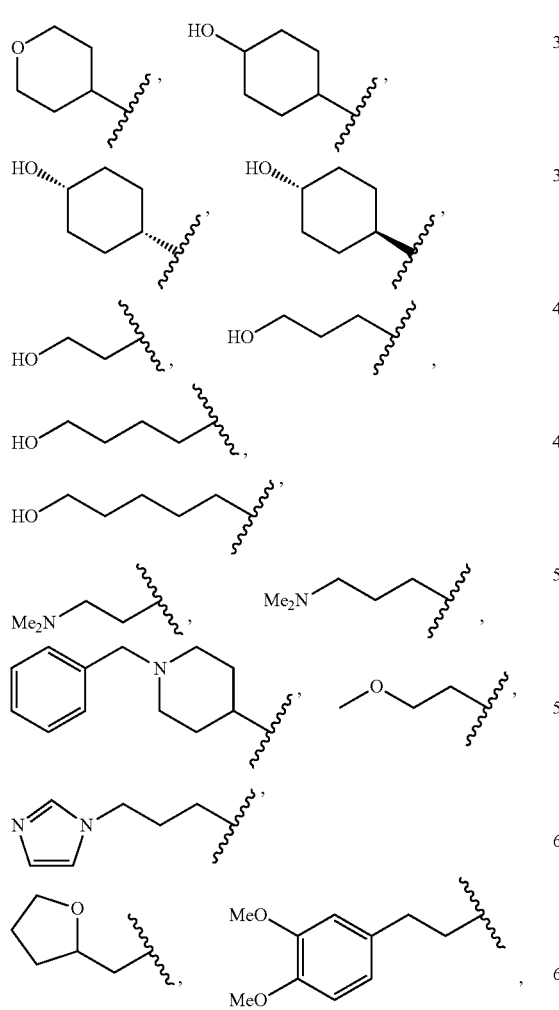
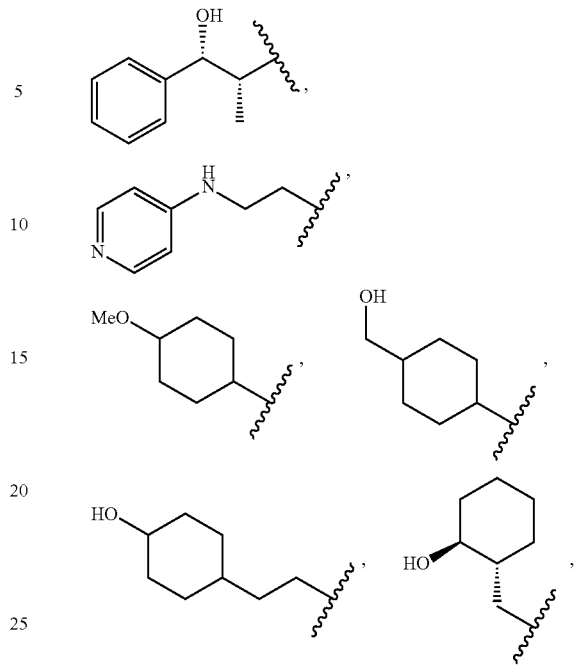
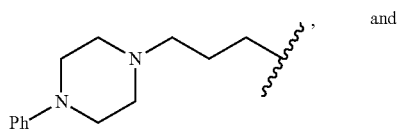

101

-continued

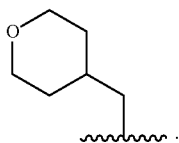

Embodiment 11

The composition of embodiment 6, wherein $R^4$ is 4-methoxybenzyl.

Embodiment 12

The composition of embodiment 11, wherein $R^1$ is selected from the group consisting of:

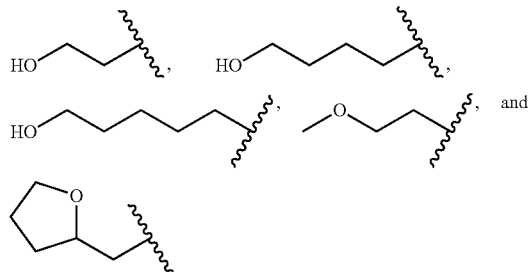

Embodiment 13

The composition of any one of embodiments 1-8 and 11-12, wherein $R^2$ is phenyl, $R^3$ is phenyl, $R^4$ is 4-methoxybenzyl, and $R^1$ is selected from the group consisting of:

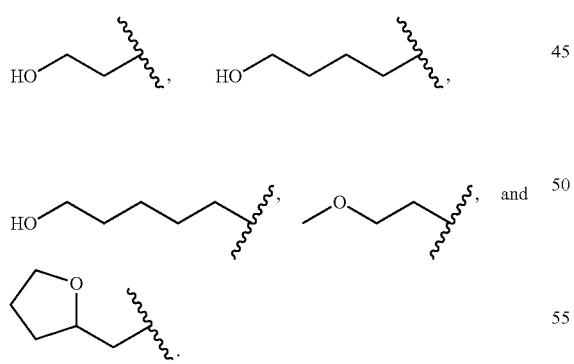

Embodiment 14

The composition of any one of embodiments 1-5, wherein $R^4$ is phenylethyl, wherein the phenyl ring is optionally substituted with one or more substituents selected from the group consisting of alkyl, hydroxyalkyl, alkoxy, and alkoxycarbonyl.

102

Embodiment 15

The composition of embodiment 14, wherein $R^4$ is phenylethyl.

Embodiment 16

The composition of embodiment 14 or 15, wherein $R^1$ is selected from the group consisting of:

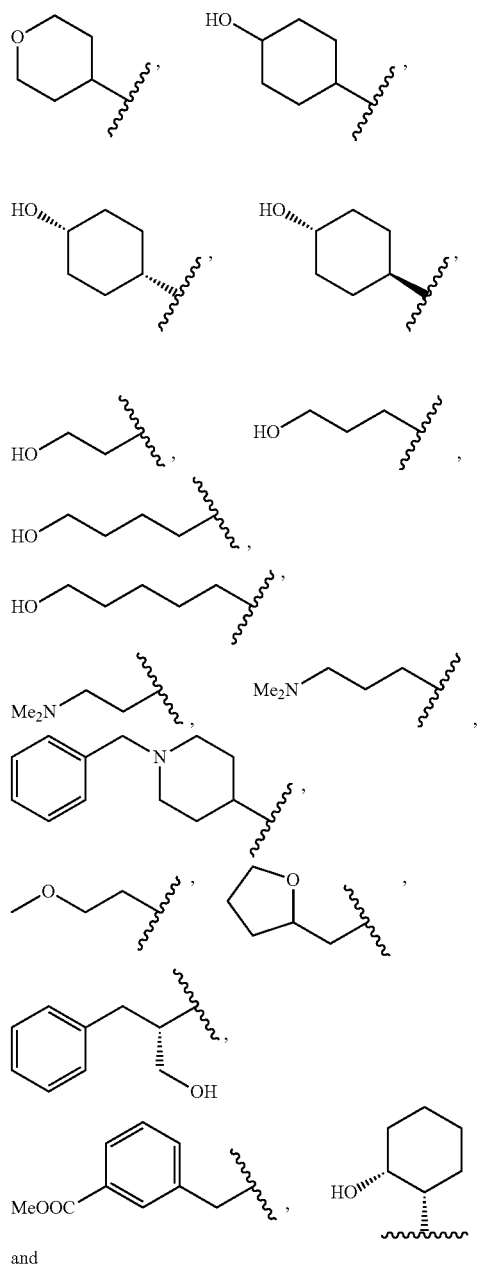

and

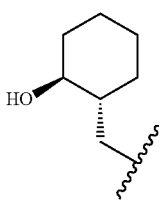

.

Embodiment 17

The composition of embodiment 1-5 and 8, wherein $R^2$ is phenyl, $R^3$ is phenyl, $R^4$ is phenylethyl, and $R^1$ is selected from the group consisting of:

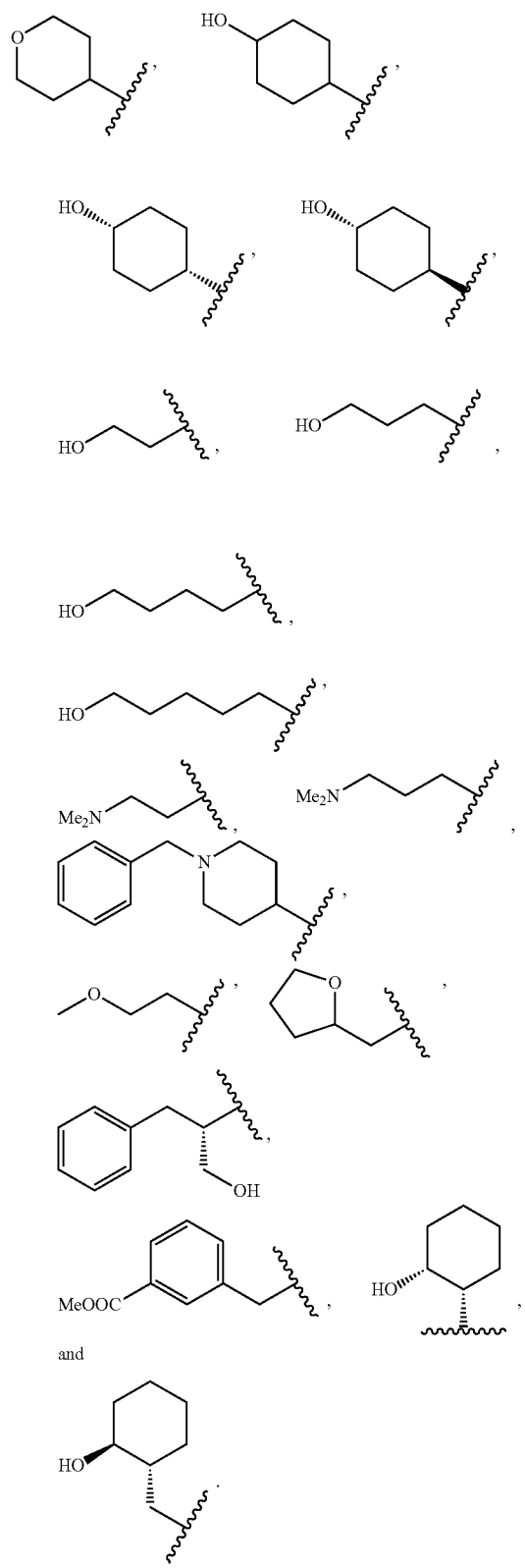

and

Embodiment 18

The composition of any one of embodiments 1-5, wherein $R^4$ is heteroaryl $C_1$-$C_6$ alkyl.

Embodiment 19

The composition of embodiment 18, wherein $R^4$ is

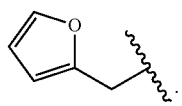 [SMILES: *Cc1ccco1]

Embodiment 20

The composition of embodiment 18 or 19, wherein $R^1$ is selected from the group consisting of:

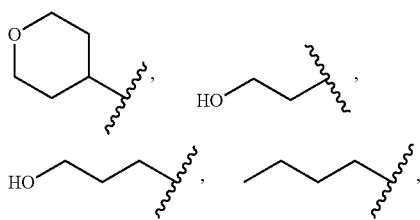

Embodiment 21

The composition of embodiment 1 or 8, wherein $R^2$ is phenyl, $R^3$ is phenyl, $R^4$ is

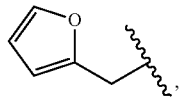

$R^1$ is selected from the group consisting of:

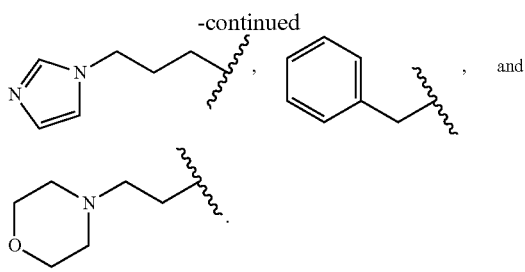

Embodiment 22

The composition of embodiment 6, wherein $R^4$ is selected from the group consisting of: 4-aminosulfonylbenzyl, 4-trifluoromethoxybenzyl, 4-methoxybenzyl, and cyclopropylmethyl.

Embodiment 23

The composition of embodiment 22, wherein $R^1$ is selected from the following:

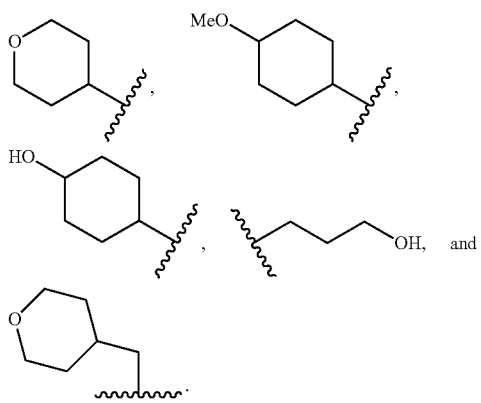

Embodiment 24

The pharmaceutical composition of any one of embodiments 1-22 further including at least one pharmaceutically acceptable carrier.

Embodiment 25

A method for treating cancer in a mammal, including administering to a human or non-human mammal in need thereof a pharmaceutical composition according to any one of embodiments 1-24.

Embodiment 26

The method of embodiment 25, wherein the cancer is a metastatic cancer.

Embodiment 27

The method of embodiment 26, wherein the metastatic cancer is selected from the group consisting of breast cancer, pancreatic cancer, ovarian cancer, colorectal cancer, brain cancer, and prostate cancer.

Embodiment 28

The method of any one of embodiments 25-27, further including administering to the mammal a chemotherapeutic agent.

Embodiment 29

The method of any one of embodiments 25-27, further including subjecting the mammal to a radiation treatment.

Embodiment 30

A method for inhibiting metastatis in a human or non-human mammal in need thereof including administration of a pharmaceutical composition according to any one of embodiments 1-14 to the human or non-human mammal.

Embodiment 31

The method of embodiment 30, wherein said administering is performed post-surgical rescission of a tumor in the human or non-human mammal.

Embodiment 32

The method of embodiment 30, wherein said administering is performed following radiation treatment for a cancer in the human or non-human mammal.

Embodiment 33

A method for reducing the colony formation of cancer cells in a mammal, including administering to a mammal in need thereof a composition of any one of embodiments 1-24.

Embodiment 34

A method for reducing the migration of cancer cells in a mammal, including administering to a mammal in need thereof a composition of any one of embodiments 1-24.

Embodiment 35

A method for preventing cancer in a mammal, including administering to a mammal in need thereof a composition of any one of embodiments 1-24.

Embodiment 36

The method of embodiment 35, wherein the cancer is a metastatic cancer.

Embodiment 37

The method of embodiment 36, wherein the metastatic cancer is selected from the group consisting of breast cancer, pancreatic cancer, ovarian cancer, colorectal cancer, brain cancer, and prostate cancer.

Embodiment 38

The method of any one of embodiments 25-37, wherein the method does not include coadministering a different cancer chemotherapeutic agent.

Embodiment 39

The method of any one of embodiments 25-37, wherein the method does not include coadministering 5-fluoro-Uracil (5-FU) or 5-Fluoro-1-(2-tetrahydrofuryl)-2,4(1H,3H)-pyrimidinedione (Tegafur).

Embodiment 40

The method of any one of embodiments 25-37, wherein the method further includes coadministering 5-fluoro-Uracil (5-FU) or 5-Fluoro-1-(2-tetrahydrofuryl)-2,4(1H,3H)-pyrimidinedione (Tegafur).

Embodiment 41

The method of any one of embodiments 35-37, further including administering to the mammal a different chemotherapeutic agent.

Embodiment 42

The method of any one of embodiments 35-37, further including subjecting the mammal to a radiation treatment.

Embodiment 43

A composition of any one of embodiments 1-24, for use in treating cancer in a mammal.

Embodiment 44

A composition of any one of embodiments 1-24, for use in disrupting a perinucleolar compartment in a cell.

Embodiment 45

A composition of any one of embodiments 1-24, for use in reducing the prevalence of perinucleolar compartment in a cell.

Embodiment 46

A composition of any one of embodiments 1-24, for use in reducing ATP levels produced by metastatic cancer cells, in a mammal afflicted with metastatic cancer.

Embodiment 47

A composition of any one of embodiments 1-24, for use in reducing the colony formation of cancer cells in a mammal.

Embodiment 48

A composition of any one of embodiments 1-24, for use in reducing the migration of cancer cells in a mammal.

Embodiment 49

A composition of any one of embodiments 1-24, for use in preventing cancer in a mammal.

Embodiment 50

A composition of any one of embodiments 1-24, for use in inhibiting metastasis in a mammal.

Embodiment 51

A method for inhibiting metastasis or treating a metastatic cancer in a human or non-human mammal, including:
coadministering to the human or non-human mammal:
(i.) a therapeutically effective amount of a dihydropyrimidine dehydrogenase (DPYD) inhibitor, such as 5-chloro-2,4-dihydroxypyridine (gimeracil) or a pharmaceutically acceptable salt thereof; and
(ii.) a therapeutically effective amount of a compound of formula (I):

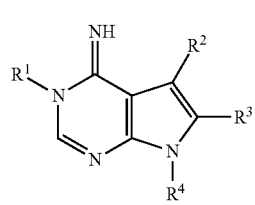

(I)

or a pharmaceutically acceptable salt thereof,
wherein $R^1$ is selected from the group consisting of alkyl, hydroxyalkyl, thioalkyl, alkoxyalkyl, alkylthioalkyl, cycloalkyl, hydroxycycloalkyl, hydroxycycloalkylalkyl, thiocycloalkyl, alkoxycycloalkyl, alkylthiocycloalkyl, dialkylaminoalkyl, heterocyclyl, heterocyclylalkyl, heteroaryl, arylalkyl, arylalkylpiperidin-4-yl, arylpiperazinylalkyl, and heteroarylalkyl,
$R^2$ is aryl or heteroaryl,
$R^3$ is selected from the group consisting of H, alkyl, cycloalkyl, aryl, heteroaryl, arylalkyl, and heteroarylalkyl,
$R^4$ is selected from the group consisting of alkyl, cycloalkyl, cycloalkylalkyl, aryl, heteroaryl, arylalkyl, and heteroarylalkyl,
wherein $R^1$, $R^2$, $R^3$, and $R^4$, other than H, are optionally substituted on the aryl and/or alkyl portion with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, alkylenedioxy, and alkylcarbonyl,
with the proviso that when $R^2$ and $R^3$ are both unsubstituted phenyl and $R^4$ is unsubstituted benzyl, $R^1$ is not 3-hydroxypropyl.

Embodiment 52

The method of embodiment 51, wherein $R^2$ is phenyl, optionally substituted with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl.

Embodiment 53

The method of embodiment 52, wherein $R^2$ is phenyl.

Embodiment 54

The method of any one of embodiments 51-53, wherein $R^3$ is phenyl, optionally substituted with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl.

Embodiment 55

The method of embodiment 54, wherein $R^3$ is phenyl.

Embodiment 56

The method of any one of embodiments 51-55, wherein $R^4$ is benzyl, wherein the phenyl ring is optionally substituted with one or more substituents selected from the group consisting of alkyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, and alkylcarbonyl.

Embodiment 57

The method of embodiment 56, wherein $R^4$ is benzyl.

Embodiment 58

The method of any one of embodiments 51-57, wherein $R^1$ is a 5 or 6-membered heterocyclyl group having at least one hetero atom selected from the group consisting of O, N, and S; a hydroxy $C_1$-$C_7$ cycloalkyl group; a hydroxy $C_1$-$C_6$ alkyl group; a N,N-di($C_1$-$C_6$ alkyl)amino $C_1$-$C_6$ alkyl group; a $C_1$-$C_6$ alkoxy $C_1$-$C_6$ alkyl group; a heteroaryl $C_1$-$C_6$ alkyl group; a heterocyclyl $C_1$-$C_6$ alkyl group; phenyl $C_1$-$C_6$ alkyl group where the phenyl ring is substituted with one or more $C_1$-$C_6$ alkoxy groups; N-benzyl piperazinyl; N-phenyl piperazinylalkyl; a phenyl $C_1$-$C_6$ alkyl group where the alkyl is substituted with a hydroxy group; or a 5 or 6 membered heteroaryl amino $C_1$-$C_6$ alkyl group wherein the heteroaryl group has at least one hetero atom selected from the group consisting of O, N, and S.

Embodiment 59

The method of any one of embodiments 51-58, wherein $R^1$ is selected from the group consisting of:

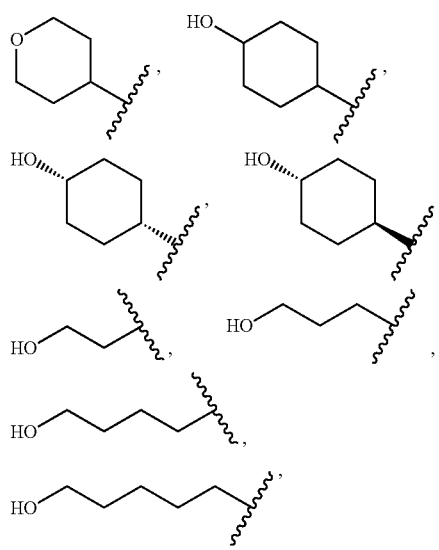

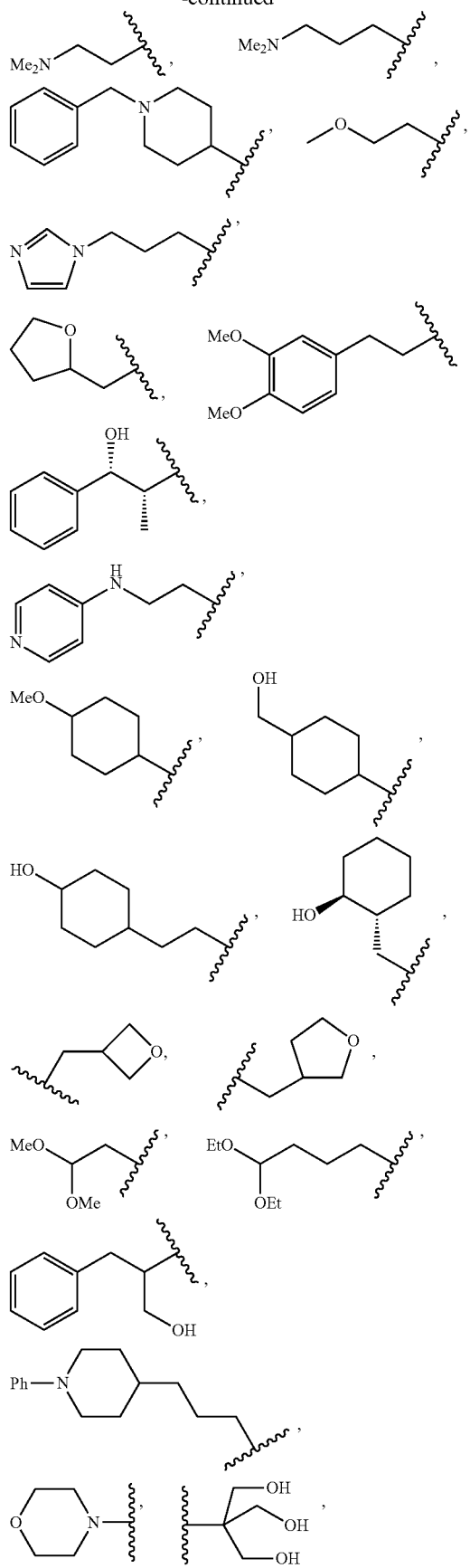

-continued
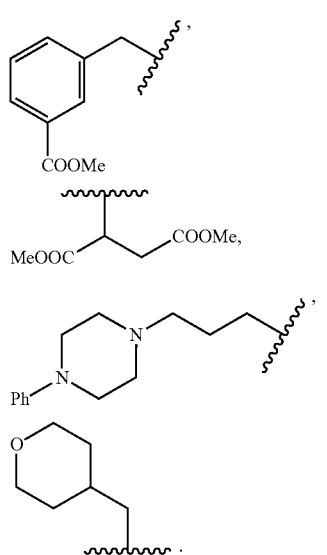
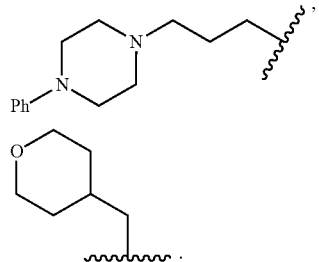
Embodiment 60
The method of any one of embodiments 51-59, wherein $R^2$ is phenyl, $R^3$ is phenyl, $R^4$ is benzyl, and $R^1$ is selected from the group consisting of:
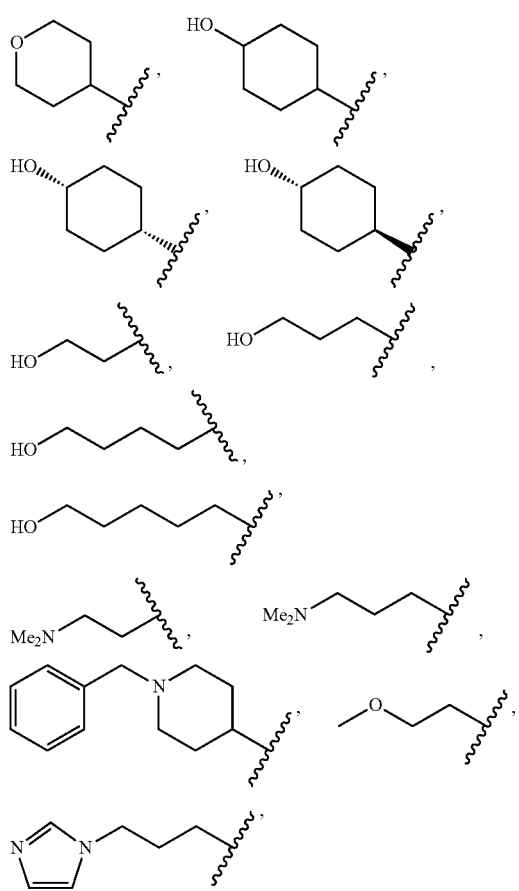
-continued
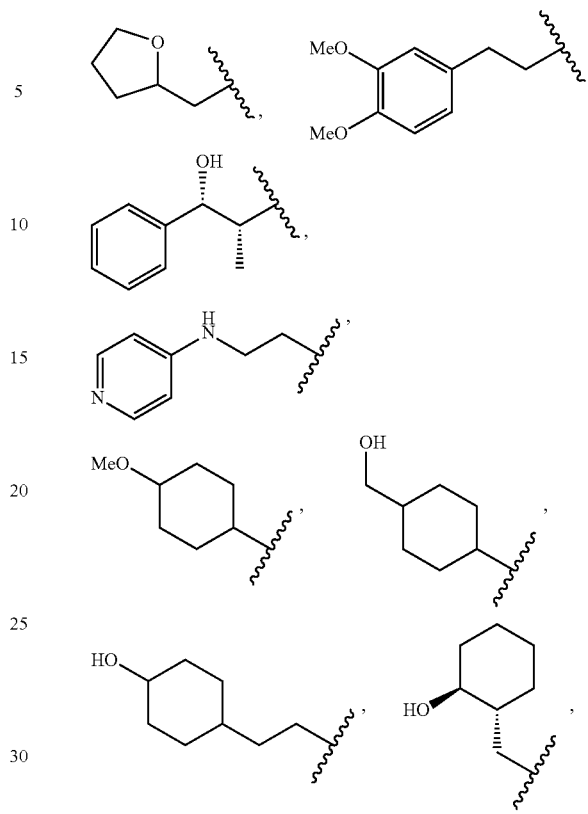
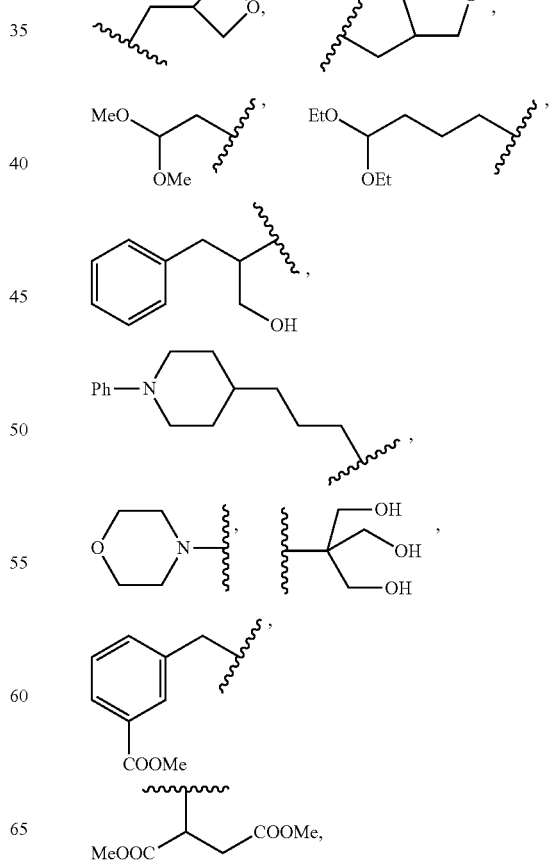

113

-continued

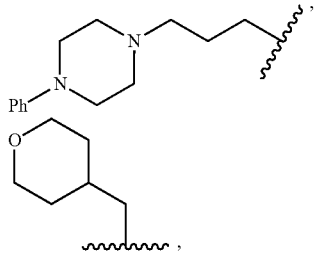
and

Embodiment 61

The method of embodiment 56, wherein $R^4$ is 4-methoxybenzyl.

Embodiment 62

The method of embodiment 61, wherein $R^1$ is selected from the group consisting of:

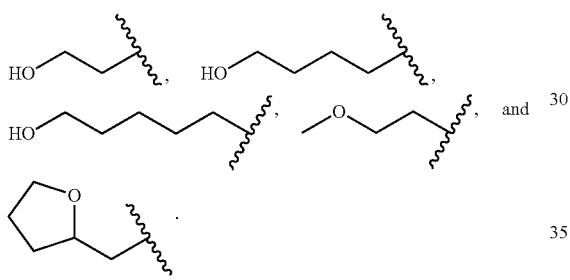

Embodiment 63

The method of any one of embodiments 51-58 and 61-62, wherein $R^2$ is phenyl, $R^3$ is phenyl, $R^4$ is 4-methoxybenzyl, and $R^1$ is selected from the group consisting of:

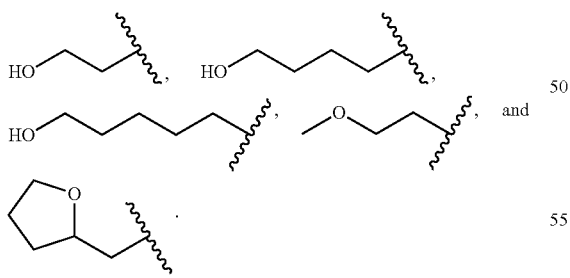

Embodiment 64

The method of any one of embodiments 51-55, wherein $R^4$ is phenylethyl, wherein the phenyl ring is optionally substituted with one or more substituents selected from the group consisting of alkyl, hydroxyalkyl, alkoxy, and alkoxycarbonyl.

114

Embodiment 65

The method of embodiment 64, wherein $R^4$ is phenylethyl.

Embodiment 66

The method of embodiment 64 or 65, wherein $R^1$ is selected from the group consisting of:

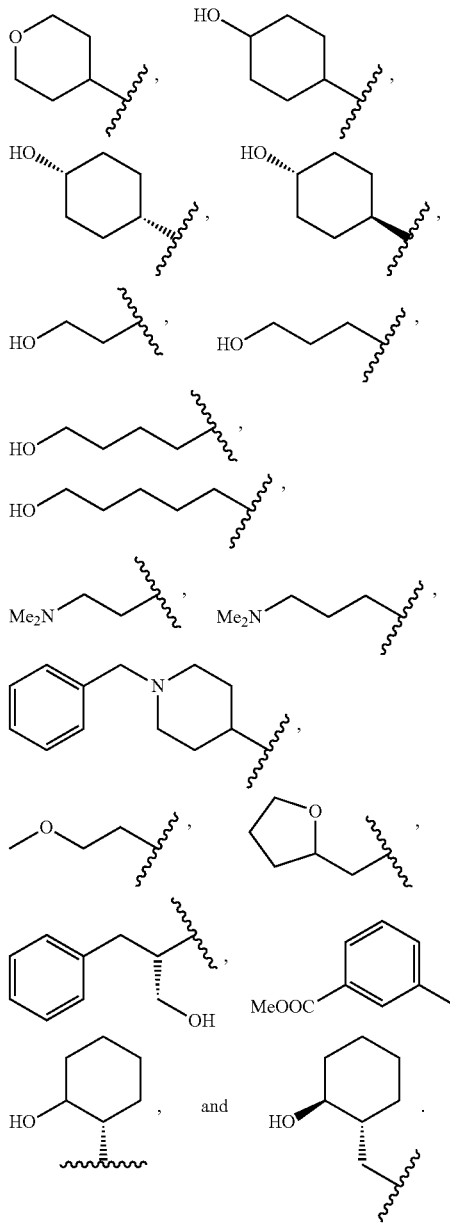

Embodiment 67

The method of embodiment 51-55 and 58, wherein $R^2$ is phenyl, $R^3$ is phenyl, $R^4$ is phenylethyl, and $R^1$ is selected from the group consisting of:

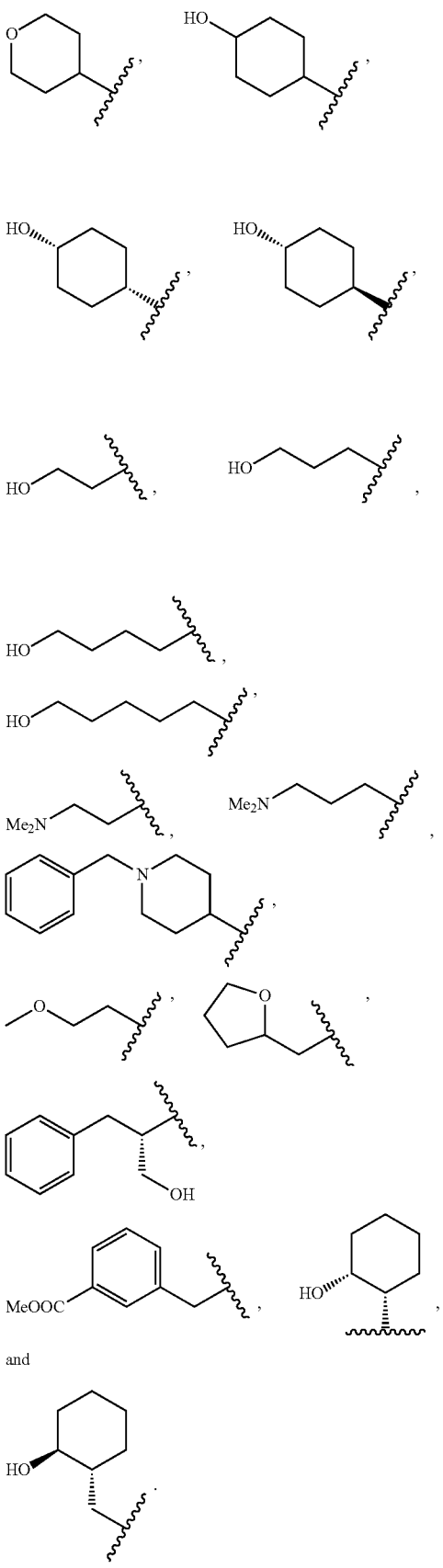

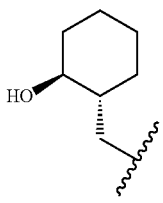

Embodiment 68

The method of any one of embodiments 51-55, wherein R is heteroaryl $C_1$-$C_6$ alkyl.

Embodiment 69

The method of embodiment 68, wherein $R^4$ is

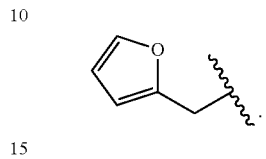

Embodiment 70

The method of embodiment 68 or 69, wherein $R^1$ is selected from the consisting of the following:

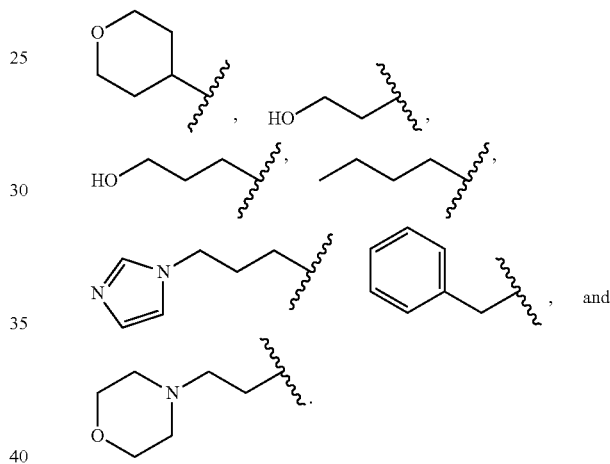

Embodiment 71

The method of embodiment 51 or 58, wherein $R^2$ is phenyl, $R^3$ is phenyl, $R^4$ is

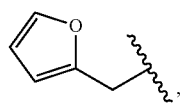 [SMILES: *Cc1ccco1]

and
$R^1$ is selected from the group consisting of:

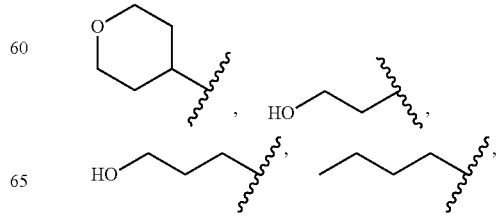

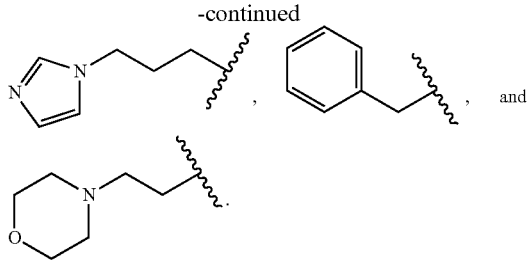

Embodiment 72

The method of embodiment 56, wherein R⁴ is selected from the group consisting of:
4-aminosulfonylbenzyl, 4-trifluoromethoxybenzyl, 4-methoxybenzyl, and cyclopropylmethyl.

Embodiment 73

The method of embodiment 72, wherein R¹ is selected from the following:

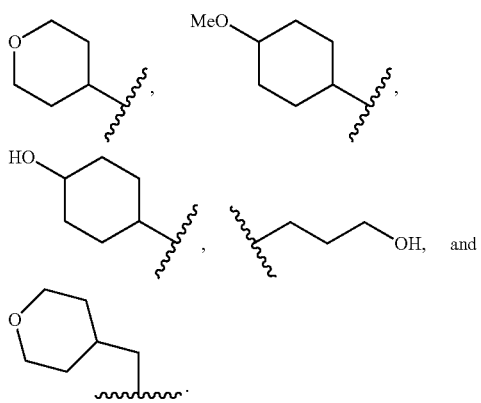

Embodiment 74

The method of any one of embodiments 51-73, wherein the method does not include coadministering a different cancer chemotherapeutic agent.

Embodiment 75

The method of any one of embodiments 51-73, wherein the method does not include coadministering 5-fluoro-Uracil (5-FU) or 5-Fluoro-1-(2-tetrahydrofuryl)-2,4(1H,3H)-pyrimidinedione (Tegafur).

Embodiment 76

The method of any one of embodiments 51-73, wherein the method further includes coadministering 5-fluoro-Uracil (5-FU) or 5-Fluoro-1-(2-tetrahydrofuryl)-2,4(1H,3H)-pyrimidinedione (Tegafur).

Embodiment 77

The method of any one of embodiments 51-76, wherein the human or non-human mammal is in need of inhibition of metastasis for a cancer selected from the group consisting of breast cancer, pancreatic cancer, ovarian cancer, colorectal cancer, brain cancer, and prostate cancer.

Embodiment 78

The method of any one of embodiments 51-77, wherein said administering is performed post-surgical rescission of a tumor in the human or non-human mammal.

Embodiment 79

The method of any one of embodiments 51-78, wherein said administering is performed following radiation treatment for a cancer in the human or non-human mammal.

Embodiment 80

Use of a DPYD inhibitor such as gimeracil or a pharmaceutically acceptable salt thereof and a compound of formula I as recited in any one of embodiments 1-23 or a pharmaceutically acceptable salt thereof in the preparation of a medicament for the inhibition of metastasis in a human or non-human mammal.

Embodiment 81

Use of a DPYD inhibitor such as gimeracil or a pharmaceutically acceptable salt thereof and a compound of formula I as recited in any one of embodiments 1-23 or a pharmaceutically acceptable salt thereof in the preparation of a medicament for the treatment of a cancer in a human or non-human mammal.

Embodiment 82

Use together of a DPYD inhibitor such as gimeracil or a pharmaceutically acceptable salt thereof and a compound of formula I as recited in any one of embodiments 1-23 or a pharmaceutically acceptable salt thereof in the inhibition of metastasis in a human or non-human mammal.

Embodiment 83

Use together of a DPYD inhibitor such as gimeracil or a pharmaceutically acceptable salt thereof and a compound of formula I as recited in any one of embodiments 1-23 or a pharmaceutically acceptable salt thereof in the treatment of a cancer in a human or non-human mammal.

In any of the embodiments of the invention, the compound of formula I or pharmaceutically acceptable salt thereof may have perinucleolar compartment formation-inhibiting and/or -disrupting activity in mammalian cells, such as human, cells and/or inhibits migration and/or metastasis of mammalian, such as human, cancer cells such as those of recognized metastatic cancers.

It should be understood that where compounds of formula I are provided, any or all stereoisomers may be provided in at least substantially pure form or in any combination or mixture and thus all such stereoisomers and combinations thereof which are readily discernable by those skilled in the art are provided and disclosed herein.

In further explanation of the terms coadministration or coadministering what is meant herein is that each coadministered pharmaceutical component is administered in sufficient temporal proximity to each other that each (or its active metabolites) will be present in the subject mammal, such as human patient, at the same time (in an at least partially overlapping manner). Thus coadministered components of treated may be administered at or around the same time, such as simultaneously or within the same hour or same day or even on different days so long as the coadministered components are active in the subject mammal at the same time at least some of the time.

It should be understood that either or both of the therapeutically effective amount of each of the DPYD inhibitor and the compound of formula I may in some embodiments be lower than the minimum therapeutically effective dose of each agent alone due to synergistic effects. Thus in the combination and coadministration embodiments, the therapeutically effective amount of each agent may be an amount that is therapeutically effective for the agent when used alone or it may, for one or both of the agents, be less than that amount. The treatment of the invention may, for example, be administered daily or every 2, 3, 4, 5, 6, or 7 days generally and may be continued for example, for at least a week, at least a month, at least 2-12 months or for at least any number of months therein, or for at least one year. The treatment may, for example, be continued indefinitely.

It should be understood that wherever in this disclosure a genus of species of compounds is disclosed, this disclosure explicitly also discloses every possible subset of the genus excluding any one or more of the members of the genus.

Wherever in this disclosure the terms include(s) or including or comprise(s) or comprising is recited in connection with an embodiment of the invention, corresponding embodiments instead reciting "consisting essentially of" or reciting "consisting of" are also provided by the invention.

Still further combination embodiments and variations thereof provided by the present invention are found in the appended claims. Although the disclosure within is directed to the preferred embodiments of the invention, other variations and modifications may be made without departing from the spirit or scope of the invention. Moreover, features described in connection with one embodiment set forth in the specification and claims may be used in conjunction with other embodiments, even if not explicitly stated within.

What is claimed is:

1. A method for treating cancer in a mammal, comprising administering to a human or non-human mammal in need thereof a pharmaceutical composition comprising:
   (i) a therapeutically effective amount of 5-chloro-2,4-dihydroxypyridine (gimeracil) or a pharmaceutically acceptable salt thereof; and
   (ii) a therapeutically effective amount of a compound of formula (I):

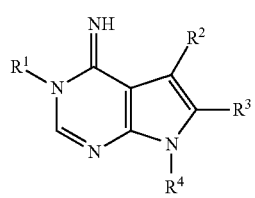

or a pharmaceutically acceptable salt thereof,
wherein $R^1$ is selected from the group consisting of alkyl, hydroxyalkl, thioalkyl, alkoxyalkyl, alkylthioalkyl, cycloalkyl, hydroxycycloalkyl, hydroxycycloalkylalkyl, thiocycloalkyl, alkoxycycloalkyl, alkylthiocycloalkyl, dialkylaminoalkyl, heterocyclyl, heterocyclylalkyl, heteroaryl, arylalkyl, arylalkylpiperidin-4-yl, arylpiperazinylalkyl, and heteroarylalkyl,
$R^2$ is aryl or heteroaryl,
$R^3$ is selected from the group consisting of H, alkyl, cycloalkyl, aryl, heteroaryl, arylalkyl, and heteroarylalkyl,
$R^4$ is selected from the group consisting of alkyl, cycloalkyl, cycloalkylalkyl, aryl, heteroaryl, arylalkyl, and heteroarylalkyl,
wherein $R^1$, $R^2$, $R^3$, and $R^4$, other than H, are optionally substituted on the aryl and/or alkyl portion with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, alkylenedioxy, and alkylcarbonyl,
with the proviso that when $R^2$ and $R^3$ are both unsubstituted phenyl and $R^4$ is unsubstituted benzyl, $R^1$ is not 3-hydroxypropyl,
wherein the cancer is a metastatic cancer selected from the group consisting of breast cancer, pancreatic cancer, ovarian cancer, colorectal cancer, and prostate cancer, and
wherein 5-fluorouracil is not coadministered to the human or non-human mammal.

2. The method of claim 1, wherein the compound of formula I is trans-4-(7-benzyl-4-imino-5,6-diphenylpyrrolo[2,3-d]pyrimidin-3-yl)cyclohexan-1-ol.

3. The method of claim 1, wherein the metastatic cancer is pancreatic cancer.

4. The method of claim 3, wherein the compound of formula I is trans-4-(7-benzyl-4-imino-5,6-diphenylpyrrolo[2,3-d]pyrimidin-3-yl)cyclohexan-1-ol.

5. The method of claim 1, wherein the metastatic cancer is selected from the group consisting of breast cancer, ovarian cancer, colorectal cancer, and prostate cancer.

6. The method of claim 5, wherein the compound of formula I is trans-4-(7-benzyl-4-imino-5,6-diphenylpyrrolo[2,3-d]pyrimidin-3-yl)cyclohexan-1-ol.

7. A method for inhibiting metastasis or treating a metastatic cancer in a human or non-human mammal, comprising:
   coadministering to a human or non-human mammal having a metastatic cancer:
   (i.) a therapeutically effective amount of 5-chloro-2,4-dihydroxypyridine (gimeracil) or a pharmaceutically acceptable salt thereof; and
   (ii.) a therapeutically effective amount of a compound of formula (I):

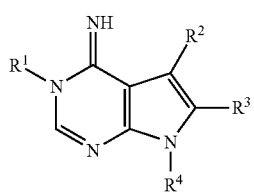

or a pharmaceutically acceptable salt thereof,
wherein $R^1$ is selected from the group consisting of alkyl, hydroxyalkyl, thioalkyl, alkoxyalkyl, alkylthioalkyl, cycloalkyl, hydroxycycloalkyl, hydroxycycloalkylalkyl, thiocycloalkyl, alkoxycycloalkyl, alkylthiocycloalkyl, dialkylaminoalkyl, heterocyclyl, heterocyclylalkyl, heteroaryl, arylalkyl, arylalkylpiperidin-4-yl, arylpiperazinylalkyl, and heteroarylalkyl, $R^2$ is aryl or heteroaryl, $R^3$ is selected from the group consisting of H, alkyl, cycloalkyl, aryl, heteroaryl, arylalkyl, and heteroarylalkyl, $R^4$ is selected from the group consisting of alkyl, cycloalkyl, cycloalkylalkyl, aryl, heteroaryl, arylalkyl, and heteroarylalkyl, wherein $R^1$, $R^2$, $R^3$, and $R^4$, other than H, are optionally substituted on the aryl and/or alkyl portion with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, alkylenedioxy, and alkylcarbonyl, with the proviso that when $R^2$ and $R^3$ are both unsubstituted phenyl and $R^4$ is unsubstituted benzyl, $R^1$ is not 3-hydroxypropyl, wherein the compound of formula 1 or pharmaceutically acceptable salt thereof inhibits the formation of the perinucleolar compartment or disrupts the perinucleolar compartment or both, and wherein the metastatic cancer is selected from the group consisting of breast cancer, pancreatic cancer, ovarian cancer, colorectal cancer, and prostate cancer, and wherein 5-fluorouracil is not coadministered to the human or non-human mammal.

8. The method of claim 7, wherein the compound of formula I is trans-4-(7-benzyl-4-imino-5,6-diphenylpyrrolo[2,3-d]pyrimidin-3-yl)cyclohexan-1-ol.

9. The method of claim 7, wherein the metastatic cancer is selected from the group consisting of breast cancer, ovarian cancer, colorectal cancer, and prostate cancer.

10. The method of claim 8, wherein the metastatic cancer is selected from the group consisting of breast cancer, ovarian cancer, colorectal cancer, and prostate cancer.

* * * * *